US008383889B2

(12) United States Patent
Hayes et al.

(10) Patent No.: US 8,383,889 B2
(45) Date of Patent: Feb. 26, 2013

(54) TRANSGENIC PLANTS MODIFIED FOR REDUCED CADMIUM TRANSPORT, DERIVATIVE PRODUCTS, AND RELATED METHODS

(75) Inventors: Alec J. Hayes, Chesterfield, VA (US); Chengalrayan Kudithipudi, Midlothian, VA (US); Rutger S. van der Hoeven, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 804 days.

(21) Appl. No.: 12/333,681

(22) Filed: Dec. 12, 2008

(65) Prior Publication Data
US 2009/0183280 A1 Jul. 16, 2009

Related U.S. Application Data

(60) Provisional application No. 60/996,982, filed on Dec. 13, 2007.

(51) Int. Cl.
C12N 15/09 (2006.01)
C12N 15/82 (2006.01)
C12N 15/29 (2006.01)
A01H 5/00 (2006.01)

(52) U.S. Cl. ........ 800/289; 800/278; 800/298; 800/285; 435/320.1; 435/468; 435/419; 536/23.6

(58) Field of Classification Search .................. None
See application file for complete search history.

(56) References Cited

U.S. PATENT DOCUMENTS

| | | | |
|---|---|---|---|
| 4,376,110 A | 3/1983 | David et al. | |
| 4,459,355 A | 7/1984 | Cello et al. | |
| 4,469,863 A | 9/1984 | Ts'o et al. | |
| 4,795,855 A | 1/1989 | Fillatti et al. | |
| 4,940,838 A | 7/1990 | Schilperoort et al. | |
| 4,945,050 A | 7/1990 | Sanford et al. | |
| 5,015,580 A | 5/1991 | Christou et al. | |
| 5,034,506 A | 7/1991 | Summerton et al. | |
| 5,216,141 A | 6/1993 | Benner | |
| 5,235,033 A | 8/1993 | Summerton et al. | |
| 5,386,023 A | 1/1995 | Sanghvi et al. | |
| 5,525,716 A | 6/1996 | Olsen et al. | |
| 5,602,240 A | 2/1997 | De Mesmaeker et al. | |
| 5,637,684 A | 6/1997 | Cook et al. | |
| 6,225,529 B1 | 5/2001 | Lappegard et al. | |
| 6,403,862 B1 | 6/2002 | Jiao et al. | |
| 6,407,315 B1 | 6/2002 | Jiao et al. | |
| 6,429,362 B1 | 8/2002 | Crane | |
| 6,479,734 B2 | 11/2002 | Iba et al. | |
| 6,528,704 B1 | 3/2003 | Linnestad et al. | |
| 6,903,205 B2 | 6/2005 | Linnestad et al. | |
| 7,122,658 B1 | 10/2006 | Lappegard et al. | |
| 2006/0200872 A1* | 9/2006 | Conkling et al. | 800/278 |

FOREIGN PATENT DOCUMENTS

| | | |
|---|---|---|
| WO | WO 00/11177 | 3/2000 |
| WO | WO 02/081707 | 10/2002 |
| WO | WO 2005/090583 | 9/2005 |

OTHER PUBLICATIONS

Guerinot et al. Plant Physiology, 2001, vol. 125, pp. 164-167.*
Hussain et al., "P-Type ATPase Heavy Metal Transporters with Roles in Essential Zinc Homeostasis in Arabidopsis." The Plant Cell, vol. 16, 1327-1339, May 2004.
Gravot et al., "AtHMA3, a plant $P_{1B}$-ATPase, functions as a Cd/Pb transporter in yeast." FEBS Letters 561 (2004) 22-28.
Mills et al., "The plant $P_{1B}$-type ATPase AtHMA4 transports Zn and Cd and plays a role in detoxification of transition metals supplied at elevated levels." FEBS Letters 579 (2005) 783-791.
Verret et al. "Overexpression of AtHMA4 enhances root-to-shoot translocation of zinc and cadmium and plant metal tolerance." FEBS Letters 576 (2004) 306-312.
Vögeli-Lange et al., "Subcellular Localization of Cadmium and Cadmium-binding Peptides in Tobacco Leaves." Plant Physiol. (1990) 92:1086-1093.
Pavlíková et al., "The evaluation of cadmium, zinc and nickel accumulation ability of transgenic tobacco bearing different transgenes." Plant Soil Environ., 50, 2004 (12): 513-517.
European Office Action mailed on Oct. 3, 2011, in corresponding European Application No. 08860815.3-1212.
T. Elmayan et al., Synthesis of a bifunctional metallothionein/β-glucuronidase fusion protein in transgenic tobacco plants as a means of reducing leaf cadmium levels, 6(3) The Plant Journal 433-440 (1994).
N. Lugon-Moulin et al., Critical Review of the Science and Options for Reducing Cadmium in Tobacco (Nicotiana Tabacum L.) and Other Plants, 83 Advances in Agronomy 112-180 (2004).
L. Bovet et al., Cadmium partitioning and gene expression studies in Nicotiana tabacum and Nicotiana rustica, 128 Physiologia Plantarum 466-475 (2006).

(Continued)

*Primary Examiner* — Medina A Ibrahim
(74) *Attorney, Agent, or Firm* — Buchanan Ingersoll & Rooney PC

(57) ABSTRACT

Various embodiments are directed to transgenic plants, including transgenic tobacco plants and derivative seeds, genetically modified to impede the transport of Cadmium (Cd) from the root system to aerial portions of transgenic plants by reducing the expression levels of HMA-related transporters. Various embodiments are directed to transgenic tobacco plants genetically modified to stably express a RNAi construct encoding RNAi polynucleotides that enable the degradation of endogenous NtHMA RNA variants. Reduced expression of NtHMA transporters in transgenic plants results in substantially reduced content of Cadmium (Cd) in the leaf lamina. Various consumable products that are substantially free or substantially reduced in Cd content can be produced by incorporating leaves derived from transgenic tobacco plants modified to reduce the expression of NtHMA transporters.

14 Claims, 11 Drawing Sheets

OTHER PUBLICATIONS

M. Courbot et al., *A Major Quantitative Trait Locus for Cadmium Tolerance* in Arabidopsis halleri *Colocalizes with HMA4, a Gene Encoding a Heavy Metal ATPase*[1][O], 144 Plant Physiology 1052-1065 (Jun. 2007).

V. Korenkov et al., *Enhancing tonoplast Cd/H antiport activity increases Cd, Zn, and Mn tolerance, and impacts root/shoot Cd partitioning* in Nicotiana tabacum L., 226 Planta 1379-1387 (2007).

J. Lee et al., *Functional Expression of a Bacterial Heavy Metal Transporter in Arabidopsis Enhances Resistance to and Decreases Uptake of Heavy Metals* [1][w], 133 Plant Physiology 589-596 (Oct. 2003).

W Song et al., *Engineering tolerance and accumulation of lead and cadmium in transgenic plants*, 21(8) Nature Biotechnology 914-919 (Aug. 2003).

R.J.M. Van Den Bekerom et al., *Transformation vector with loxp-sites and aadA for targeting the trnA and trnI region of the tobacco chloroplast*, EBI accession No. EMBL:DQ073476 (Jun. 21, 2005).

L. Williams et al., $P_{1B}$-*ATPases—an ancient family of transition metal pumps with diverse functions in plants*, 10(10) Trends in Plant Science 491-502 (Oct. 2005).

International Search Report from PCT/EP2008/010546 mailed on Apr. 22, 2009.

\* cited by examiner

Table 1

| Exon | Nucleotides | Position |
|---|---|---|
| Exon 1 | 1-303 | 724-1026 |
| Exon 2 | 304-561 | 3245-3502 |
| Exon 3 | 562-659 | 7364-7461 |
| Exon 4 | 660-915 | 11525-11780 |
| Exon 5 | 916-1056 | 11866-12007 |
| Exon 6 | 1057-1381 | 12317-12644 |
| Exon 7 | 1382-1584 | 13108-13310 |
| Exon 8 | 1585-1787 | 13456-13658 |
| Exon 9 | 1788-3285 | 14278-15775 |
| Exon 10 | 3286-3618 | 16097-16429 |
| Exon 11 | 3619-4392 | 16650-17423 |

FIG. 3A

RNAi Construct NtHMA (660-915) Encoding RNAi Polynucleotide SEQ ID NO:41

Sense Sequence SEQ ID NO:38

5'-ATTTGTAGTGCCAGCCCAGACCGTTGAATCTATTTGCTTAGAAAC
TGGAAACGACTCGCCTGTCAGTGTTTTCTCGTCCACGTCACATTCCC
CTTCCATTACAACTCCATCAATAGGTATAGTTTCACCAGCTTTAACAG
CAAGAATGCTATTCAACTTGACTTCATCAACATTTACGACTTCTCCAC
TTTCAGCTAAAACTGCTGTTGGAGGGACTATATTGACCAGTGATGAC
ATAGCAGCAGTAGCCTACATAACCA-3'

Spacer Sequence SEQ ID NO:39

5'-AGCCTGAAGAATTGAGCAAATAACATTAACAAACAATACTTGAAG
TTTCAGCACTAAATAAATGAAGCATGAAGGAATACTACACTACCATTT
AGA-3'

Reverse Complementary Sequence SEQ ID NO:40

5'-TGGTTATGTAGGCTACTGCTGCTATGTCATCACTGGTCAATATAG
TCCCTCCAACAGCAGTTTTAGCTGAAAGTGGAGAAGTCGTAAATGTT
GATGAAGTCAAGTTGAATAGCATTCTTGCTGTTAAAGCTGGTGAAAC
TATACCTATTGATGGAGTTGTAATGGAAGGGGAATGTGACGTGGAC
GAGAAAACACTGACAGGCGAGTCGTTTCCAGTTTCTAAGCAAATAGA
TTCAACGGTCTGGGCTGGCACTACAAAT-3'

FIG. 3B

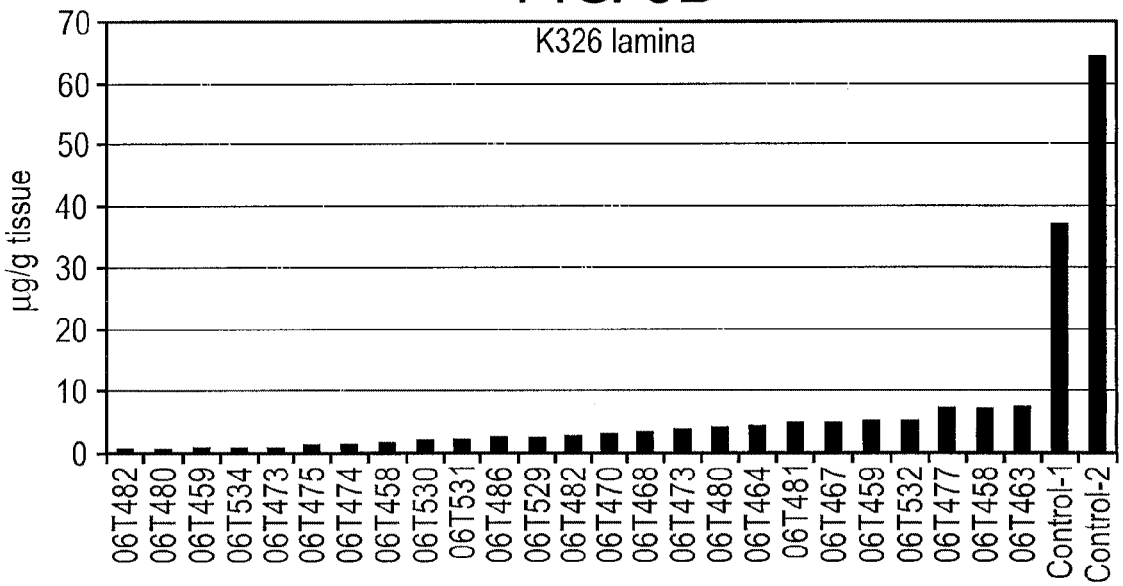

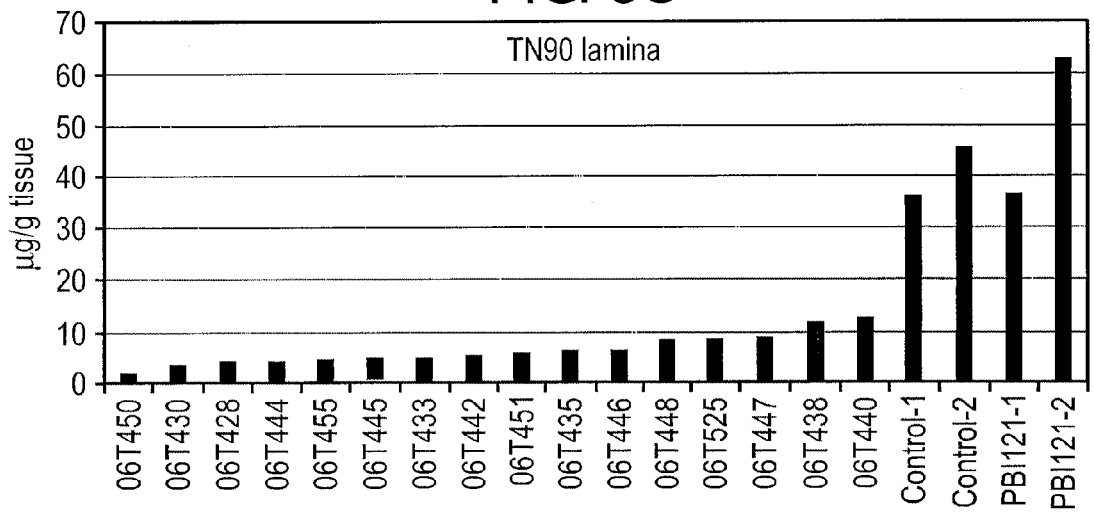
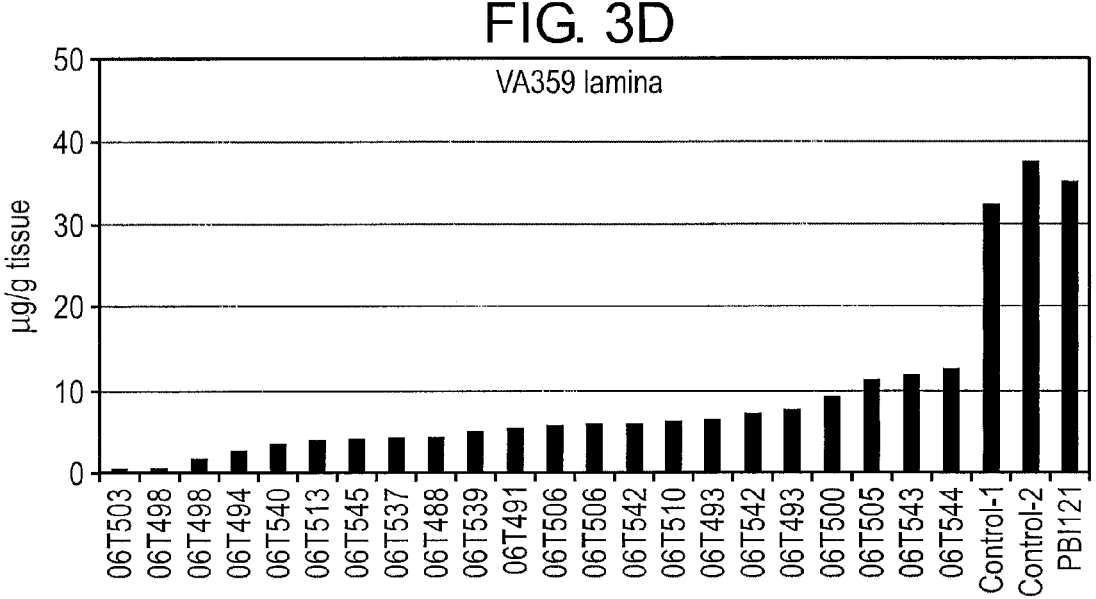

FIG. 4A

RNAi Construct NtHMA (1382-1584) Encoding RNAi Polynucleotide
SEQ ID NO:45

Sense Sequence SEQ ID NO:42
5'-TGAGAGCAAGTCAGGTCATCCGATGGCAGCCGCTCTGGTGGAC
TATGCACAATCAAATTCCGTTGAGCCAAAGCCTGATAGAGTTGAGCA
GTTTCAAAATTTTCCTGGTGAAGGGATATTTGGAAGAATTGATGGAAT
GGAAATCTATGTCGGGAATAGGAAAATTTCTTCAAGAGCTGGATGTA
CCACAGG-3'

Spacer Sequence SEQ ID NO:43
5'-TAAATGGTTGAATCATTTCTTATGCTCATAGTAGAGATAAAACATC
AGAGTTATAATTATAAGTATATGATTTCTCAGTTAATTTTGCTGTTAG
ATTTTCTTTGACCTGTTTAGCACTAATGCGGTGGATGTTTGAA-3'

Reverse Complementary Sequence SEQ ID NO:44
5'-CCTGTGGTACATCCAGCTCTTGAAGAAATTTTCCTATTCCCGACA
TAGATTTCCATTCCATCAATTCTTCCAAATATCCCTTCACCAGGAAAA
TTTTGAAACTGCTCAACTCTATCAGGCTTTGGCTCAACGGAATTTGAT
TGTGCATAGTCCACCAGAGCGGCTGCCATCGGATGACCTGACTTGC
TCTCAATGC-3'

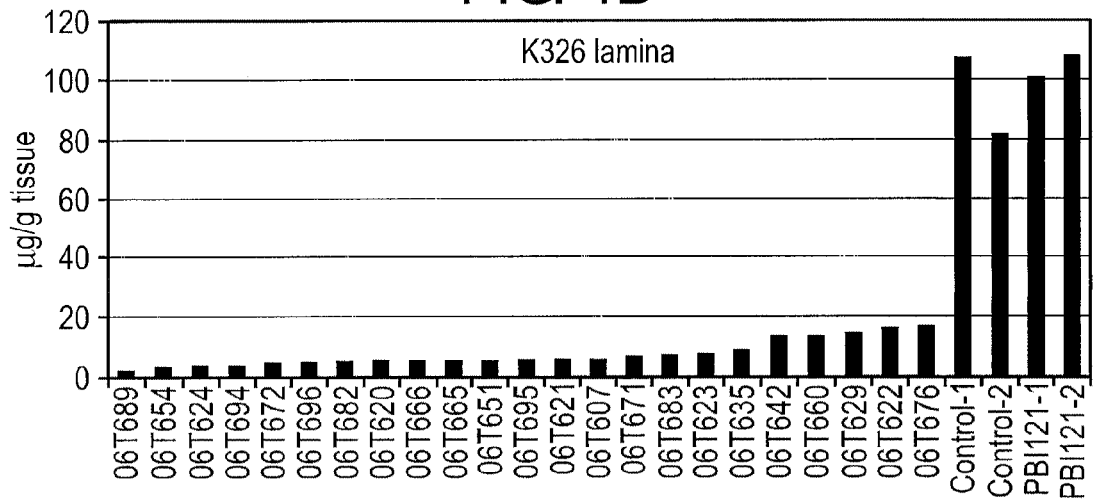

FIG. 4B

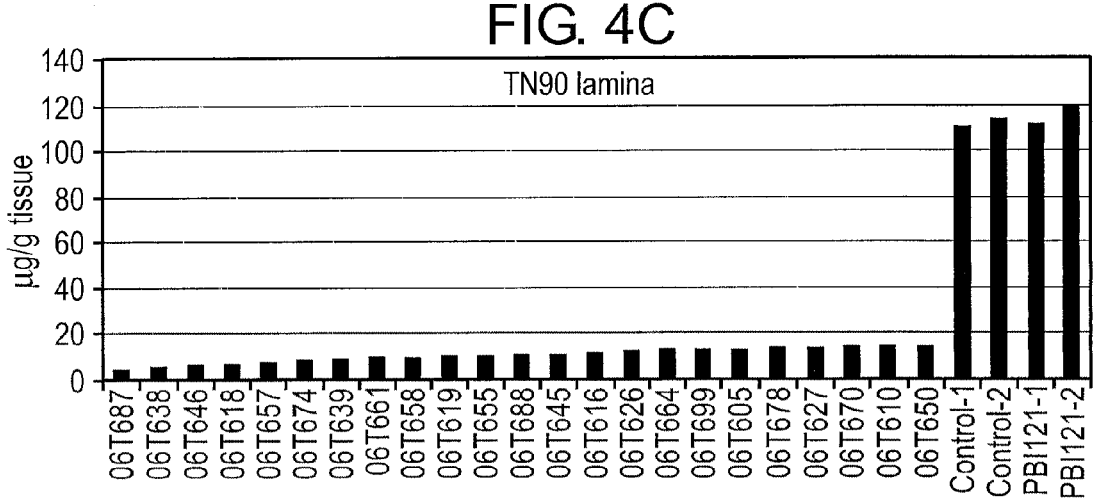
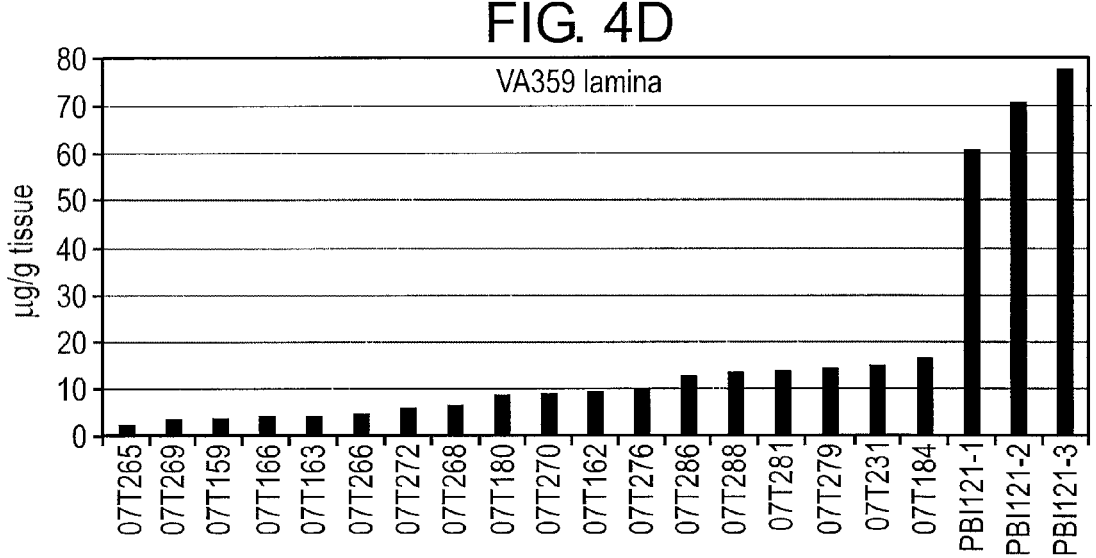

SEQUENCE LISTING

<160> NUMBER OF SEQ ID NOS: 61

<210> SEQ ID NO 1
<211> LENGTH: 17921
<212> TYPE: DNA
<213> ORGANISM: Nicotiana tabacum

```
<400> SEQUENCE: 1
gcgtgagcta tgagaaagcg ccacgcttcc cgaagggaga aaggcggaca ggtatccggt    60
aagcggcagg gtcggaacag gagagcgcac gagggagctt ccaggggaa acgcctggta    120 tctttatagt cctgtcgggt ttcgccacct ctgacttgag cgtcgatttt tgtgatgctc    180 gtcaggggg cggagcctat ggaaaaacgc cagcaacgcg gcctttttac ggttcctggc    240
cttttgctgg cctttgctc acatgttctt tcctgcgtta tccctgatt ctgtggataa    300 ccgtattacc gcctttgagt gagctgatac cgctcgccgc agccgaacga ccgagcgcag    360
cgagtcagtg agcgaggaag cggaagagcg cccaatacgc aaaccgcctc tccccgcgcg    420
ttggccgatt cattaatgca gctggcacga caggtttccc gactggaaag cgggcagtga    480
gcgcaacgca attaatgtga gttagctcac tcattaggca ccccaggctt tacactttat    540
gcttccggct cgtatgttgt gtggaattgt gagcggataa caatttcaca caggaaacag    600
ctatgaccat gattacgcca agctatttag gtgacgcgtt agaatactca agctatgcat    660
caagcttggt accgagctcg gatccactag taacggccgc cagtgtgctg gaattcgccc    720
ttatcacctc tttccaaaac aaaagtatat ccaatatatt ccagaactag aaattccttt    780
ttcatctatt atcttctcct cctccttaga gaaggagaaa aatggtggaa agtgaaaaaa    840
tgaatgaaac aaagaagttg agcaagagct attttgatgt tttgggaatt tgctgtactt    900
cagaagttgt tctagttgaa aaaattctca gaatcttga aggggttaaa gaggtttcag    960
taattgtcac aacaaagact gtcattgtta ttcatgattc tcttctcatt tctccgcaac   1020
aaattggtaa gaaagatagt tacacacctt tattactctc tcagttctat tttttacgtg   1080
atactatttt ctttttaata tgttctgaaa agaacgttac cttttatat attgatgtaa   1140 tttcacttta aacttcatat ttttttttctt aaatagtatt gttttatagt cataaaata   1200 ttattataag tctttcttaa gttttgtggc ttgttaaata aattcacata aaatgaaata   1260
aagcggtagg agtaccattc ttcatctttt cttaattaac tgacatttcc tttctttttt   1320
gtaagtttat atatattaag taaagtgatt tttctcttaa gaaatcgcca aaaaaaaaaa   1380
ggaaagagaa gagaagagac aagaagggg agacaaatgg aatcagaaac ggttttgatt   1440
tgttcaagtg atatttggtg gtagttgttt caagcactgt tctttctgtt tgttggcatt   1500
tgctagaatt aagtgtatat attaatttgg gaaaatcttt aaagtggtta ttttttagttt   1560 tattagattg agtaaccaag acggaaaaaa catgaactat ttttcttttg aaatttctag   1620
tcaagaacat gcataaaaat tctcttttaa aacgactctc ataaaaattc atgtggtcga   1680
gtttacgcag cacatggacc catagtctcc gcctaactaa gtattttaag tatgtatttt   1740
ctaaaattca tctaatattt tctgttggcg cacatgctcc acaaaagatg aattgtgcat   1800
ttgtttgaat attgagttat tactcaaagg aatatggatc aattccactt ttttttctctt   1860 ttctttaata ttgtacccat atcttaaaaa ttctagctcc gcctccgact tgcccatcgt   1920
atccgcccca gccctcagtg ggatagagta ggtgaggagt atagtttata aatgttttt   1980 ctctaacaat taggttttgg aataaattct gagattcaat ggtctatttg aaacctgtaa   2040
ttactactcc ctccgtttca tattagatga ttactttcct ttttagtcta ttccaaaaca   2100
aataacacat ttctaaattt ggaaataatt caattttaaa atctttcatt ttacccattt   2160
accttaatga atgttttat agccacacaa atgtcatgac cccacaaatt ttttaccct   2220 taaacttttta agaccacaaa ttttaaaagt ttcttctttt ttcttaaact atatgccaag   2280
taaaactaac tcatcttgaa acggaggagt actataagaa tagttatata tgatttggcc   2340
```

```
ccacaaatta cataattgtg gcaagaaatc caagtttcta gttgttgata atttagtgat   2400
ggaggcgatc tctgttgaac cgttagagaa atatttttga ctcatgtcgc tttgcatcta   2460
ctgtgttgaa gagtagttgc taggaactaa caaagtaatt gtagtttcct tgttttttt    2520 ttttccttc  ttgatgaatt actgtacttt attttcccat ttttttaacg tctgttactt   2580
atggtcagtt ttcaagtgtg aaaaattagc cagaaagaat aattcaacaa acttaacctt   2640
ttcttttctt cattcttgcg atctttccta aatatattta gtagagtctc ttttctactt   2700
cagtcttatt gcatttcttg cacacctaac agtagtggta cataaattgg acctagctaa   2760
caaaaggtaa ctcttatctg caagtttaat tggtacagta acatgaaact tgttataatc   2820
ttttaaattg cagccgataa tatatgtatg ttttacattg gttgtgtgta tataatgtaa   2880
attctttaca gcatgtttga ctaacctgca aaaattagtt ttttttttt  caaaagtatt   2940 tttggtgaga agcagtttgt gtttggctaa gtaatttgaa aaatacttct gagcaacaat   3000
tagtgtttgt ccaagctttt aaaaactgct tttaattgta ttttttgtcaa aagagctttt  3060 taaaaagta ttttttagag agaaactact tttttctgct tctccaaaat tgtttctgct    3120
tctcctcaaa aacactttt ttccttctaa aagcttgtac aaacacttca actaaaaaaa    3180
atatattagc acttatatta tccttataat tattgaagtt accatctatc ttttgtggat   3240
gtagttaaag cattgaatca agcaagatta gaagcaagca taagagtgaa aggagagaaa   3300
aactaccaaa agaaatggcc aagtccattt gcaattggca gtgaaatatt gcttggactc   3360
tcatctttga agtactttt  tgcaccttc  caatggttag cacttgcagc tgttgcagtt   3420
gggattcctc caattatttt tagaggtgtg gctgccgtgc gaaacctcac tcttgacatc   3480
gacattcttg ttttaatagc aggtactttg cttttccttt tctttctttt taacttttg    3540 aaaagcaaaa agagatactc ccttttgtcc caatttatat ggcggtattt aattaaacaa   3600
aaaaatctaa gaaaaatatg aatactttaa aaatttatgg tttgaaataa atcttaggca   3660
tctaaataca aggttaaaat aataatttta aagttaaaaa attcaagaaa gaaggaaga    3720 cttctaaaat ttgtggcaag aaataaatct tagagatttg tgttataaat catctcacta   3780
aggctaaaat aataattta  aagttaaatt acttttaatt atgaaaaggt gatagatttt   3840
tgggaaaaga tagaaaagaa aactgtgcta tataaattga gacagagaga gtaatttacc   3900
ataagagtat ttgaagttga tttggttata gaattaacat gtgctcctac tttagctttg   3960
tgattgaaat ttggctattg ctttaatttc ttagctaatt ggatgcttct aatgtgatgc   4020
ttgaatcctt attcttgata atgctttgtg attcattatt tcattaaaaa gcatgcacca   4080
tagggcatgc aattaaatat tgtatttaag aatgcacttt taactaaccc acaagattgg   4140
agtgggaggg atgattcttg ggtgttagat gctaatattg gaccaccta  gtgactttaa   4200 ataacgaaag catgaaaaac aattattgga tgcttgatat actttatgtt ataatatttt   4260
caggtgacct agaactacac aaataaaactt cttttttccat attggaatag gatgatttag   4320
atttcaagat ggaattagtg attctatcac agattatctt ttatttaatg atatcaaata   4380
tgaaaagaga aaaaaaaaag gtgtctagga aatagtcaga agatagtat  gacatatatt   4440 attgatacaa attaatcagc tcaacacaaa ggctagcata tatttaacaa atagttatag   4500
acttgtagtg ttgtaccttt agttaagaga ctaaacacta ccaaaaggtt gcgatggagc   4560
agtaggtact cctctattgt catccaggcg ccttgatata aattaattag atcccaaaac   4620
gaggatcaga taccaaataa aaaacaaaaa gaaactatct ttagtgtttg ttgatttaca   4680
tggcgtagaa aaataaagga caatataata aaaaccttgg aatatcagtt aagatgcctt   4740
```

```
aatttcaaat cagtggagta tattccgact tccgtattaa tttcgctcta atcaagtctt    4800
ttaaaagatt aaataatgaa aagttttat agtcacgaaa acattatgac cacaaaattt    4860
tgtcctttaa gcttttaga ccataaattt caaaaaaaaa aatttgactg aaatatttaa    4920
taccacatat ttttaaaaaa ttatttttt cttacattta gtgtcaagta aaattagatg    4980
tgataggaaa aaagaatttc gatttcgtct agtaaggaaa gtacaaaatt gcttatgtaa    5040
ctcgtaatat atcagaaatg gtttcccagg tgtaaagcac aaacaacgga gcccacatca    5100
gtaatgtgta aatgtgtaac gtttactctc ttttttttcct caaataattg caaagaaaat    5160
gactttcctg caagtctttc ttgcccctt tatagaaggt gacgttgact cgtaccagat    5220
tttcttgtca tagtattaat cagtagtaat atcagtcacg gcgaggttta aaatttagtc    5280
tattagtaac gtaaataatt tttaaattgt catatttagt taatctaaaa tatcatgcaa    5340 tttttatat caagtttgat atgttgacgt aaataataga acaataattt ataaacttga    5400
ttaaattgca ttgataataa atcaaaatat tatttgaacg attaaaatct cacagttaat    5460
tttgcatctt gcataaaaaa atatccatca tatttccttg attatcattt gatgccgtct    5520
tagtttcttt taaaaaaatt tagaatttat atcaaatatg atttttaat tactcgaact    5580 tacaagcaga ctaagtttga tattttccta attcaacgat atacggttac tacggaaggc    5640
atttactaga aatactctga gatgttactg caattattat tattattatt ttaaaaagag    5700 aaaaaataa cttttaaagc tccatgtgaa attatgtata tttattata gcatgaagtg    5760 acccattttt ttatctcata aataacattg atcccatatt tttctactgt atcatcacta    5820
tcatgaaaaa tacatctaga ttactgagat gtttattggc agtagtatct acagatacaa    5880
cagatgcttc tagttctatt gatgttttca ttttgacaaa aatttaattg agaaagcaaa    5940
agattttgca agaattctta gggttttatt caaaaaaaaa aaagaattct tagaaatata    6000
agttttggca attaaataat tccagtaatt gggaaaaaac acttgaatag gctatagaag    6060 taaagaaac ttctatatat taccaggcag cagagtttcc caaaatcctt ttttctaaaa    6120
aaaaaatagt agaaaatgag caatgtaatt tctttaagta acattctcta tttagtaaaa    6180
tgtccatttt tctaatgagg taaaagcaat agcaaataaa agaaagttta ttccttttt    6240 tcgagggtgt tgccgaccaa ggcttaaata gataggaata atcacctaat taagaaaaac    6300
tacctatcaa ttttttgtctc ggttggattt caacatgata cctcatagtt ctacgtacgc    6360
ccacttcaat taccactagg aacaccgttt ggtgcaggaa aattttggtc ataaacttca    6420
attttaagcc ttcatataaa caataaaaga gctaattagc agttaacagt cgagttaata    6480
tagctgaata atgcagttca actaaatatg tatggaaatg gtgaaaagca caaaggtgac    6540
ttatccttag gtactttata gctttatctt ttaaaaagta gtagcaagat atgatatgat    6600
tccttgaaga agaaaaggtc actgtgactc tttatttcta tcagtacctg tttgaataaa    6660
attggctaag aaagttgtaa aatggactag caggacaaga atctcaattt ggtgttgctt    6720
taccatcttt agagtgacag caatcaaaaa cccaaaaatt aaataaataa taagaaaaga    6780 aaagatgag ttattggaaa gggtaaaatg aatgaagata agaatactcc attcagtcca    6840
aaatattaag ctagcatttg gacatagatt tggttgaagc ttgaagaaaa gaaaaaagag    6900
tttttgaaga ttatatgaaa aataattttt gaaagttaaa aattgtgttag ggaagttttg    6960 tgattcaaaa actactctag aactgttttt gggatttaaa tattttcttt tcaacatgtg    7020
ccaaaaaatg attaaaatct ataaacgaac acataattga aaaaagctct caaattttat    7080
gaccaaacag gagcttattg ttttggcaaa ttgaatttgt ttcgaaatac ttgatgatta    7140
```

```
aggagagaca aaggatagta tagacaaaag gctattagta tttgtaattg aggctattaa   7200
atgtcttttt aaagcgatgt gcaaaaacct taaaaaagac gaattatatg gattatatta   7260
gaagtagtat taaattttaa tggaacttag tgcaatcatt ttacaagggc atagtgttaa   7320
agctagaaat gctgattctt atagctggct ttgtcatgtg cagtggctgg atcaattgtt   7380
ttacacgatt attgggaagc tggtactatt gtcttcttat tcgccattgc agaatggcta   7440
gagtcaaggg caagtcacaa ggtttgtgaa ttttcgtccc tgtttaattt ccttgcacaa   7500
gaaatggcta gtgtacatct actttcctag gatgacagta atgtgtgttt tttttattta   7560
ttgtgatacc aaaagtatga acacctaatt tttctcagga tacatatttt ccactttggc   7620
caaactgact ttaacaagtt gtctcttgga ttacgccaca tcgaacctaa aagtgttggc   7680
actaccatgt caacttgtgc tgtcttatag ggatttgaga cattttgtct agggtgtcat   7740
atggacccct tcttcatgag ctcgatagca caaaagcttg ctagtcattc tacttgacct   7800
gcctcattag cccgccctac gcatgggcat cacaaaccag gccacacgta ggaattgagt   7860
ctcctccctg cggttcaccc acagaccttg cagttttgtc gcttgggtaa tgccacaact   7920
agcccgataa cgtgcttacc atgtgaactt gtaccatata ttacctagca cttcaccttc   7980
ctctcccttt gcgacgcgcc taaaatgtca tatgcaccgt ttttccgaa gtttgctagt   8040 ctagaagcct attagttctt aggcttaacc tgcctcatta accactctcc atcataggcg   8100
tcaccttaat ttaaaagaat tgttcttag aaggctctaa cttaaccag aaatcagttc   8160 agctgtcttc tgttctttta cctcaataac attgtataat ggtaaggact aaactgcagc   8220
tctcttgtgg atgagtggat taaatttcat tctgaaaatt aatttacttc acagctctat   8280
ttggagaaaa taagattaa atattgtgag aatgcacggg agaaaaatat tatattgatt   8340
aaagtgttgt acaaccctat ttatatacag taattatata ataatatgta tctacttccc   8400
gatgtgggac actaaatatg actaactact taacacttcc tctcaagccg gtgcatataa   8460
atcatacgta ccgagcttgt tacagatgta accaatacga gaaccagtaa gagacttagt   8520
gaaaatattt gctagctaat cattcgactt tacaaacttt gtaacaatat ctcctgagag   8580
tatcttttct ctgacaaagt gacagtcgat ctcaatgtgt ttagtcctct catggaatac   8640
cggatttgac gcaatatgaa gagcagcttg attatcacac accagttcca tcttattgat   8700
ttctccgaat ttcaactcct tgagcaactg cttgatccac actagctcac acgttgccat   8760
agccatggcc cgatattcgg cttcggtgct agatcgagca actacattct gtttcttgct   8820
cttccaagag accaaattac ctcctactag aacacaatat ccagacgtag aacgtttatc   8880
agaaggtgat cctgcccaat cagcatttgt gtaccctgta atctgctcgt agcctcgatc   8940
ctcgaatagt aacccttttgc ctggagctga ctttatatat cgaagaatgc gaacaactgc   9000
atcccagtga ctatcacagg gagaatccat aaactgactt acaacactca ccggaaaaga   9060
aatgtctggt ttagtcaccg tgaggtaatt caatttgcca accaacctcc gatatctcat   9120
aggatctcta agaggctccc cctgtccatt gcagaagctt agcattcgga tccataggag   9180
tgtcaacagg tctacatccc atcattccag tcttctcaag aatgtctaag gcatacttcc   9240
gctgtgaaat aacaatacct gagctagact gagcgacctc aatacctgga aaatacttca   9300
atctgcctag atccttagtc tggaagtgcc aaaagagatg ttgcttcaga ttagtaatac   9360
catcctgatc attgtcagta ataacaatat cgtctacata aaccaccata gtaaggttat   9420
gaacaaaaca cgtgcttcta aagacacggg gtggaagaga gaacaaaggt aagtggggaa   9480
acaggacaga gaatggaact tgattctgga tagctgaaga tgacatacga ttaataagat   9540
```

```
agcaagatgt aagaactgca tcaccccaaa aatgcaacgg agcatgagat tgtatgagta    9600
gagtacgagt agtttcaata agatgtctac tctttctttc agctacccca ttttgttgag    9660
atgtgtacgg acaagatgtt tgatgaataa tcccatgaga gttcataaac ttctgaaatg    9720
gggaagacaa atactctagg gcattatcac tacgaaatgt gcggatagaa accccaaatt    9780
gattttgaat ttcagcgtgg aaggtctgaa aaatagaaaa tagctcagac cgattttttca   9840 tcaaaaatat ccaagtgcac ctggaataat catcaatgaa actgacaaag tagcggaatc    9900
ccaaggtaga actgacccga ctaggacccc aaacatctga atggaccaaa gtaaaaggtg    9960
acgctgaggg aaatgggagt gggtatactt accgagctgt catgactcat actctagagt   10020
ggacaagtga gataaaccag gtatcatttt ctaaagtttt gacaaactgg gatgtcccaa    10080
ccgtttatgt aataaatctg gtgaatcggt aacaagacaa gttattaaag gaagacaaga    10140
tgcgagtcca tatgattttg caaggataag gtaataaaat ccatctaatt catgtctgat    10200
accaatgatc cgccccgtac tatgtttctc tataaaaata aggtcatcaa gaaataaaac    10260
agcgcattta agtgatttgg ctaagcgact aacggctatg agattaaaag gactattggg    10320
aacataaagg actgaatcta aaggtgagga aggaagtggg cctgcttgac ctattgcagt    10380
tgccatggtt tgagactcat tggccattgt gactgttaga agagattgag aatatgaata    10440
ctggtgaaaa gagatttgtt accagaaata tgatcagatg catttgaatc aatgacccaa    10500
gactcaaagg tttaagattc ggagacacaa gtcacgctac tatctgtttg aacaatggaa    10560
gctatccctg aagatgtctg tttacatgct ttgtactgaa ggaactcagt ataatccgat    10620
aaagaaacca tctggattgg attcaacgaa ttggatccaa cagattgtga gttaaaggct    10680
tctgatacga atgtcattat aatgttgtgc cgaaaaaaca aaaaattcct ggaaattact    10740
attcacgccg gaaaaatata aaagtgatct gaatttgatt taaattggat gggtatgctc    10800
gtatttgcaa ggagaagaca ctgccctgaa ggaattttac caaattctgg ccggaaattg    10860
cctcatgtgc ggcgtgtggg cgtcagaact tcgtcggaaa aattcttccg gcggcgcgtg    10920
agggcgcgtg tagcctttt tgccagagat ttttttaatag gttggtcgct gagctctgaa    10980
ctacttcccg gtggtgttac cttttgcaca acactgacag atagtatgat tcttgcggac    11040 agacctatt ttgccggaaa agagcttccg gttgactgtt ttcttttccc ggagtcgctg     11100
gaatttatgc actacgataa atttctcacg gttgctctga taccatgtga gaatgcacgg    11160
gagaaaatta ttatattgat taaagtattg tacaacccta tttatataca gtaattacat    11220
aataataggt atctacttcc cgatgtggga cactaaacat gactaactac ttaacaaata    11280
tggtattgga atttagtctc tttgacataa acgacataag cctatgctta tcttttctta    11340
cttttttagc aatgctaaat agtaggtcct aactacaaac tttatagcac actgaaaatt    11400
accaaaatat agagatggcc aatgaaggtt ttgtctgcta acataactct gtgtctttat    11460
tttctcactg atattgtata tggataaagc attctgataa atgaaaacct ttatggttat    11520
gtaggctacc gccgctatgt catcactggt caatatagtc cctccaacag cagttttagc    11580
ggaaagcgga gaagtcgtaa atgttgatga agtcaaggtg aatagcattc ttgctgtgaa    11640
agctggtgaa actatacctt tgatggagt tgtagtggaa ggggaatgtg acgtggacga     11700
gaaaacactg acaggcgagt cgtttccagt ttctaagcaa agagattcaa cggtctgggc    11760
tggcgctaca aatctaaatg gtagtatagt atttcttcat gcttcattta tttagtgctg    11820
aaacttcaag tattgtttgt taatgttatt tgctcaattc ttcaggctat atcagtgtta    11880
agactacggc tttggctgaa gattgtgcgg tggctaggat ggcacagcct gtcgaagatg    11940
```

```
ctcagaacaa gaaatcaaaa acccaaagat acatcgacaa gtgtgctaaa tattatacac    12000
caggctagtg aatcttatgt tgtgccacat caagtcaaaa aatgcacgta ccgtgtgaac    12060
ttgttctttg tcttatgaat cacgtcacta tcctctccct tttcgatatg agatttccct    12120
aaggtgtcat atgaatccct tcttcggaag cttgccagca taggagtcta tcagtccttt    12180
cacttgaccc gccctctcag cctgcctgca gtcatgggcg tcgcactact atattgctct    12240
ttcgtttaaa acttttatt tctaatactt ccctgctctt tgtgtatgtc taatttcgac    12300
tggtgatgtt ttgcagcaat tgtggctata ccagcttctt tggcaattgt tcctactgca    12360
ttaagagttc acaatcgaaa tgaatggtat cgcttggctt tggtcacatt ggtgagtgca    12420
tgtccgtgtg cactcgttct atctacacca gttgccatgt gttgcgcact ttcaaaagca    12480
gcaacgtccg gtcttctgtt taaaggagca gagtaccttg agactctagc taaaatcaaa    12540
atcatggctt ttgacaaaac agggactata actaaaggag aatttatggt gaccgagttc    12600
aagtctctga ttgatggttt tagtctcaat acactgcttt actggtaaag gttaccactc    12660
atacatattc ttttatgttg ccaaagagaa ttcaaaatct taactggtta tctttcacgg    12720
cacattgata gcgatataac atgattgatt tatatcatat attcataaaa gatgaaaatag   12780 ggagtgccac attcacattc tcatattgaa gtttctgaaa tggctctaat ggttcaccat    12840
agagccaaaa taacatatag acacaacgtc agccgtctga tattcaggaa cttagatgga    12900
atagttggat cttatacatt gaggacacat aaaagtactt ggtcatataa attttagaaa    12960
tataatcaat gtattataat ctaaaattct tcaaatattc ttgatactgc aatacaaaag    13020
cacatggcac actgaataga agccttgttc ggtggtctaa acattcgtt tagagtaaat    13080 actgagttgt ctagtgaata ttttcagggt ttcaagcatt gagagcaagt caggtcatcc    13140
gatggcaacc gctctggtgg actatgcaca atcaaattcc gttgagccaa agcctgatag    13200
agttgagcgg tttcaaaatt ttcctggtga agggatattt ggaagaattg atggaatgga    13260
aatctatgtc gggaatagga aaatttcttc aagagctgga tgtaccacag gtaaatggtt    13320
gaatcatttc ttatgctcat agtagagata aaacatcaga gttataatta taagtatatg    13380
atttctccag ttaattttgc tgttagattt tctttgacct gtttagcact aatgcggtgg    13440
atgtttgaat tcagtacca gaaatagagg gtgatagttt caaggaaag tctgttggat     13500 acatatttt gggatcatct ccagctggaa ttttcagtct ttccgatgtt tgtcgaattg    13560
gtgtaaaaga agcaatgaga gaactgaagc agatgggtat caaaaccgcg atgcttactg    13620
gtgatcgtta tgcagctgcc aaccatgtgc aggatcaggt atattaataa ttctgcatta    13680
cgctgaaatg attataaaac cctttggatt attgtttagt cttaagaatt ttcactgaac    13740
tcttattgtt tccttcttct atcatcaaca ttggttaaac atttcatcta aatttagaga    13800
acgtatcacc aagtaagtgc tttacctta cagggtcata taaaatactt aagacagtgt    13860
gatgtgaaga tgaaggttaa atgttgatct ggataaacca agttattatc acaactaata    13920
taagatatgc tattgttctc caataattgg acgattttcg gacgtacgac gtacaattct    13980
tcacatatga aacctacatc agacgtacat gacacgctat gtttagcata aagagtcaag    14040
attagcatga tgatttaagc tgaatctgaa tttcaagtat ctattcttgt attgtaccca    14100
ggggcggaac tagtgttgtg cttagaggtc tcaaacattg tatttgtgtt aaaaaattca    14160
cttcatatgt atttaaataa tttatccaga gcagtgagcc atatttttta gaatccagaa    14220
cccataaact caaatcata gatccacctc tgattgtaag tcggaacaat tatgcagtta    14280
ggtggagctt tggatgaatt tcaagcagaa ctcctaccag aggacaaggc aacaatcatc    14340
```

```
aagggttttc agaaggaagc tccaacagcg atgataggcg acggccttaa tgatgctcct    14400
gcattagcaa cagctgacat tggcatctca atgggcatct ctgggtcagc tctcgctaaa    14460
gaaacaggcc atgctatact aatgacaaat gacatcggaa gaataccgaa agctgcacgt    14520
cttgctagaa gagttcgaag gaagattgtt gagaatatga ttatatcagc cgttacaaag    14580
gctgccatag ttgcattggc aatagcaggt tatccattgg tttgggctgc tgtcctcgca    14640
gatactggga catgcttgct agtgattttg aacagcatgc tacttctacg aggaggcaca    14700
cgcagacatg ggaaaaaatg ttggagatct tctactcctt cgcatgctcc ccaccacaaa    14760
gacaaagctt catgttgcaa gtcggaaaat gctccccagc tgtgttgctc tgatattgag    14820
tcacaaaaga aatgtacaag tcaatcatgc tcgtccgagg tgtgtgttcc aagatgtcaa    14880
cctgtctcct cgggatcaaa gtcatgtgga aataatcagt gcccagactc cattgaaaat    14940
agtggttttc attctcatcg ccgtcctcaa tgctgctcgt cgaagatggc tgctaaagca    15000
tgccaatctg cagtttcaga atcaaagtca tgcggaaata atcagtgccc agactccgtt    15060
gaaaatagtg gttttcattc tcatccccgt cctgaatgct gctcgtcgaa gatggctgct    15120
aaagcgtgcc aatctgcagt ttcagaatca aagtcatgtg gaataatcag tgcccagac    15180 tccgttggaa atagtggttt tcattctcat ccccgtcctc aatgctgttc atcgaagatg    15240
gctgctaaag caggccaatc tgcactttca gaatcaaagt catgtggaaa taacaattgc    15300
tcagactcca ttcacaagag taattgtcat tctttaacta actctctagt atgttcttcc    15360
aagatgtctg ctccacaatg tcattctgct acttcaagca caaatcatg tggaagtacc    15420 aagtgctccg acttcagtga taaaaaatgt tgtcaatccg acaaaattcc tcaagcgtgc    15480
tctaccaaga agtctgctcc agggtgtcaa tctgcagttt ctgggtctaa atcatgtgga    15540
aatagcaagt gttcagactc aaaagacaat agtagccatc cttcacatcc cgatcatcaa    15600
acatgcatgt ctaagttgtg tgctccacaa agccaatctg caacttcaag ctccaggaca    15660
tgtggaaata caaagtgctc ggacaccaat agcaagaatt cttgttattc acaaaccaac    15720
tctgaatcat gctcttcaaa gatgtctggt ccatcatgca aaactgctaa ttcaggtacg    15780
accagattcc tcttcttgtt aatacccccc gaaccaaact ataggatcta aagtattatt    15840
tggccctctg tcggaggata taatggttag ttaaacctga aatcatgtag tctatgaatt    15900
gcaaatctct agcatcgtga caaaattctt agatcatata caactttgag aatataggct    15960
gtcacagacc cttcttcata ctgcattaga ggagagcagc caatttttta ttcatgattt    16020
gaaacaaata aagttcttct tgaggtgtat ggagaggcta tgagaatcat ttgctgagta    16080
ggtttgagat tttcaggttc aaggtcatgc agaaataaga agtgccagga ctctgcaacc    16140
gagaacagtt tcattcacc acttactaat ccactcagtg gggaaaagct ttcggagcag    16200
aaaagcttgg atttagtccg aaaagataag gaatcaagtc atgatcttcg tcatggctgc    16260
tctgacgagg aacatgatca tacaaattta gacaaggcat atgacagttg tgccttacaa    16320
gaatgttgtt attcggttca aggcaataaa actgatgtat cagaaactgg aatccaggaa    16380
actgctcatt gtgacagcac caatcaaaca tgccaaactg caagttcagg taggcactac    16440
caaatcatat gatccaaagt gctcctccac cttcactcct acaataaatg ttcgatcaaa    16500
cttcataaga agatagcata tgcatcgcaa atctctaaaa aaatgatgga taatgttact    16560
caccaactag tttgagatag aagtttaact gattgctata tatcgttaac tataaaaaac    16620
tacttgttaa ttagagctga gattttcagg atcgatgaca tgcggaaatg ataagatcct    16680
ggactctcta agcatccatg gttgtcattc gcatgataat ccactccacg aggagaacaa    16740
```

-continued

```
cctggagcag aaaatcttgg atgttgttgg agaaggtata aaatcacctc atgctgtcgg    16800
tcatggctgt tcggacaagg aacacgatca ctcacatcca gaaaaggcat atgacagttg    16860
tgcaacagat gattgttgtt tttcagttca agtccatggc attgacgacg tatcaaaaag    16920
tgaaattcaa gaaactgctc attgtgacag cacaaagcag agcatggtca tctccagcag    16980
ctgcaaacat gaaccaaaag atcaggtaaa tcactgtgga cttcactcta aaactactcc    17040
aactgatgaa gaactagcca agctggttag aagatgctgc gaatacaaac catgccacga    17100
cgtccgttct ggctgcagga agcatgctgc agaatgtggt ccaaccgttc gatcaactat    17160
caatatctta cgggacaacc atcatcatta cctagactgc agtggtcgta aggtttgttc    17220
gctgttggag aagagacaca tcggtggatg ctgtgacagc ttcagaaaag aatgttgtgc    17280
caagaagaac caccttggag caagtttcgg aggaggttta tcagaaattg tcatagagta    17340
gatgcaatcc gaagtgtaca tatgttgtaa acttcctacc tatttttatct tcaagaagtt    17400
gagctgctaa tttgaacaaa gcaagggcga attctgcaga tatccatcac actggcggcc    17460
gctcgagcat gcatctagag ggcccaattc gccctatagt gagtcgtatt acaattcact    17520
ggccgtcgtt ttacaacgtc gtgactggga aaaccctggc gttacccaac ttaatcgcct    17580
tgcagcacat ccccctttcg ccagctggcg taatagcgaa gaggcccgca ccgatcgccc    17640
ttcccaacag ttgcgcagcc tatacgtacg gcagtttaag gtttacacct ataaaagaga    17700
gagccgttat cgtctgtttg tggatgtaca gagtgatatt attgacacgc ggggcgacg    17760
gatggtgatc ccctggcca gtgcacgtct gctgtcagat aaagtctccc gtgaacttta    17820
cccggtggtg catatcgggg atgaaagctg gcgcatgatg accaccgata tggccagtgt    17880
gccggtctcc gttatcgggg aagaagtggc tgatctcagc c                       17921
```

<210> SEQ ID NO 2
<211> LENGTH: 1397
<212> TYPE: PRT
<213> ORGANISM: Nicotiana tabacum

<400> SEQUENCE: 2

```
Met Asn Glu Thr Lys Lys Leu Ser Lys Ser Tyr Phe Asp Val Leu Gly
1               5                   10                  15

Ile Cys Cys Thr Ser Glu Val Val Leu Val Glu Lys Val Leu Lys Asn
            20                  25                  30

Leu Glu Gly Val Lys Glu Val Ser Val Ile Val Thr Thr Lys Thr Val
        35                  40                  45

Ile Val Ile His Asp Ser Leu Ile Ser Pro Gln Gln Ile Val Lys
    50                  55                  60

Ala Leu Asn Gln Ala Arg Leu Glu Ala Ser Ile Arg Val Lys Gly Glu
65                  70                  75                  80

Lys Asn Tyr Gln Lys Lys Trp Pro Ser Pro Phe Ala Ile Gly Ser Gly
                85                  90                  95

Ile Leu Leu Gly Leu Ser Phe Leu Lys Tyr Phe Phe Ala Pro Phe Gln
            100                 105                 110

Trp Leu Ala Leu Ala Ala Val Ala Val Gly Ile Pro Pro Ile Ile Phe
        115                 120                 125

Arg Gly Val Ala Ala Val Arg Asn Leu Thr Leu Asp Ile Asn Ile Leu
    130                 135                 140

Val Leu Ile Ala Val Ala Gly Ser Ile Val Leu His Asp Tyr Trp Glu
145                 150                 155                 160

Ala Gly Thr Ile Val Phe Leu Phe Ala Ile Ala Glu Trp Leu Glu Ser
                165                 170                 175
```

```
Arg Ala Ser His Lys Ala Thr Ala Ala Met Ser Ser Leu Val Asn Ile
            180                 185                 190

Val Pro Pro Thr Ala Val Leu Ala Glu Ser Gly Val Val Asn Val
        195                 200                 205

Asp Glu Val Lys Val Asn Ser Ile Leu Ala Val Lys Ala Gly Glu Thr
210                 215                 220

Ile Pro Ile Asp Gly Val Val Glu Gly Cys Asp Val Asp Glu
225                 230                 235                 240

Lys Thr Leu Thr Gly Glu Ser Phe Pro Val Ser Lys Gln Arg Asp Ser
                245                 250                 255

Thr Val Trp Ala Gly Thr Thr Asn Leu Asn Gly Tyr Ile Ser Val Lys
            260                 265                 270

Thr Thr Ala Leu Ala Glu Asp Cys Ala Val Ala Arg Met Ala Gln Leu
        275                 280                 285

Val Glu Asp Ala Gln Asn Lys Lys Ser Lys Thr Gln Arg Tyr Ile Asp
    290                 295                 300

Lys Cys Ala Lys Tyr Tyr Thr Pro Ala Ile Val Ala Ile Ser Ala Ser
305                 310                 315                 320

Leu Ala Ile Val Pro Thr Ala Leu Arg Val His Asn Arg Asn Glu Trp
                325                 330                 335

Tyr Arg Leu Ala Leu Val Thr Leu Val Ser Ala Cys Pro Cys Ala Leu
            340                 345                 350

Val Leu Ser Thr Pro Val Ala Met Cys Cys Ala Leu Ser Lys Ala Ala
        355                 360                 365

Thr Ser Gly Leu Leu Phe Lys Gly Ala Glu Tyr Leu Glu Thr Leu Ala
    370                 375                 380

Lys Ile Lys Ile Met Ala Phe Asp Lys Thr Gly Thr Ile Thr Lys Gly
385                 390                 395                 400

Glu Phe Met Val Thr Glu Phe Lys Ser Leu Ile Asp Gly Phe Ser Leu
                405                 410                 415

Asn Thr Leu Leu Tyr Trp Val Ser Ser Ile Glu Ser Lys Ser Gly His
            420                 425                 430

Pro Met Ala Ala Ala Leu Val Asp Tyr Ala Gln Ser Asn Ser Val Glu
        435                 440                 445

Pro Lys Pro Asp Arg Val Glu Gln Phe Gln Asn Phe Pro Gly Glu Gly
    450                 455                 460

Ile Phe Gly Arg Ile Asp Gly Met Glu Ile Tyr Val Gly Asn Arg Lys
465                 470                 475                 480

Ile Ser Ser Arg Ala Gly Cys Thr Thr Val Pro Glu Ile Glu Gly Asp
                485                 490                 495

Ser Phe Lys Gly Lys Ser Val Gly Tyr Ile Phe Leu Gly Ser Ser Pro
            500                 505                 510

Ala Gly Ile Phe Ser Leu Ser Asp Val Cys Arg Ile Gly Val Lys Glu
        515                 520                 525

Ala Met Arg Glu Leu Lys Gln Met Gly Ile Lys Thr Ala Met Leu Thr
    530                 535                 540

Gly Asp Cys Tyr Ala Ala Ala Asn His Val Gln Asp Gln Leu Gly Gly
545                 550                 555                 560

Ala Leu Asp Glu Phe Gln Ala Glu Leu Leu Pro Glu Asp Lys Ala Thr
                565                 570                 575

Ile Ile Lys Gly Phe Gln Lys Glu Ala Pro Thr Ala Met Ile Gly Asp
            580                 585                 590

Gly Leu Asn Asp Ala Pro Ala Leu Ala Thr Ala Asp Ile Gly Ile Ser
```

```
                595                 600                 605
    Met Gly Ile Ser Gly Ser Ala Leu Ala Lys Glu Thr Gly His Val Ile
    610                 615                 620
Leu Met Thr Asn Asp Ile Gly Arg Ile Pro Lys Ala Ala Arg Leu Ala
625                 630                 635                 640
Arg Arg Val Arg Arg Lys Ile Val Glu Asn Met Ile Ile Ser Val Val
                645                 650                 655
Thr Lys Ala Ala Ile Val Ala Leu Ala Ile Ala Gly Tyr Pro Leu Val
                660                 665                 670
Trp Ala Ala Val Leu Ala Asp Thr Gly Thr Cys Leu Leu Val Ile Leu
            675                 680                 685
Asn Ser Met Leu Leu Arg Gly Gly Thr Arg His Gly Lys Lys
            690                 695                 700
Cys Trp Arg Ser Ser Thr Pro Ser His Ala Pro Thr Thr Lys Thr Lys
705                 710                 715                 720
Leu His Val Ala Ser Arg Lys Met Leu Pro Ser Cys Val Ala Leu Ile
                725                 730                 735
Leu Ser His Lys Arg Asn Val Gln Val Asn His Ala Arg Pro Arg Cys
                740                 745                 750
Val Phe Gln Asp Val Asn Leu Ser Pro Gln Asp Gln Ser His Val Glu
            755                 760                 765
Ile Ile Ser Ala Gln Thr Pro Leu Lys Ile Val Phe Ile Leu Ile
            770                 775                 780
Ala Val Leu Asn Ala Ala Arg Arg Arg Trp Leu Leu Lys His Ala Asn
785                 790                 795                 800
Leu Gln Phe Gln Asn Gln Ser Arg Ala Glu Ile Ile Ser Ala Gln Thr
                805                 810                 815
Pro Leu Lys Ile Val Val Phe Ile Leu Ile Pro Val Leu Asn Ala Ala
                820                 825                 830
Arg Arg Arg Trp Leu Leu Lys Arg Ala Asn Leu Gln Phe Gln Asn Gln
                835                 840                 845
Ser His Val Glu Ile Ile Ser Ala Gln Thr Pro Leu Lys Asn Ser Gly
            850                 855                 860
Phe His Ser His Pro Arg Pro Gln Cys Cys Ser Ser Lys Met Ala Ala
865                 870                 875                 880
Lys Ala Gly Gln Ser Ala Leu Ser Glu Ser Lys Ser Cys Gly Asn Asn
                    885                 890                 895
Asn Cys Ser Asp Ser Ile His Lys Ser Asn Cys His Ser Leu Thr Asn
                900                 905                 910
Ser Leu Val Cys Ser Ser Lys Met Ser Ala Pro Gln Cys His Ser Ala
            915                 920                 925
Thr Ser Ser Asn Lys Ser Cys Gly Ser Thr Lys Cys Ser Asp Phe Ser
        930                 935                 940
Asp Lys Lys Cys Cys Gln Ser Asp Lys Ile Pro Gln Thr Cys Ser Thr
945                 950                 955                 960
Lys Lys Ser Ala Pro Gly Cys Gln Ser Ala Val Ser Gly Ser Lys Ser
                965                 970                 975
Cys Gly Asn Ser Lys Cys Ser Asp Ser Lys Asp Asn Ser Ser His Pro
            980                 985                 990
Ser His Pro Asp His Gln Thr Cys  Met Ser Lys Leu Cys  Ala Pro Gln
        995                 1000                1005
Ser Gln  Ser Ala Thr Ser Ser  Ser Arg Thr Cys Gly  Asn Thr Lys
    1010                1015                1020
```

```
Cys Ser Asp Thr Asn Ser Lys Asn Ser Cys Tyr Ser Gln Thr Asn
    1025                1030                1035

Ser Glu Ser Cys Ser Ser Lys Met Ser Gly Pro Ser Cys Lys Thr
    1040                1045                1050

Ala Asn Ser Gly Ser Arg Ser Cys Arg Asn Lys Lys Cys Gln Asp
    1055                1060                1065

Ser Ala Thr Glu Asn Ser Phe His Ser Pro Leu Thr Asn Pro Leu
    1070                1075                1080

Ser Gly Glu Lys Leu Ser Glu Gln Lys Ser Leu Asp Leu Val Arg
    1085                1090                1095

Lys Asp Lys Glu Ser Ser His Asp Leu Arg His Gly Cys Ser Asp
    1100                1105                1110

Glu Gly His Asp His Thr Asn Leu Asp Lys Ala Tyr Asp Ser Cys
    1115                1120                1125

Ala Leu Gln Glu Cys Cys Tyr Ser Val Gln Gly Asn Lys Thr Asp
    1130                1135                1140

Val Ser Glu Thr Gly Ile Gln Glu Thr Ala His Cys Asp Ser Thr
    1145                1150                1155

Asn Gln Thr Cys Gln Thr Ala Ser Ser Gly Ser Met Thr Cys Gly
    1160                1165                1170

Asn Asp Lys Ile Leu Asp Ser Leu Ser Ile His Gly Cys His Ser
    1175                1180                1185

His Asp Asn Pro Leu His Glu Glu Asn Asn Leu Glu Gln Lys Ile
    1190                1195                1200

Leu Asp Val Val Gly Glu Gly Ile Lys Ser Pro His Ala Val Gly
    1205                1210                1215

His Gly Cys Ser Asp Lys Glu His Asp His Ser His Pro Glu Lys
    1220                1225                1230

Ala Tyr Asp Ser Cys Ala Thr Asp Asp Cys Cys Phe Ser Val Gln
    1235                1240                1245

Val His Gly Ile Asp Asp Val Ser Lys Ser Glu Ile Gln Glu Thr
    1250                1255                1260

Ala His Cys Asp Ser Thr Lys Gln Ser Met Val Ile Ser Ser Ser
    1265                1270                1275

Cys Lys His Glu Pro Lys Asp Gln Val Asn His Cys Gly Leu His
    1280                1285                1290

Ser Lys Thr Thr Pro Thr Asp Glu Glu Leu Ala Lys Leu Val Arg
    1295                1300                1305

Arg Cys Cys Lys Tyr Lys Pro Cys His Asp Val Arg Ser Gly Cys
    1310                1315                1320

Arg Lys His Ala Ala Glu Cys Gly Pro Thr Val Arg Ser Thr Ile
    1325                1330                1335

Asn Ile Leu Arg Asp Asn His His His Tyr Leu Asp Cys Ser Gly
    1340                1345                1350

Arg Lys Val Cys Ser Leu Leu Glu Lys Arg His Ile Gly Gly Cys
    1355                1360                1365

Cys Asp Ser Phe Arg Lys Glu Cys Cys Ala Lys Lys Lys His Leu
    1370                1375                1380

Gly Ala Ser Phe Gly Gly Gly Leu Ser Glu Ile Val Ile Glu
    1385                1390                1395

<210> SEQ ID NO 3
<211> LENGTH: 4392
<212> TYPE: DNA
<213> ORGANISM: Nicotiana tabacum
```

```
<400> SEQUENCE: 3
tcacctcttt ccaaaacaaa agtatatcca atatattcca gaactagaaa ttccttttc      60 atctattatc ttctcctcct ccttagagaa ggagaaaaat ggtggaaagt gaaaaaatga    120
atgaaacaaa gaagttgagc aagagctatt ttgatgtttt gggaatttgc tgtacttcag    180
aagttgttct agttgaaaaa gttctcaaga atcttgaagg ggttaaagag gtttcagtaa    240
ttgtcacaac aaagactgtc attgttattc atgattctct tctcatttct ccgcaacaaa    300
ttgttaaagc attgaatcaa gcaagattag aagcaagcat aagagtgaaa ggagagaaaa    360
actaccaaaa gaaatggcca agtccatttg caattggcag tggaatattg cttggactct    420 cattttttgaa gtacttttt gcacctttcc aatggttagc acttgcagct gttgcagttg    480
ggattcctcc aattattttt agaggtgtgg ctgccgtgcg aaacctcact cttgacatca    540
acattcttgt tttaatagca gtggctggat caattgtttt acacgattat tgggaagctg    600
gtactattgt cttcttattc gccattgcag aatggctaga gtcaagggca agtcacaagg    660
ctaccgctgc tatgtcatca ctggtcaata tagtccctcc aacagcagtt ttagctgaaa    720
gcggagaagt cgtaaatgtt gatgaagtca aggtgaatag cattcttgct gtgaaagctg    780
gtgaaactat acctattgat ggagttgtag tggaagggga atgtgacgtg gacgagaaaa    840
cactgacagg cgagtcgttt ccagtttcta agcaaagaga ttcaacggtc tgggctggca    900
ctacaaatct aaatggctat atcagtgtta agactacggc tttggctgaa gattgtgcgg    960
tggctaggat ggcacagctt gtcgaagatg ctcagaacaa gaaatcaaaa acccaaagat   1020
acatcgacaa gtgtgctaaa tattatacac cagcaattgt ggctatatca gcttctttgg   1080
caattgttcc tactgcatta agagttcaca atcgaaatga atggtatcgc ttggctttgg   1140
tcacattggt gagtgcatgt ccgtgtgcac ttgttctatc tacaccagtt gccatgtgtt   1200
gcgcactttc aaaagcagca acgtccggtc ttctgtttaa aggagcagag taccttgaga   1260
ctctagctaa aatcaaaatc atggcttttg acaaaacagg gactataact aaaggagaat   1320
ttatggtgac cgagttcaag tctctgattg atggttttag tctcaataca ctgctttact   1380
gggtttcaag cattgagagc aagtcaggtc atccgatggc agccgctctg gtggactatg   1440
cacaatcaaa ttccgttgag ccaaagcctg atagagttga gcagtttcaa aattttcctg   1500
gtgaagggat atttggaaga attgatggaa tggaaatcta tgtcgggaat aggaaaattt   1560
cttcaagagc tggatgtacc acagtaccag aaatagaggg tgatagtttc aaaggaaagt   1620
ctgttggata catatttttg ggatcatctc cagctggaat tttcagtctt tccgatgttt   1680
gtcgaattgg tgtaaaagaa gcaatgagag aactgaagca gatgggtatc aaaaccgcga   1740
tgcttactgg tgattgttat gcagctgcca accatgtgca ggatcagtta ggtggagctt   1800
tggatgaatt tcaagcagaa ctcctaccag aggacaaggc aacaatcatc aagggttttc   1860
agaaggaagc tccaacagcg atgataggcg acggccttaa tgatgctcct gcattagcaa   1920
cagctgacat tggcatctca atgggcatct ctgggtcagc tctcgctaaa gaaacaggcc   1980
atgttatact aatgacaaat gacatcggaa gaataccgaa agctgcacgt cttgctagaa   2040
gagttcgaag gaagattgtt gagaatatga ttatatcagt cgttacaaag gctgccatag   2100
ttgcattggc aatagcaggt tatccattgg ttgggctgc tgtcctcgca gatactggga   2160
catgcttgct agtgattttg aacagcatgc tacttctacg aggaggcaca cgcagacatg   2220
ggaaaaaatg ttggagatct tctactcctt cgcatgctcc caccacaaag acaaagcttc   2280
atgttgcaag tcggaaaatg ctccccagct gtgttgctct gatattgagt cacaaaagaa   2340
```

```
atgtacaagt caatcatgct cgtccgaggt gtgtgttcca agatgtcaac ctgtctcctc    2400
aggatcaaag tcatgtggaa ataatcagtg cccagactcc attgaaaata gtggttttca    2460
ttctcatcgc cgtcctcaat gctgctcgtc gaagatggct gctaaagcat gccaatctgc    2520
agtttcagaa tcaaagtcgt gcggaaataa tcagtgccca gactccgttg aaaatagtgg    2580
ttttcattct catccccgtc ctgaatgctg ctcgtcgaag atggctgcta aagcgtgcca    2640
atctgcagtt tcagaatcaa agtcatgtgg aaataatcag tgcccagact ccgttgaaaa    2700
atagtggttt tcattctcat ccccgtcctc aatgctgttc atcgaagatg gctgctaaag    2760
caggccaatc tgcactttca gaatcaaagt catgtggaaa taacaattgc tcagactcca    2820
ttcacaagag taattgtcat tctttaacta actctctagt atgttcttcc aagatgtctg    2880
ctccacaatg tcattctgct acttcaagca acaaatcatg tggaagtacc aagtgctccg    2940
acttcagtga caaaaaatgt tgtcaatccg acaaaattcc tcaaacgtgc tctaccaaga    3000
agtctgctcc aggatgtcaa tctgcagttt ctgggtctaa atcatgtgga aatagcaagt    3060
gttcagactc aaaagacaat agtagccatc cttcacatcc cgatcatcaa acatgcatgt    3120
ctaagttgtg tgctccacaa agccaatctg caacttcaag ctccaggaca tgtggaaata    3180
caaagtgctc ggacaccaat agcaagaatt cttgttattc acaaaccaac tctgaatcat    3240
gctcttcaaa gatgtctggt ccatcatgca aaactgctaa ttcaggttca aggtcatgca    3300
gaaataagaa gtgccaggac tctgcaaccg agaacagttt tcattcacca cttactaatc    3360
cactcagtgg ggaaaagctt tcggagcaga aaagcttgga tttagtccga aaagataagg    3420
aatcaagtca tgatcttcgt catggctgct ctgacgaggg acatgatcat acaaatttag    3480
acaaggcata tgcagttgt gccttacaag aatgttgtta ttcggttcaa ggcaataaaa    3540
ctgatgtatc agaaactgga atccaggaaa ctgctcattg tgacagcacc aatcaaacat    3600
gccaaactgc aagttcagga tcgatgacat gcggaaatga taagatcctg gactctctaa    3660
gcatccatgg ttgtcattcg catgataatc cactccacga ggagaacaac ttggagcaga    3720
aaatcttgga tgttgttgga gaaggtataa aatcacctca tgctgtcggt catggctgtt    3780
cggacaagga acacgatcac tcacatccag aaaaggcata tgacagttgt gcaacagatg    3840
attgttgttt tcagttcaa gtccatggca ttgacgacgt atcaaaaagt gaaattcaag    3900
aaactgctca ttgtgacagc acaaagcaga gcatggtcat ctccagcagc tgcaaacatg    3960
aaccaaaaga tcaggtaaat cactgtggac ttcactctaa aactactcca actgatgaag    4020
aactagccaa gctggttaga agatgctgca aatacaaacc atgccacgac gtccgttctg    4080
gctgcaggaa gcatgctgca gaatgtggtc caaccgttcg atcaaccatc aatatcttac    4140
gggacaacca tcatcattac ctagactgca gtggtcgtaa ggtttgttcg ctgttggaga    4200
agagacacat cggtggatgc tgtgacagct tcagaaaaga atgttgtgcc aagaaaaaac    4260
accttggagc aagttttgga ggaggtttat cagaaattgt catagagtag atgcaatccg    4320
aagtgtacat atgttgtaaa cttcctacct attttatctt caagaagttg agctgctaat    4380
ttgaacaaag ca                                                       4392

<210> SEQ ID NO 4
<211> LENGTH: 723
<212> TYPE: DNA
<213> ORGANISM: Nicotiana tabacum
<220> FEATURE:
<221> NAME/KEY: Intron
<222> LOCATION: (1)..(723)
```

<400> SEQUENCE: 4

```
gcgtgagcta tgagaaagcg ccacgcttcc cgaagggaga aaggcggaca ggtatccggt      60
aagcggcagg gtcggaacag gagagcgcac gagggagctt ccaggggaa  acgcctggta     120
tctttatagt cctgtcgggt ttcgccacct ctgacttgag cgtcgatttt tgtgatgctc     180
gtcagggggg cggagcctat ggaaaaacgc cagcaacgcg gccttttac  ggttcctggc     240
cttttgctgg cctttgctc  acatgttctt tcctgcgtta tccctgatt  ctgtggataa     300
ccgtattacc gcctttgagt gagctgatac cgctcgccgc agccgaacga ccgagcgcag     360
cgagtcagtg agcgaggaag cggaagagcg cccaatacgc aaaccgcctc tccccgcgcg     420
ttggccgatt cattaatgca gctggcacga caggtttccc gactggaaag cgggcagtga     480
gcgcaacgca attaatgtga gttagctcac tcattaggca ccccaggctt tacactttat     540
gcttccggct cgtatgttgt gtggaattgt gagcggataa caatttcaca caggaaacag     600
ctatgaccat gattacgcca agctatttag gtgacgcgtt agaatactca agctatgcat     660
caagcttggt accgagctcg gatccactag taacggccgc cagtgtgctg gaattcgccc     720
tta                                                                  723
```

<210> SEQ ID NO 5
<211> LENGTH: 303
<212> TYPE: DNA
<213> ORGANISM: Nicotiana tabacum
<220> FEATURE:
<221> NAME/KEY: exon
<222> LOCATION: (1)..(303)

<400> SEQUENCE: 5

```
tca cct ctt tcc aaa aca aaa gta tat cca ata tat tcc aga act aga      48
Ser Pro Leu Ser Lys Thr Lys Val Tyr Pro Ile Tyr Ser Arg Thr Arg
1               5                   10                  15 aat tcc ttt ttc atc tat tat ctt ctc ctc ctc ctt aga gaa gga gaa      96
Asn Ser Phe Phe Ile Tyr Tyr Leu Leu Leu Leu Leu Arg Glu Gly Glu
            20                  25                  30 aaa tgg tgg aaa gtg aaa aaa tga atg aaa caa aga agt tga gca aga     144
Lys Trp Trp Lys Val Lys Lys     Met Lys Gln Arg Ser     Ala Arg
        35                          40                      45 gct att ttg atg ttt tgg gaa ttt gct gta ctt cag aag ttg ttc tag     192
Ala Ile Leu Met Phe Trp Glu Phe Ala Val Leu Gln Lys Leu Phe
        50                  55                  60 ttg aaa aaa ttc tca aga atc ttg aag ggg tta aag agg ttt cag taa     240
Leu Lys Lys Phe Ser Arg Ile Leu Lys Gly Leu Lys Arg Phe Gln
        65                  70                  75 ttg tca caa caa aga ctg tca ttg tta ttc atg att ctc ttc tca ttt     288
Leu Ser Gln Gln Arg Leu Ser Leu Leu Phe Met Ile Leu Phe Ser Phe
        80                  85                  90 ctc cgc aac aaa ttg                                                 303
Leu Arg Asn Lys Leu
        95
```

<210> SEQ ID NO 6
<211> LENGTH: 2218
<212> TYPE: DNA
<213> ORGANISM: Nicotiana tabacum
<220> FEATURE:
<221> NAME/KEY: Intron
<222> LOCATION: (1)..(2218)

<400> SEQUENCE: 6

```
gtaagaaaga tagttacaca cctttattac tctctcagtt ctattttta  cgtgatacta      60
```

| | | |
|---|---|---|
| ttttctttt aatatgttct gaaaagaacg ttaccttttt atatattgat gtaatttcac | 120 |
| tttaaacttc atatttttt tcttaaatag tattgtttta tagtcataaa aatattatta | 180 |
| taagtctttc ttaagttttg tggcttgtta aataaattca cataaaatga aataaagcgg | 240 |
| taggagtacc attcttcatc ttttcttaat taactgacat ttccttcttt ttttgtaagt | 300 |
| ttatatatat taagtaaagt gattttctc ttaagaaatc gccaaaaaaa aaaggaaag | 360 |
| agaagagaag agacaagaag ggggagacaa atggaatcag aaacggtttt gatttgttca | 420 |
| agtgatattt ggtggtagtt gtttcaagca ctgttctttc tgtttgttgg catttgctag | 480 |
| aattaagtgt atatattaat ttgggaaaat ctttaaagtg gttatttta gttttattag | 540 |
| attgagtaac caagacggaa aaaacatgaa ctattttct tttgaaattt ctagtcaaga | 600 |
| acatgcataa aaattctctt ttaaaacgac tctcataaaa attcatgtgg tcgagtttac | 660 |
| gcagcacatg gacccatagt ctccgcctaa ctaagtattt taagtatgta ttttctaaaa | 720 |
| ttcatctaat attttctgtt ggcgcacatg ctccacaaaa gatgaattgt gcatttgttt | 780 |
| gaatattgag ttattactca aaggaatatg gatcaattcc actttttc tcttttcttt | 840 |
| aatattgtac ccatatctta aaaattctag ctccgcctcc gacttgccca tcgtatccgc | 900 |
| cccagccctc agtgggatag agtaggtgag gagtatagtt tataaatgtt ttttctctaa | 960 |
| caattaggtt ttggaataaa ttctgagatt caatggtcta tttgaaacct gtaattacta | 1020 |
| ctccctccgt ttcatattag atgattactt tcctttttag tctattccaa aacaaataac | 1080 |
| acatttctaa atttggaaat aattcaattt taaaatcttt cattttaccc atttaccta | 1140 |
| atgaatgttt ttatagccac acaaatgtca tgaccccaca aatttttac cccttaaact | 1200 |
| tttaagacca caaattttaa aagtttcttc ttttttctta aactatatgc caagtaaaac | 1260 |
| taactcatct tgaaacggag gagtactata agaatagtta tatatgattt ggccccacaa | 1320 |
| attacataat tgtggcaaga aatccaagtt tctagttgtt gataatttag tgatggaggc | 1380 |
| gatctctgtt gaaccgttag agaaaatatt ttgactcatg tcgctttgca tctactgtgt | 1440 |
| tgaagagtag ttgctaggaa ctaacaaagt aattgtagtt tccttgtttt ttttttttcc | 1500 |
| tttcttgatg aattactgta ctttatttc ccatttttt aacgtctgtt acttatggtc | 1560 |
| agttttcaag tgtgaaaaat tagccagaaa gaataattca acaaacttaa ccttttcttt | 1620 |
| tcttcattct tgcgatcttt cctaaatata tttagtagag tctcttttct acttcagtct | 1680 |
| tattgcattt cttgcacacc taacagtagt ggtacataaa ttggacctag ctaacaaaag | 1740 |
| gtaactctta tctgcaagtt taattggtac agtaacatga aacttgttat aatcttttaa | 1800 |
| attgcagccg ataatatatg tatgttttac attggttgtg tgtatataat gtaaattctt | 1860 |
| tacagcatgt ttgactaacc tgcaaaaatt agttttttt ttttcaaaag tatttttggt | 1920 |
| gagaagcagt ttgtgtttgg ctaagtaatt tgaaaaatac ttctgagcaa caattagtgt | 1980 |
| ttgtccaagc ttttaaaaac tgcttttaat tgtattttg tcaaaagagc ttttaaaaa | 2040 |
| agtatttttt agagagaaac tacttttttc tgcttctcca aaattgtttc tgcttctcct | 2100 |
| caaaaacact tttttccctt ctaaaagctt gtacaaacac ttcaactaaa aaaaatatat | 2160 |
| tagcacttat attatcctta taattattga agttaccatc tatcttttgt ggatgtag | 2218 |

<210> SEQ ID NO 7
<211> LENGTH: 258
<212> TYPE: DNA
<213> ORGANISM: Nicotiana tabacum
<220> FEATURE:
<221> NAME/KEY: exon
<222> LOCATION: (1)..(258)

<400> SEQUENCE: 7

```
tta aag cat tga atc aag caa gat tag aag caa gca taa gag tga aag    48
Leu Lys His     Ile Lys Gln Asp     Lys Gln Ala     Glu     Lys
 1           5                   10 gag aga aaa act acc aaa aga aat ggc caa gtc cat ttg caa ttg gca    96
Glu Arg Lys Thr Thr Lys Arg Asn Gly Gln Val His Leu Gln Leu Ala
             15                  20                  25 gtg aaa tat tgc ttg gac tct cat ctt tga agt act ttt ttg cac ctt   144
Val Lys Tyr Cys Leu Asp Ser His Leu     Ser Thr Phe Leu His Leu
         30                  35                  40 tcc aat ggt tag cac ttg cag ctg ttg cag ttg gga ttc ctc caa tta   192
Ser Asn Gly     His Leu Gln Leu Leu Gln Leu Gly Phe Leu Gln Leu
             45                  50                  55 ttt tta gag gtg tgg ctg ccg tgc gaa acc tca ctc ttg aca tcg aca   240
Phe Leu Glu Val Trp Leu Pro Cys Glu Thr Ser Leu Leu Thr Ser Thr
         60                  65                  70 ttc ttg ttt taa tag cag                                            258
Phe Leu Phe     Gln
 75
```

```
<210> SEQ ID NO 8
<211> LENGTH: 3861
<212> TYPE: DNA
<213> ORGANISM: Nicotiana tabacum
<220> FEATURE:
<221> NAME/KEY: Intron
<222> LOCATION: (1)..(3861)
```

<400> SEQUENCE: 8

```
gtactttgct tttccttttc ttctttttta acttttttgaa aagcaaaaag agatactccc     60
ttttgtccca atttatatgg cggtatttaa ttaaacaaaa aaatctaaga aaaatatgaa    120
tactttaaaa atttatggtt tgaaataaat cttaggcatc taaatacaag gttaaaataa    180
taattttaaa gttaaaaaat tcaagaaaga aaggaagact tctaaaattt gtggcaagaa    240
ataaatctta gagatttgtg ttataaatca tctcactaag gctaaaataa taattttaaa    300
gttaaattac ttttaattat gaaaaggtga tagattttttg ggaaaagata gaaaagaaaa    360
ctgtgctata taaattgaga cagagagagt aatttaccat aagagtattt gaagttgatt    420
tggttataga attaacatgt gctcctactt tagctttgtg attgaaattt ggctattgct    480
ttaatttctt agctaattgg atgcttctaa tgtgatgctt gaatccttat tcttgataat    540
gctttgtgat tcattatttc attaaaaagc atgcaccata gggcatgcaa ttaaatattg    600
tatttaagaa tgcactttta actaacccac aagattggag tgggagggat gattcttggg    660
tgttagatgc taatattgga ccaccctagt gactttaaat aacgaaagca tgaaaaacaa    720
ttattggatg cttgatatac tttatgttat aatattttca ggtgacctag aactacacaa    780
ataaacttct ttttccatat tggaatagga tgatttagat ttcaagatgg aattagtgat    840
tctatcacag attatctttt atttaatgat atcaaatatg aaaagagaaa aaaaaaaggt    900
gtctaggaaa tagtcagaaa gatagtatga catatattat tgatacaaat taatcagctc    960
aacacaaagg ctagcatata tttaacaaat agttatagac ttgtagtgtt gtacctttag   1020
ttaagagact aaacactacc aaaaggttgc gatggagcag taggtactcc tctattgtca   1080
tccaggcgcc ttgatataaa ttaattagat cccaaaacga ggatcagata ccaaataaaa   1140
aacaaaaaga aactatcttt agtgtttgtt gatttcatg gcgtagaaaa ataaaggaca   1200
atataataaa aaccttggaa tatcagttaa gatgccttaa tttcaaatca gtggagtata   1260
```

```
ttccgacttc cgtattaatt tcgctctaat caagtctttt aaaagattaa ataatgaaaa    1320
gtttttatag tcacgaaaac attatgacca caaaattttg tcctttaagc tttttagacc    1380
ataaatttca aaaaaaaaaa tttgactgaa atatttaata ccacatattt ttaaaaaatt    1440
atttttttct tacattttagt gtcaagtaaa attagatgtg ataggaaaaa agaatttcga    1500
tttcgtctag taaggaaagt acaaaattgc ttatgtaact cgtaatatat cagaaatggt    1560
ttcccaggtg taaagcacaa acaacggagc ccacatcagt aatgtgtaaa tgtgtaacgt    1620
ttactctctt ttttttcctca ataattgca agaaaatga ctttcctgca agtctttctt    1680
gcccctttta tagaaggtga cgttgactcg taccagattt tcttgtcata gtattaatca    1740
gtagtaatat cagtcacggc gaggtttaaa atttagtcta ttagtaacgt aaataatttt    1800
taaattgtca tatttagtta atctaaaata tcatgcaatt ttttatatca agtttgatat    1860
gttgacgtaa ataatagaac aataatttat aaacttgatt aaattgcatt gataataaat    1920
caaaatatta tttgaacgat taaaatctca cagttaattt tgcatcttgc ataaaaaaat    1980
atccatcata tttccttgat tatcatttga tgccgtctta gtttctttta aaaaaattta    2040
gaatttatat caaatatgat tttttaatta ctcgaactta caagcagact aagtttgata    2100
ttttcctaat tcaacgatat acggttacta cggaaggcat ttactagaaa tactctgaga    2160
tgttactgca attattatta ttattatttt aaaagagaa aaaataact tttaaagctc    2220
catgtgaaat tatgtatatt ttattatagc atgaagtgac cccattttt atctcataaa    2280
taacattgat cccatatttt tctactgtat catcactatc atgaaaaata catctagatt    2340
actgagatgt ttattggcag tagtatctac agatacaaca gatgcttcta gttctattga    2400
tgttttcatt ttgacaaaaa tttaattgag aaagcaaaag atttttgcaag aattcttagg    2460
gttttattca aaaaaaaaaa agaattctta gaaatataag ttttggcaat taaataattc    2520
cagtaattgg gaaaaaacac ttgaataggc tatagaagta aaagaaactt ctatatatta    2580
ccaggcagca gagtttccca aaatcctttt ttctaaaaaa aaaatagtag aaaatgagca    2640
atgtaatttc tttaagtaac attctctatt tagtaaaatg tccattttc taatgaggta    2700
aaagcaatag caaataaaag aaagtttatt ccttttttc gagggtgttg ccgaccaagg    2760
cttaaataga taggaataat cacctaatta agaaaaacta cctatcaatt tttgtctcgg    2820
ttggatttca acatgatacc tcatagttct acgtacgccc acttcaatta ccactaggaa    2880
caccgttggg tgcaggaaaa ttttggtcat aaacttcaat tttaagcctt catataaaca    2940
ataaagagc taattagcag ttaacagtcg agttaatata gctgaataat gcagttcaac    3000
taaatatgta tggaaatggt gaaaagcaca aaggtgactt atccttaggt actttatagc    3060
tttatctttt aaaagtagt agcaagatat gatatgattc cttgaagaag aaaaggtcac    3120
tgtgactctt tatttctatc agtacctgtt tgaataaaat tggctaagaa agttgtaaaa    3180
tggactagca ggacaagaat ctcaatttgg tgttgcttta ccatctttag agtgacagca    3240
atcaaaaacc caaaaattaa ataataata agaaagaaa aagatgagtt attggaaagg    3300
gtaaaatgaa tgaagataag aatactccat tcagtccaaa atattaagct agcatttgga    3360
catagatttg gttgaagctt gaagaaaaga aaaagagtt tttgaagatt atatgaaaaa    3420
taattttga agttaaaat tgtgttaggg aagttttgtg attcaaaaac tactctagaa    3480
ctgtttttgg gatttaaata ttttcttttc aacatgtgcc aaaaaatgat taaaatctat    3540
aaacgaacac ataattgaaa aaagctctca aatttttatga ccaaacagga gcttattgtt    3600
ttggcaaatt gaatttgttt cgaaatactt gatgattaag gagagacaaa ggatagtata    3660
```

```
gacaaaaggc tattagtatt tgtaattgag gctattaaat gtcttttaa agcgatgtgc    3720 aaaaacctta aaaagacga attatatgga ttatattaga agtagtatta aattttaatg    3780
gaacttagtg caatcatttt acaagggcat agtgttaaag ctagaaatgc tgattcttat    3840
agctggcttt gtcatgtgca g                                             3861
```

<210> SEQ ID NO 9
<211> LENGTH: 98
<212> TYPE: DNA
<213> ORGANISM: Nicotiana tabacum
<220> FEATURE:
<221> NAME/KEY: exon
<222> LOCATION: (1)..(98)

<400> SEQUENCE: 9

```
tgg ctg gat caa ttg ttt tac acg att att ggg aag ctg gta cta ttg    48
Trp Leu Asp Gln Leu Phe Tyr Thr Ile Ile Gly Lys Leu Val Leu Leu
1               5                   10                  15 tct tct tat tcg cca ttg cag aat ggc tag agt caa ggg caa gtc aca    96
Ser Ser Tyr Ser Pro Leu Gln Asn Gly     Ser Gln Gly Gln Val Thr
            20                  25                  30 ag                                                                  98
```

<210> SEQ ID NO 10
<211> LENGTH: 4063
<212> TYPE: DNA
<213> ORGANISM: Nicotiana tabacum
<220> FEATURE:
<221> NAME/KEY: Intron
<222> LOCATION: (1)..(4063)

<400> SEQUENCE: 10

```
gtttgtgaat ttcgtccct gtttaatttc cttgcacaag aaatggctag tgtacatcta      60
ctttcctagg atgacagtaa tgtgtgtttt ttttatttat tgtgatacca aaagtatgaa    120
cacctaattt ttctcaggat acatattttc cactttggcc aaactgactt taacaagttg    180
tctcttggat tacgccacat cgaacctaaa agtgttggca ctaccatgtc aacttgtgct    240
gtcttatagg gatttgagac attttgtcta gggtgtcata tggaccccctt cttcatgagc    300 tcgatagcac aaaagcttgc tagtcattct acttgacctg cctcattagc ccgccctacg    360
catgggcatc acaaaccagg ccacacgtag gaattgagtc tcctccctgc ggttcaccca    420
cagaccttac agttttgtcg cttgggtaat gccacaacta gcccgataac gtgcttacca    480
tgtgaacttg taccatatat tacctagcac ttcaccttcc tctcccttg cgacgcgcct     540 aaaatgtcat atgcaccgtt ttttccgaag tttgctagtc tagaagccta ttagttctta    600 ggcttaaccct gcctcattaa ccactctcca tcataggcgt caccttaatt taaaagaatt    660
tgttcttaga aggctctaac ttaaaccaga aatcagttca gctgtcttct gttcttttac    720
ctcaataaca ttgtataatg gtaaggacta aactgcagct ctcttgtgga tgagtggatt    780
aaatttcatt ctgaaaatta atttacttca cagctctatt tggagaaaat aaagattaaa    840
tattgtgaga atgcacggga gaaaatatt atattgatta aagtgttgta caccctatt     900 tatatacagt aattatataa taatatgtat ctacttcccg atgtgggaca ctaaatatga    960
ctaactactt aacacttcct ctcaagccgg tgcatataaa tcatacgtac cgagcttgtt   1020
acagatgtaa ccaatacgag aaccagtaag agacttagtg aaaatatttg ctagctaatc   1080
attcgacttt acaaactttg taacaatatc tcctgagagt atcttttctc tgacaaagtg   1140
acagtcgatc tcaatgtgtt tagtcctctc atggaatacc ggatttgacg caatatgaag   1200
```

```
agcagcttga ttatcacaca ccagttccat cttattgatt tctccgaatt tcaactcctt    1260
gagcaactgc ttgatccaca ctagctcaca cgttgccata gccatggccc gatattcggc    1320
ttcggtgcta gatcgagcaa ctacattctg tttcttgctc ttccaagaga ccaaattacc    1380
tcctactaga acacaatatc cagacgtaga acgtttatca gaaggtgatc ctgcccaatc    1440
agcatttgtg taccctgtaa tctgctcgta gcctcgatcc tcgaatagta acccctttgcc   1500 tggagctgac tttatatatc gaagaatgcg aacaactgca tcccagtgac tatcacaggg    1560
agaatccata aactgactta caacactcac cggaaaagaa atgtctggtt tagtcaccgt    1620
gaggtaattc aatttgccaa ccaacctccg atatctcata ggatctctaa gaggctcccc    1680
ctgtccattg cagaagctta gcattcggat ccataggagt gtcaacaggt ctacatccca    1740
tcattccagt cttctcaaga atgtctaagg catacttccg ctgtgaaata caatacctg     1800 agctagactg agcgacctca atacctggaa aatacttcaa tctgcctaga tccttagtct    1860
ggaagtgcca aaagagatgt tgcttcagat tagtaatacc atcctgatca ttgtcagtaa    1920
taacaatatc gtctacataa accaccatag taaggttatg aacaaaacac gtgcttctaa    1980
agacacgggg tggaagagag aacaaaggta agtgggaaaa caggacagag aatggaactt    2040
gattctggat agctgaagat gacatacgat taataagata gcaagatgta agaactgcat    2100
caccccaaaa atgcaacgga gcatgagatt gtatgagtag agtacgagta gtttcaataa    2160
gatgtctact ctttctttca gctacccat tttgttgaga tgtgtacgga caagatgttt     2220
gatgaataat cccatgagag ttcataaact tctgaaatgg ggaagacaaa tactctaggg    2280
cattatcact acgaaatgtg cggatagaaa ccccaaattg attttgaatt tcagcgtgga    2340
aggtctgaaa aatagaaaat agctcagacc gatttttcat caaaaatatc caagtgcacc    2400
tggaataatc atcaatgaaa ctgacaaagt agcggaatcc caaggtagaa ctgacccgac    2460
taggacccca aacatctgaa tggaccaaag taaaggtga cgctgaggga atgggagtg     2520 ggtatactta ccgagctgtc atgactcata ctctagagtg gacaagtgag ataaaccagg    2580
tatcattttc taaagttttg acaaactggg atgtcccaac cgtttatgta ataaatctgg    2640
tgaatcggta acaagacaag ttattaaagg aagacaagat gcgagtccat atgattttgc    2700
aaggataagg taataaaatc catctaattc atgtctgata ccaatgatcc gccccgtact    2760
atgtttctct ataaaaataa ggtcatcaag aaataaaaca gcgcatttaa gtgatttggc    2820
taagcgacta acggctatga gattaaaagg actattggga acataaagga ctgaatctaa    2880
aggtgaggaa ggaagtgggc ctgcttgacc tattgcagtt gccatggttt gagactcatt    2940
ggccattgtg actgttagaa gagattgaga atatgaatac tggtgaaaag agatttgtta    3000
ccagaaatat gatcagatgc atttgaatca atgacccaag actcaaaggt ttaagattcg    3060
gagacacaag tcacgctact atctgtttga acaatggaag ctatccctga agatgtctgt    3120
ttacatgctt tgtactgaag gaactcagta taatccgata agaaaccat ctggattgga     3180 ttcaacgaat tggatccaac agattgtgag ttaaaggctt ctgatacgaa tgtcattata    3240
atgttgtgcc gaaaaacaa aaaattcctg gaaattacta ttcacgccgg aaaaatataa     3300
aagtgatctg aatttgattt aaattggatg gtatgctcg tatttgcaag gagaagacac     3360
tgccctgaag gaatttttacc aaattctggc cggaaattgc ctcatgtgcg gcgtgtgggc   3420
gtcagaactt cgtcggaaaa attcttccgg cggcgcgtga gggcgcgtgt agccttttt    3480 gccagagatt ttttaatagg ttggtcgctg agctctgaac tacttcccgg tggtgttacc    3540
ttttgcacaa cactgacaga tagtatgatt cttgcggaca gacctatttt tgccggaaaa    3600
```

```
gagcttccgg ttgactgttt tcttttcccg gagtcgctgg aatttatgca ctacgataaa    3660
tttctcacgg ttgctctgat accatgtgag aatgcacggg agaaaattat tatattgatt    3720
aaagtattgt acaaccctat ttatatacag taattacata ataataggta tctacttccc    3780
gatgtgggac actaaacatg actaactact taacaaatat ggtattggaa tttagtctct    3840
ttgacataaa cgacataagc ctatgcttat cttttcttac ttttttagca atgctaaata    3900
gtaggtccta actacaaact ttatagcaca ctgaaaatta ccaaaatata gagatggcca    3960
atgaaggttt tgtctgctaa cataactctg tgtctttatt ttctcactga tattgtatat    4020
ggataaagca ttctgataaa tgaaaacctt tatggttatg tag                     4063

<210> SEQ ID NO 11
<211> LENGTH: 256
<212> TYPE: DNA
<213> ORGANISM: Nicotiana tabacum
<220> FEATURE:
<221> NAME/KEY: exon
<222> LOCATION: (1)..(256)

<400> SEQUENCE: 11 gct acc gcc gct atg tca tca ctg gtc aat ata gtc cct cca aca gca      48
Ala Thr Ala Ala Met Ser Ser Leu Val Asn Ile Val Pro Pro Thr Ala
1               5                  10                  15 gtt tta gcg gaa agc gga gaa gtc gta aat gtt gat gaa gtc aag gtg      96
Val Leu Ala Glu Ser Gly Glu Val Val Asn Val Asp Glu Val Lys Val
            20                  25                  30 aat agc att ctt gct gtg aaa gct ggt gaa act ata cct att gat gga     144
Asn Ser Ile Leu Ala Val Lys Ala Gly Glu Thr Ile Pro Ile Asp Gly
        35                  40                  45 gtt gta gtg gaa ggg gaa tgt gac gtg gac gag aaa aca ctg aca ggc     192
Val Val Val Glu Gly Glu Cys Asp Val Asp Glu Lys Thr Leu Thr Gly
    50                  55                  60 gag tcg ttt cca gtt tct aag caa aga gat tca acg gtc tgg gct ggc     240
Glu Ser Phe Pro Val Ser Lys Gln Arg Asp Ser Thr Val Trp Ala Gly
65                  70                  75                  80 gct aca aat cta aat g                                                256
Ala Thr Asn Leu Asn
                85

<210> SEQ ID NO 12
<211> LENGTH: 85
<212> TYPE: DNA
<213> ORGANISM: Nicotiana tabacum
<220> FEATURE:
<221> NAME/KEY: Intron
<222> LOCATION: (1)..(85)

<400> SEQUENCE: 12
gtagtatagt atttcttcat gcttcattta tttagtgctg aaacttcaag tattgtttgt     60
taatgttatt tgctcaattc ttcag                                           85

<210> SEQ ID NO 13
<211> LENGTH: 142
<212> TYPE: DNA
<213> ORGANISM: Nicotiana tabacum
<220> FEATURE:
<221> NAME/KEY: exon
<222> LOCATION: (1)..(142)

<400> SEQUENCE: 13 gct ata tca gtg tta aga cta cgg ctt tgg ctg aag att gtg cgg tgg      48
Ala Ile Ser Val Leu Arg Leu Arg Leu Trp Leu Lys Ile Val Arg Trp
1               5                  10                  15
```

```
cta gga tgg cac agc ctg tcg aag atg ctc aga aca aga aat caa aaa      96
Leu Gly Trp His Ser Leu Ser Lys Met Leu Arg Thr Arg Asn Gln Lys
         20                  25                  30 ccc aaa gat aca tcg aca agt gtg cta aat att ata cac cag gct a       142
Pro Lys Asp Thr Ser Thr Ser Val Leu Asn Ile Ile His Gln Ala
             35                  40                  45

<210> SEQ ID NO 14
<211> LENGTH: 309
<212> TYPE: DNA
<213> ORGANISM: Nicotiana tabacum
<220> FEATURE:
<221> NAME/KEY: Intron
<222> LOCATION: (1)..(309)

<400> SEQUENCE: 14
gtgaatctta tgttgtgcca catcaagtca aaaaatgcac gtaccgtgtg aacttgttct     60
ttgtcttatg aatcacgtca ctatcctctc ccttttcgat atgagatttc cctaaggtgt    120
catatgaatc ccttcttcgg aagcttgcca gcataggagt ctatcagtcc tttcacttga    180
cccgccctct cagcctgcct gcagtcatgg gcgtcgcact actatattgc tctttcgttt    240
aaaacttttt atttctaata cttccctgct ctttgtgtat gtctaatttc gactggtgat    300
gttttgcag                                                            309

<210> SEQ ID NO 15
<211> LENGTH: 328
<212> TYPE: DNA
<213> ORGANISM: Nicotiana tabacum
<220> FEATURE:
<221> NAME/KEY: exon
<222> LOCATION: (1)..(328)

<400> SEQUENCE: 15 caa ttg tgg cta tac cag ctt ctt tgg caa ttg ttc cta ctg cat taa      48
Gln Leu Trp Leu Tyr Gln Leu Leu Trp Gln Leu Phe Leu Leu His
1               5                   10                  15 gag ttc aca atc gaa atg aat ggt atc gct tgg ctt tgg tca cat tgg      96
Glu Phe Thr Ile Glu Met Asn Gly Ile Ala Trp Leu Trp Ser His Trp
             20                  25                  30 tga gtg cat gtc cgt gtg cac tcg ttc tat cta cac cag ttg cca tgt     144
    Val His Val Arg Val His Ser Phe Tyr Leu His Gln Leu Pro Cys
                 35                  40                  45 gtt gcg cac ttt caa aag cag caa cgt ccg gtc ttc tgt tta aag gag     192
Val Ala His Phe Gln Lys Gln Gln Arg Pro Val Phe Cys Leu Lys Glu
             50                  55                  60 cag agt acc ttg aga ctc tag cta aaa tca aaa tca tgg ctt ttg aca     240
Gln Ser Thr Leu Arg Leu     Leu Lys Ser Lys Ser Trp Leu Leu Thr
             65                  70                  75 aaa cag gga cta taa cta aag gag aat tta tgg tga ccg agt tca agt     288
Lys Gln Gly Leu     Leu Lys Glu Asn Leu Trp     Pro Ser Ser Ser
             80                  85                  90 ctc tga ttg atg gtt tta gtc tca ata cac tgc ttt act g               328
Leu     Leu Met Val Leu Val Ser Ile His Cys Phe Thr
                 95                  100

<210> SEQ ID NO 16
<211> LENGTH: 463
<212> TYPE: DNA
<213> ORGANISM: Nicotiana tabacum
<220> FEATURE:
<221> NAME/KEY: Intron
<222> LOCATION: (1)..(463)
```

-continued

<400> SEQUENCE: 16

```
gtaaaggtta ccactcatac atattctttt atgttgccaa agagaattca aaatcttaac      60
tggttatctt tcacggcaca ttgatagcga taacatga ttgatttata tcatatattc       120
ataaagatg aaatagggag tgccacattc acattctcat attgaagttt ctgaaatggc      180
tctaatggtt caccatagag ccaaaataac atatagacac aacgtcagcc gtctgatatt    240
caggaactta gatggaatag ttggatctta tacattgagg acacataaaa gtacttggtc    300
atataaattt tagaaatata atcaatgtat tataatctaa aattcttcaa atattcttga    360
tactgcaata caaaagcaca tggcacactg aatagaagcc ttgttcggtg gtctaaaaca    420
ttcgtttaga gtaaatactg agttgtctag tgaatatttt cag                      463
```

<210> SEQ ID NO 17
<211> LENGTH: 203
<212> TYPE: DNA
<213> ORGANISM: Nicotiana tabacum
<220> FEATURE:
<221> NAME/KEY: exon
<222> LOCATION: (1)..(203)

<400> SEQUENCE: 17

```
ggt ttc aag cat tga gag caa gtc agg tca tcc gat ggc aac cgc tct       48
Gly Phe Lys His     Glu Gln Val Arg Ser Ser Asp Gly Asn Arg Ser
1               5                   10                  15 ggt gga cta tgc aca atc aaa ttc cgt tga gcc aaa gcc tga tag agt       96
Gly Gly Leu Cys Thr Ile Lys Phe Arg     Ala Lys Ala     Ser
            20                  25 tga gcg gtt tca aaa ttt tcc tgg tga agg gat att tgg aag aat tga     144
    Ala Val Ser Lys Phe Ser Trp     Arg Asp Ile Trp Lys Asn
        30                  35                  40 tgg aat gga aat cta tgt cgg gaa tag gaa aat ttc ttc aag agc tgg     192
Trp Asn Gly Asn Leu Cys Arg Glu     Glu Asn Phe Phe Lys Ser Trp
                45                      50                  55 atg tac cac ag                                                       203
Met Tyr His
```

<210> SEQ ID NO 18
<211> LENGTH: 145
<212> TYPE: DNA
<213> ORGANISM: Nicotiana tabacum
<220> FEATURE:
<221> NAME/KEY: Intron
<222> LOCATION: (1)..(145)

<400> SEQUENCE: 18

```
gtaaatggtt gaatcatttc ttatgctcat agtagagata aaacatcaga gttataatta     60
taagtatatg atttctccag ttaattttgc tgttagattt tctttgacct gtttagcact    120
aatgcggtgg atgtttgaat ttcag                                          145
```

<210> SEQ ID NO 19
<211> LENGTH: 203
<212> TYPE: DNA
<213> ORGANISM: Nicotiana tabacum
<220> FEATURE:
<221> NAME/KEY: exon
<222> LOCATION: (1)..(203)

<400> SEQUENCE: 19

```
tac cag aaa tag agg gtg ata gtt tca aag gaa agt ctg ttg gat aca       48
Tyr Gln Lys     Arg Val Ile Val Ser Lys Glu Ser Leu Leu Asp Thr
1               5                   10                  15
```

| | | | | | | | | | | | | | | | |
|---|---|---|---|---|---|---|---|---|---|---|---|---|---|---|---|
| tat | ttt | tgg | gat | cat | ctc | cag | ctg | gaa | ttt | tca | gtc | ttt | ccg | atg | ttt | 96 |
| Tyr | Phe | Trp | Asp | His | Leu | Gln | Leu | Glu | Phe | Ser | Val | Phe | Pro | Met | Phe | |
| | | | 20 | | | | | 25 | | | | | 30 | | | |

| | | | | | | | | | | | | | |
|---|---|---|---|---|---|---|---|---|---|---|---|---|---|
| gtc | gaa | ttg | gtg | taa | aag | aag | caa | tga | gag | aac | tga | agc | aga | tgg | gta | 144 |
| Val | Glu | Leu | Val | | Lys | Lys | Gln | | Glu | Asn | | Ser | Arg | Trp | Val | |
| | | | 35 | | | | | | 40 | | | | | | | |

| | | | | | | | | | | | | | |
|---|---|---|---|---|---|---|---|---|---|---|---|---|---|
| tca | aaa | ccg | cga | tgc | tta | ctg | gtg | atc | gtt | atg | cag | ctg | cca | acc | atg | 192 |
| Ser | Lys | Pro | Arg | Cys | Leu | Leu | Val | Ile | Val | Met | Gln | Leu | Pro | Thr | Met | |
| 45 | | | | | 50 | | | | | 55 | | | | | 60 | |

| | | | |
|---|---|---|---|
| tgc | agg | atc | ag | 203 |
| Cys | Arg | Ile | | |

<210> SEQ ID NO 20
<211> LENGTH: 619
<212> TYPE: DNA
<213> ORGANISM: Nicotiana tabacum
<220> FEATURE:
<221> NAME/KEY: Intron
<222> LOCATION: (1)..(619)

<400> SEQUENCE: 20

```
gtatattaat aattctgcat tacgctgaaa tgattataaa acccctttgga ttattgttta      60
gtcttaagaa ttttcactga actcttattg tttccttctt ctatcatcaa cattggttaa     120
acatttcatc taaatttaga gaacgtatca ccaagtaagt gctttacctt tacagggtca     180
tataaaatac ttaagacagt gtgatgtgaa gatgaaggtt aaatgttgat ctggataaac     240
caagttatta tcacaactaa tataagatat gctattgttc tccaataatt ggacgatttt     300
cggacgtacg acgtacaatt cttcacatat gaaacctaca tcagacgtac atgacacgct     360
atgtttagca taaagagtca agattagcat gatgatttaa gctgaatctg aatttcaagt     420
atctattctt gtattgtacc caggggcgga actagtgttg tgcttagagg tctcaaacat     480
tgtatttgtg ttaaaaaatt cacttcatat gtatttaaat aatttatcca gagcagtgag     540
ccatattttt tagaatccag aacccataaa ctcaaaatca tagatccacc tctgattgta     600
agtcggaaca attatgcag                                                  619
```

<210> SEQ ID NO 21
<211> LENGTH: 1498
<212> TYPE: DNA
<213> ORGANISM: Nicotiana tabacum
<220> FEATURE:
<221> NAME/KEY: exon
<222> LOCATION: (1)..(1498)

<400> SEQUENCE: 21

| | | | | | | | | | | | | | | | |
|---|---|---|---|---|---|---|---|---|---|---|---|---|---|---|---|
| tta | ggt | gga | gct | ttg | gat | gaa | ttt | caa | gca | gaa | ctc | cta | cca | gag | gac | 48 |
| Leu | Gly | Gly | Ala | Leu | Asp | Glu | Phe | Gln | Ala | Glu | Leu | Leu | Pro | Glu | Asp | |
| 1 | | | | 5 | | | | | 10 | | | | | 15 | | |

| | | | | | | | | | | | | | | | |
|---|---|---|---|---|---|---|---|---|---|---|---|---|---|---|---|
| aag | gca | aca | atc | atc | aag | ggt | ttt | cag | aag | gaa | gct | cca | aca | gcg | atg | 96 |
| Lys | Ala | Thr | Ile | Ile | Lys | Gly | Phe | Gln | Lys | Glu | Ala | Pro | Thr | Ala | Met | |
| | | 20 | | | | | 25 | | | | | 30 | | | | |

| | | | | | | | | | | | | | | | |
|---|---|---|---|---|---|---|---|---|---|---|---|---|---|---|---|
| ata | ggc | gac | ggc | ctt | aat | gat | gct | cct | gca | tta | gca | aca | gct | gac | att | 144 |
| Ile | Gly | Asp | Gly | Leu | Asn | Asp | Ala | Pro | Ala | Leu | Ala | Thr | Ala | Asp | Ile | |
| | | | 35 | | | | | 40 | | | | | 45 | | | |

| | | | | | | | | | | | | | | | |
|---|---|---|---|---|---|---|---|---|---|---|---|---|---|---|---|
| ggc | atc | tca | atg | ggc | atc | tct | ggg | tca | gct | ctc | gct | aaa | gaa | aca | ggc | 192 |
| Gly | Ile | Ser | Met | Gly | Ile | Ser | Gly | Ser | Ala | Leu | Ala | Lys | Glu | Thr | Gly | |
| | 50 | | | | | 55 | | | | | 60 | | | | | |

| | | | | | | | | | | | | | | | |
|---|---|---|---|---|---|---|---|---|---|---|---|---|---|---|---|
| cat | gct | ata | cta | atg | aca | aat | gac | atc | gga | aga | ata | ccg | aaa | gct | gca | 240 |
| His | Ala | Ile | Leu | Met | Thr | Asn | Asp | Ile | Gly | Arg | Ile | Pro | Lys | Ala | Ala | |
| 65 | | | | | 70 | | | | | 75 | | | | | 80 | |

| | | | | | | | | | | | | | | | |
|---|---|---|---|---|---|---|---|---|---|---|---|---|---|---|---|
| cgt | ctt | gct | aga | aga | gtt | cga | agg | aag | att | gtt | gag | aat | atg | att | ata | 288 |

```
Arg Leu Ala Arg Arg Val Arg Arg Lys Ile Val Glu Asn Met Ile Ile
                 85                  90                  95 tca gcc gtt aca aag gct gcc ata gtt gca ttg gca ata gca ggt tat       336
Ser Ala Val Thr Lys Ala Ala Ile Val Ala Leu Ala Ile Ala Gly Tyr
            100                 105                 110 cca ttg gtt tgg gct gct gtc ctc gca gat act ggg aca tgc ttg cta       384
Pro Leu Val Trp Ala Ala Val Leu Ala Asp Thr Gly Thr Cys Leu Leu
            115                 120                 125 gtg att ttg aac agc atg cta ctt cta cga gga ggc aca cgc aga cat       432
Val Ile Leu Asn Ser Met Leu Leu Arg Gly Gly Thr Arg Arg His
            130                 135                 140 ggg aaa aaa tgt tgg aga tct tct act cct tcg cat gct ccc cac cac       480
Gly Lys Lys Cys Trp Arg Ser Ser Thr Pro Ser His Ala Pro His His
145                 150                 155                 160 aaa gac aaa gct tca tgt tgc aag tcg gaa aat gct ccc cag ctg tgt       528
Lys Asp Lys Ala Ser Cys Cys Lys Ser Glu Asn Ala Pro Gln Leu Cys
                165                 170                 175 tgc tct gat att gag tca caa aag aaa tgt aca agt caa tca tgc tcg       576
Cys Ser Asp Ile Glu Ser Gln Lys Lys Cys Thr Ser Gln Ser Cys Ser
            180                 185                 190 tcc gag gtg tgt gtt cca aga tgt caa cct gtc tcc tcg gga tca aag       624
Ser Glu Val Cys Val Pro Arg Cys Gln Pro Val Ser Ser Gly Ser Lys
            195                 200                 205 tca tgt gga aat aat cag tgc cca gac tcc att gaa aat agt ggt ttt       672
Ser Cys Gly Asn Asn Gln Cys Pro Asp Ser Ile Glu Asn Ser Gly Phe
210                 215                 220 cat tct cat cgc cgt cct caa tgc tgc tcg tcg aag atg gct gct aaa       720
His Ser His Arg Arg Pro Gln Cys Cys Ser Ser Lys Met Ala Ala Lys
225                 230                 235                 240 gca tgc caa tct gca gtt tca gaa tca aag tca tgc gga aat aat cag       768
Ala Cys Gln Ser Ala Val Ser Glu Ser Lys Ser Cys Gly Asn Asn Gln
                245                 250                 255 tgc cca gac tcc gtt gaa aat agt ggt ttt cat tct cat ccc cgt cct       816
Cys Pro Asp Ser Val Glu Asn Ser Gly Phe His Ser His Pro Arg Pro
            260                 265                 270 gaa tgc tgc tcg tcg aag atg gct gct aaa gcg tgc caa tct gca gtt       864
Glu Cys Cys Ser Ser Lys Met Ala Ala Lys Ala Cys Gln Ser Ala Val
            275                 280                 285 tca gaa tca aag tca tgt gga aat aat cag tgc cca gac tcc gtt gga       912
Ser Glu Ser Lys Ser Cys Gly Asn Asn Gln Cys Pro Asp Ser Val Gly
            290                 295                 300 aat agt ggt ttt cat tct cat ccc cgt cct caa tgc tgt tca tcg aag       960
Asn Ser Gly Phe His Ser His Pro Arg Pro Gln Cys Cys Ser Ser Lys
305                 310                 315                 320 atg gct gct aaa gca ggc caa tct gca ctt tca gaa tca aag tca tgt      1008
Met Ala Ala Lys Ala Gly Gln Ser Ala Leu Ser Glu Ser Lys Ser Cys
                325                 330                 335 gga aat aac aat tgc tca gac tcc att cac aag agt aat tgt cat tct      1056
Gly Asn Asn Asn Cys Ser Asp Ser Ile His Lys Ser Asn Cys His Ser
            340                 345                 350 tta act aac tct cta gta tgt tct tcc aag atg tct gct cca caa tgt      1104
Leu Thr Asn Ser Leu Val Cys Ser Ser Lys Met Ser Ala Pro Gln Cys
            355                 360                 365 cat tct gct act tca agc aac aaa tca tgt gga agt acc aag tgc tcc      1152
His Ser Ala Thr Ser Ser Asn Lys Ser Cys Gly Ser Thr Lys Cys Ser
370                 375                 380 gac ttc agt gat aaa aaa tgt tgt caa tcc gac aaa att cct caa gcg      1200
Asp Phe Ser Asp Lys Lys Cys Cys Gln Ser Asp Lys Ile Pro Gln Ala
385                 390                 395                 400 tgc tct acc aag aag tct gct cca ggg tgt caa tct gca gtt tct ggg      1248
Cys Ser Thr Lys Lys Ser Ala Pro Gly Cys Gln Ser Ala Val Ser Gly
```

|  |  |  |  |  |  |  |  |  |  |  |  |  |  |  |
|---|---|---|---|---|---|---|---|---|---|---|---|---|---|---|
| Cys | Ser | Thr | Lys | Lys | Ser | Ala | Pro | Gly | Cys | Gln | Ser | Ala | Val | Ser | Gly |
|  |  |  |  | 405 |  |  |  |  | 410 |  |  |  |  | 415 |

```
tct aaa tca tgt gga aat agc aag tgt tca gac tca aaa gac aat agt      1296
Ser Lys Ser Cys Gly Asn Ser Lys Cys Ser Asp Ser Lys Asp Asn Ser
            420                 425                 430 agc cat cct tca cat ccc gat cat caa aca tgc atg tct aag ttg tgt      1344
Ser His Pro Ser His Pro Asp His Gln Thr Cys Met Ser Lys Leu Cys
            435                 440                 445 gct cca caa agc caa tct gca act tca agc tcc agg aca tgt gga aat      1392
Ala Pro Gln Ser Gln Ser Ala Thr Ser Ser Ser Arg Thr Cys Gly Asn
            450                 455                 460 aca aag tgc tcg gac acc aat agc aag aat tct tgt tat tca caa acc      1440
Thr Lys Cys Ser Asp Thr Asn Ser Lys Asn Ser Cys Tyr Ser Gln Thr
465                 470                 475                 480 aac tct gaa tca tgc tct tca aag atg tct ggt cca tca tgc aaa act      1488
Asn Ser Glu Ser Cys Ser Ser Lys Met Ser Gly Pro Ser Cys Lys Thr
                485                 490                 495 gct aat tca g                                                        1498
Ala Asn Ser
```

```
<210> SEQ ID NO 22
<211> LENGTH: 321
<212> TYPE: DNA
<213> ORGANISM: Nicotiana tabacum
<220> FEATURE:
<221> NAME/KEY: Intron
<222> LOCATION: (1)..(321)

<400> SEQUENCE: 22
gtacgaccag attcctcttc ttgttaatac cccccgaacc aaactatagg atctaaagta     60
ttatttggcc ctctgtcgga ggatataatg gttagttaaa cctgaaatca tgtagtctat    120
gaattgcaaa tctctagcat cgtgacaaaa ttcttagatc atatacaact tgagaatat     180 aggctgtcac agacccttct tcatactgca ttagaggaga gcagccaatt ttttattcat    240
gatttgaaac aaataaagtt cttcttgagg tgtatggaga ggctatgaga atcatttgct    300
gagtaggttt gagattttca g                                              321
```

```
<210> SEQ ID NO 23
<211> LENGTH: 333
<212> TYPE: DNA
<213> ORGANISM: Nicotiana tabacum
<220> FEATURE:
<221> NAME/KEY: exon
<222> LOCATION: (1)..(333)

<400> SEQUENCE: 23 gtt caa ggt cat gca gaa ata aga agt gcc agg act ctg caa ccg aga       48
Val Gln Gly His Ala Glu Ile Arg Ser Ala Arg Thr Leu Gln Pro Arg
1               5                   10                  15 aca gtt ttc att cac cac tta cta atc cac tca gtg ggg aaa agc ttt       96
Thr Val Phe Ile His His Leu Leu Ile His Ser Val Gly Lys Ser Phe
                20                  25                  30 cgg agc aga aaa gct tgg att tag tcc gaa aag ata agg aat caa gtc      144
Arg Ser Arg Lys Ala Trp Ile     Ser Glu Lys Ile Arg Asn Gln Val
            35                  40                  45 atg atc ttc gtc atg gct gct ctg acg agg aac atg atc ata caa att      192
Met Ile Phe Val Met Ala Ala Leu Thr Arg Asn Met Ile Ile Gln Ile
            50                  55                  60 tag aca agg cat atg aca gtt gtg cct tac aag aat gtt gtt att cgg      240
    Thr Arg His Met Thr Val Val Pro Tyr Lys Asn Val Val Ile Arg
            65                  70                  75
```

```
ttc aag gca ata aaa ctg atg tat cag aaa ctg gaa tcc agg aaa ctg      288
Phe Lys Ala Ile Lys Leu Met Tyr Gln Lys Leu Glu Ser Arg Lys Leu
     80                  85                  90 ctc att gtg aca gca cca atc aaa cat gcc aaa ctg caa gtt cag          333
Leu Ile Val Thr Ala Pro Ile Lys His Ala Lys Leu Gln Val Gln
 95                 100                 105
```

<210> SEQ ID NO 24
<211> LENGTH: 220
<212> TYPE: DNA
<213> ORGANISM: Nicotiana tabacum
<220> FEATURE:
<221> NAME/KEY: Intron
<222> LOCATION: (1)..(220)

<400> SEQUENCE: 24

```
gtaggcacta ccaaatcata tgatccaaag tgctcctcca ccttcactcc tacaataaat     60
gttcgatcaa acttcataag aagatagcat atgcatcgca aatctctaaa aaaatgatgg    120
ataatgttac tcaccaacta gtttgagata aagtttaaac tgattgctat atatcgttaa    180
ctataaaaaa ctacttgtta attagagctg agattttcag                          220
```

<210> SEQ ID NO 25
<211> LENGTH: 774
<212> TYPE: DNA
<213> ORGANISM: Nicotiana tabacum
<220> FEATURE:
<221> NAME/KEY: exon
<222> LOCATION: (1)..(774)

<400> SEQUENCE: 25

```
gat cga tga cat gcg gaa atg ata aga tcc tgg act ctc taa gca tcc      48
Asp Arg     His Ala Glu Met Ile Arg Ser Trp Thr Leu     Ala Ser
 1                   5                  10 atg gtt gtc att cgc atg ata atc cac tcc acg agg aga aca acc tgg      96
Met Val Val Ile Arg Met Ile Ile His Ser Thr Arg Arg Thr Thr Trp
 15                  20                  25                  30 agc aga aaa tct tgg atg ttg ttg gag aag gta taa aat cac ctc atg     144
Ser Arg Lys Ser Trp Met Leu Leu Glu Lys Val     Asn His Leu Met
                 35                  40                  45 ctg tcg gtc atg gct gtt cgg aca agg aac acg atc act cac atc cag     192
Leu Ser Val Met Ala Val Arg Thr Arg Asn Thr Ile Thr His Ile Gln
             50                  55                  60 aaa agg cat atg aca gtt gtg caa cag atg att gtt gtt ttt cag ttc     240
Lys Arg His Met Thr Val Val Gln Gln Met Ile Val Val Phe Gln Phe
         65                  70                  75 aag tcc atg gca ttg acg acg tat caa aaa gtg aaa ttc aag aaa ctg     288
Lys Ser Met Ala Leu Thr Thr Tyr Gln Lys Val Lys Phe Lys Lys Leu
     80                  85                  90 ctc att gtg aca gca caa agc aga gca tgg tca tct cca gca gct gca     336
Leu Ile Val Thr Ala Gln Ser Arg Ala Trp Ser Ser Pro Ala Ala Ala
 95                 100                 105 aac atg aac caa aag atc agg taa atc act gtg gac ttc act cta aaa     384
Asn Met Asn Gln Lys Ile Arg     Ile Thr Val Asp Phe Thr Leu Lys
110                 115                 120 cta ctc caa ctg atg aag aac tag cca agc tgg tta gaa gat gct gcg     432
Leu Leu Gln Leu Met Lys Asn     Pro Ser Trp Leu Glu Asp Ala Ala
125                 130                 135 aat aca aac cat gcc acg acg tcc gtt ctg gct gca gga agc atg ctg     480
Asn Thr Asn His Ala Thr Thr Ser Val Leu Ala Ala Gly Ser Met Leu
140                 145                 150                 155 cag aat gtg gtc caa ccg ttc gat caa cta tca ata tct tac ggg aca     528
Gln Asn Val Val Gln Pro Phe Asp Gln Leu Ser Ile Ser Tyr Gly Thr
```

```
               160                 165                 170
acc atc atc att acc tag act gca gtg gtc gta agg ttt gtt cgc tgt      576
Thr Ile Ile Ile Thr     Thr Ala Val Val Val Arg Phe Val Arg Cys
            175                 180                 185 tgg aga aga gac aca tcg gtg gat gct gtg aca gct tca gaa aag aat      624
Trp Arg Arg Asp Thr Ser Val Asp Ala Val Thr Ala Ser Glu Lys Asn
            190                 195                 200 gtt gtg cca aga aga acc acc ttg gag caa gtt tcg gag gag gtt tat      672
Val Val Pro Arg Arg Thr Thr Leu Glu Gln Val Ser Glu Glu Val Tyr
            205                 210                 215 cag aaa ttg tca tag agt aga tgc aat ccg aag tgt aca tat gtt gta      720
Gln Lys Leu Ser     Ser Arg Cys Asn Pro Lys Cys Thr Tyr Val Val
        220                 225                 230 aac ttc cta cct att tta tct tca aga agt tga gct gct aat ttg aac      768
Asn Phe Leu Pro Ile Leu Ser Ser Arg Ser     Ala Ala Asn Leu Asn
        235                 240                 245 aaa gca                                                              774
Lys Ala
    250

<210> SEQ ID NO 26
<211> LENGTH: 498
<212> TYPE: DNA
<213> ORGANISM: Nicotiana tabacum
<220> FEATURE:
<221> NAME/KEY: Intron
<222> LOCATION: (1)..(498)

<400> SEQUENCE: 26
agggcgaatt ctgcagatat ccatcacact ggcggccgct cgagcatgca tctagagggc      60
ccaattcgcc ctatagtgag tcgtattaca attcactggc cgtcgtttta caacgtcgtg     120
actgggaaaa ccctggcgtt acccaactta atcgccttgc agcacatccc cctttcgcca     180
gctggcgtaa tagcgaagag gcccgcaccg atcgcccttc ccaacagttg cgcagcctat     240
acgtacggca gtttaaggtt tacacctata aaagagagag ccgttatcgt ctgtttgtgg     300
atgtacagag tgatattatt gacacgccgg ggcgacggat ggtgatcccc ctggccagtg     360
cacgtctgct gtcagataaa gtctcccgtg aactttaccc ggtggtgcat atcggggatg     420
aaagctggcg catgatgacc accgatatgg ccagtgtgcc ggtctccgtt atcggggaag     480
aagtggctga tctcagcc                                                  498

<210> SEQ ID NO 27
<211> LENGTH: 303
<212> TYPE: DNA
<213> ORGANISM: Artificial Sequence
<220> FEATURE:
<223> OTHER INFORMATION: Reverse Complementary Sequence of Exon 1

<400> SEQUENCE: 27
caatttgttg cggagaaatg agaagagaat catgaataac aatgacagtc tttgttgtga      60
caattactga aacctcttta accccttcaa gattcttgag aattttttca actagaacaa     120
cttctgaagt acagcaaatt cccaaaacat caaaatagct cttgctcaac ttctttgttt     180
cattcatttt ttcactttcc accattttc tccttctcta aggaggagga aagataata     240 gatgaaaaag gaatttctag ttctggaata tattggatat acttttgttt tggaaagagg     300
tga                                                                  303

<210> SEQ ID NO 28
<211> LENGTH: 258
```

<212> TYPE: DNA
<213> ORGANISM: Artificial Sequence
<220> FEATURE:
<223> OTHER INFORMATION: Reverse Complementary Sequence of Exon 2

<400> SEQUENCE: 28

```
ctgctattaa aacaagaatg tcgatgtcaa gagtgaggtt tcgcacggca gccacacctc      60
taaaaataat tggaggaatc ccaactgcaa cagctgcaag tgctaaccat tggaaaggtg     120
caaaaaagta cttcaaagat gagagtccaa gcaatatttc actgccaatt gcaaatggac     180
ttggccattt cttttggtag ttttctctc ctttcactct tatgcttgct tctaatcttg      240
cttgattcaa tgctttaa                                                   258
```

<210> SEQ ID NO 29
<211> LENGTH: 98
<212> TYPE: DNA
<213> ORGANISM: Artificial Sequence
<220> FEATURE:
<223> OTHER INFORMATION: Reverse Complementary Sequence of Exon 3

<400> SEQUENCE: 29

```
cttgtgactt gcccttgact ctagccattc tgcaatggcg aataagaaga caatagtacc      60
agcttcccaa taatcgtgta aaacaattga tccagcca                              98
```

<210> SEQ ID NO 30
<211> LENGTH: 256
<212> TYPE: DNA
<213> ORGANISM: Artificial Sequence
<220> FEATURE:
<223> OTHER INFORMATION: Reverse Complementary Sequence of Exon 4

<400> SEQUENCE: 30

```
catttagatt tgtagcgcca gcccagaccg ttgaatctct ttgcttagaa actggaaacg      60
actcgcctgt cagtgttttc tcgtccacgt cacattcccc ttccactaca actccatcaa     120
taggtatagt ttcaccagct ttcacagcaa gaatgctatt caccttgact tcatcaacat     180
ttacgacttc tccgctttcc gctaaaactg ctgttggagg gactatattg accagtgatg     240
acatagcggc ggtagc                                                     256
```

<210> SEQ ID NO 31
<211> LENGTH: 142
<212> TYPE: DNA
<213> ORGANISM: Artificial Sequence
<220> FEATURE:
<223> OTHER INFORMATION: Reverse Complementary Sequence of Exon 5

<400> SEQUENCE: 31

```
tagcctggtg tataatattt agcacacttg tcgatgtatc tttgggtttt tgatttcttg      60
ttctgagcat cttcgacagg ctgtgccatc ctagccaccg cacaatcttc agccaaagcc     120
gtagtcttaa cactgatata gc                                              142
```

<210> SEQ ID NO 32
<211> LENGTH: 328
<212> TYPE: DNA
<213> ORGANISM: Artificial Sequence
<220> FEATURE:
<223> OTHER INFORMATION: Reverse Complementary Sequence of Exon 6

<400> SEQUENCE: 32

```
cagtaaagca gtgtattgag actaaaacca tcaatcagag acttgaactc ggtcaccata      60
aattctcctt tagttatagt ccctgttttg tcaaaagcca tgattttgat tttagctaga    120
```

```
gtctcaaggt actctgctcc tttaaacaga agaccggacg ttgctgcttt tgaaagtgcg      180
caacacatgg caactggtgt agatagaacg agtgcacacg gacatgcact caccaatgtg      240
accaaagcca agcgatacca ttcatttcga ttgtgaactc ttaatgcagt aggaacaatt      300
gccaaagaag ctggtatagc cacaattg                                         328

<210> SEQ ID NO 33
<211> LENGTH: 203
<212> TYPE: DNA
<213> ORGANISM: Artificial Sequence
<220> FEATURE:
<223> OTHER INFORMATION: Reverse Complementary Sequence of Exon 7

<400> SEQUENCE: 33
ctgtggtaca tccagctctt gaagaaattt tcctattccc gacatagatt tccattccat       60
caattcttcc aaatatccct tcaccaggaa aattttgaaa ccgctcaact ctatcaggct      120
ttggctcaac ggaatttgat tgtgcatagt ccaccagagc ggttgccatc ggatgacctg      180
acttgctctc aatgcttgaa acc                                              203

<210> SEQ ID NO 34
<211> LENGTH: 203
<212> TYPE: DNA
<213> ORGANISM: Artificial Sequence
<220> FEATURE:
<223> OTHER INFORMATION: Reverse Complementary Sequence of Exon 8

<400> SEQUENCE: 34
ctgatcctgc acatggttgg cagctgcata acgatcacca gtaagcatcg cggttttgat       60
acccatctgc ttcagttctc tcattgcttc ttttacacca attcgacaaa catcggaaag      120
actgaaaatt ccagctggag atgatcccaa aaatatgtat ccaacagact ttcctttgaa      180
actatcaccc tctatttctg gta                                              203

<210> SEQ ID NO 35
<211> LENGTH: 1498
<212> TYPE: DNA
<213> ORGANISM: Artificial Sequence
<220> FEATURE:
<223> OTHER INFORMATION: Reverse Complementary Sequence of Exon 9

<400> SEQUENCE: 35
ctgaattagc agttttgcat gatggaccag acatctttga agagcatgat tcagagttgg       60
tttgtgaata caagaattc ttgctattgg tgtccgagca ctttgtattt ccacatgtcc       120
tggagcttga agttgcagat tggctttgtg gagcacacaa cttagacatg catgtttgat      180
gatcgggatg tgaaggatgg ctactattgt cttttgagtc tgaacacttg ctatttccac      240
atgatttaga cccagaaact gcagattgac accctggagc agacttcttg gtagagcacg      300
cttgaggaat tttgtcggat tgacaacatt ttttatcact gaagtcggag cacttggtac      360
ttccacatga tttgttgctt gaagtagcag aatgacattg tggagcagac atcttggaag      420
aacatactag agagttagtt aaagaatgac aattactctt gtgaatggag tctgagcaat      480
tgttatttcc acatgacttt gattctgaaa gtgcagattg gcctgcttta gcagccatct      540
tcgatgaaca gcattgagga cggggatgag aatgaaaacc actatttcca acggagtctg      600
ggcactgatt atttccacat gactttgatt ctgaaactgc agattggcac gctttagcag      660
ccatcttcga cgagcagcat tcaggacggg gatgagaatg aaaaccacta ttttcaacgg      720
agtctgggca ctgattattt ccgcatgact ttgattctga aactgcagat tggcatgctt      780
```

```
tagcagccat cttcgacgag cagcattgag gacggcgatg agaatgaaaa ccactatttt      840
caatggagtc tgggcactga ttatttccac atgactttga tcccgaggag acaggttgac      900
atcttggaac acacacctcg gacgagcatg attgacttgt acatttcttt tgtgactcaa      960
tatcagagca acacagctgg ggagcatttt ccgacttgca acatgaagct ttgtctttgt     1020
ggtggggagc atgcgaagga gtagaagatc tccaacattt tttcccatgt ctgcgtgtgc     1080
ctcctcgtag aagtagcatg ctgttcaaaa tcactagcaa gcatgtccca gtatctgcga     1140
ggacagcagc ccaaaccaat ggataacctg ctattgccaa tgcaactatg gcagcctttg     1200
taacggctga tataatcata ttctcaacaa tcttccttcg aactcttcta gcaagacgtg     1260
cagctttcgg tattcttccg atgtcatttg tcattagtat agcatggcct gtttctttag     1320
cgagagctga cccagagatg cccattgaga tgccaatgtc agctgttgct aatgcaggag     1380
catcattaag gccgtcgcct atcatcgctg ttggagcttc cttctgaaaa cccttgatga     1440
ttgttgcctt gtcctctggt aggagttctg cttgaaattc atccaaagct ccacctaa       1498

<210> SEQ ID NO 36
<211> LENGTH: 333
<212> TYPE: DNA
<213> ORGANISM: Artificial Sequence
<220> FEATURE:
<223> OTHER INFORMATION: Reverse Complementary Sequence of Exon 10

<400> SEQUENCE: 36
ctgaacttgc agtttggcat gtttgattgg tgctgtcaca atgagcagtt tcctggattc       60
cagtttctga tacatcagtt ttattgcctt gaaccgaata acaacattct tgtaaggcac      120
aactgtcata tgccttgtct aaatttgtat gatcatgttc ctcgtcagag cagccatgac      180
gaagatcatg acttgattcc ttatcttttc ggactaaatc caagcttttc tgctccgaaa      240
gcttttcccc actgagtgga ttagtaagtg gtgaatgaaa actgttctcg gttgcagagt      300
cctggcactt cttatttctg catgaccttg aac                                   333

<210> SEQ ID NO 37
<211> LENGTH: 774
<212> TYPE: DNA
<213> ORGANISM: Artificial Sequence
<220> FEATURE:
<223> OTHER INFORMATION: Reverse Complementary Sequence of Exon 11

<400> SEQUENCE: 37
tgctttgttc aaattagcag ctcaacttct tgaagataaa ataggtagga agtttacaac       60
atatgtacac ttcggattgc atctactcta tgacaatttc tgataaacct cctccgaaac      120
ttgctccaag gtggttcttc ttggcacaac attcttttct gaagctgtca cagcatccac      180
cgatgtgtct cttctccaac agcgaacaaa ccttacgacc actgcagtct aggtaatgat      240
gatggttgtc ccgtaagata ttgatagttg atcgaacggt tggaccacat tctgcagcat      300
gcttcctgca gccagaacgg acgtcgtggc atggtttgta ttcgcagcat cttctaacca      360
gcttggctag ttcttcatca gttggagtag ttttagagtg aagtccacag tgatttacct      420
gatcttttgg ttcatgtttg cagctgctgg agatgaccat gctctgcttt gtgctgtcac      480
aatgagcagt ttcttgaatt tcactttttg atacgtcgtc aatgccatgg acttgaactg      540
aaaaacaaca atcatctgtt gcacaactgt catatgcctt ttctggatgt gagtgatcgt      600
gttccttgtc cgaacagcca tgaccgacag catgaggtga ttttatacct tctccaacaa      660
catccaagat tttctgctcc aggttgttct cctcgtggag tggattatca tgcgaatgac      720
```

```
aaccatggat gcttagagag tccaggatct tatcatttcc gcatgtcatc gatc         774
```

<210> SEQ ID NO 38
<211> LENGTH: 260
<212> TYPE: DNA
<213> ORGANISM: Artificial Sequence
<220> FEATURE:
<223> OTHER INFORMATION: Sense Sequence Transgene Construct

<400> SEQUENCE: 38

```
atttgtagtg ccagcccaga ccgttgaatc tatttgctta gaaactggaa acgactcgcc    60
tgtcagtgtt ttctcgtcca cgtcacattc cccttccatt acaactccat caataggtat   120
agtttcacca gctttaacag caagaatgct attcaacttg acttcatcaa catttacgac   180
ttctccactt tcagctaaaa ctgctgttgg agggactata ttgaccagtg atgacatagc   240
agcagtagcc tacataacca                                               260
```

<210> SEQ ID NO 39
<211> LENGTH: 96
<212> TYPE: DNA
<213> ORGANISM: Artificial Sequence
<220> FEATURE:
<223> OTHER INFORMATION: Spacer Sequence Transgene Construct

<400> SEQUENCE: 39

```
agcctgaaga attgagcaaa taacattaac aaacaatact tgaagtttca gcactaaata    60
aatgaagcat gaaggaatac tacactacca tttaga                              96
```

<210> SEQ ID NO 40
<211> LENGTH: 260
<212> TYPE: DNA
<213> ORGANISM: Artificial Sequence
<220> FEATURE:
<223> OTHER INFORMATION: Reverse Complement Sequence Transgene Construct

<400> SEQUENCE: 40

```
tggttatgta ggctactgct gctatgtcat cactggtcaa tatagtccct ccaacagcag    60
ttttagctga aagtggagaa gtcgtaaatg ttgatgaagt caagttgaat agcattcttg   120
ctgttaaagc tggtgaaact atacctattg atggagttgt aatggaaggg gaatgtgacg   180
tggacgagaa aacactgaca ggcgagtcgt ttccagtttc taagcaaata gattcaacgg   240
tctgggctgg cactacaaat                                               260
```

<210> SEQ ID NO 41
<211> LENGTH: 616
<212> TYPE: DNA
<213> ORGANISM: Artificial Sequence
<220> FEATURE:
<223> OTHER INFORMATION: RNAi sequence

<400> SEQUENCE: 41

```
atttgtagtg ccagcccaga ccgttgaatc tatttgctta gaaactggaa acgactcgcc    60
tgtcagtgtt ttctcgtcca cgtcacattc cccttccatt acaactccat caataggtat   120
agtttcacca gctttaacag caagaatgct attcaacttg acttcatcaa catttacgac   180
ttctccactt tcagctaaaa ctgctgttgg agggactata ttgaccagtg atgacatagc   240
agcagtagcc tacataacca agcctgaaga attgagcaaa taacattaac aaacaatact   300
tgaagtttca gcactaaata aatgaagcat gaaggaatac tacactacca tttagatggt   360
tatgtaggct actgctgcta tgtcatcact ggtcaatata gtccctccaa cagcagtttt   420
```

```
agctgaaagt ggagaagtcg taaatgttga tgaagtcaag ttgaatagca ttcttgctgt    480
taaagctggt gaaactatac ctattgatgg agttgtaatg aaggggaat gtgacgtgga      540 cgagaaaaca ctgacaggcg agtcgtttcc agtttctaag caaatagatt caacggtctg    600
ggctggcact acaaat                                                     616
```

<210> SEQ ID NO 42
<211> LENGTH: 192
<212> TYPE: DNA
<213> ORGANISM: Artificial Sequence
<220> FEATURE:
<223> OTHER INFORMATION: Sense Sequence Transgene Construct

<400> SEQUENCE: 42

```
tgagagcaag tcaggtcatc cgatggcagc cgctctggtg gactatgcac aatcaaattc     60
cgttgagcca aagcctgata gagttgagca gtttcaaaat tttcctggtg aagggatatt    120
tggaagaatt gatggaatgg aaatctatgt cgggaatagg aaaatttctt caagagctgg    180
atgtaccaca gg                                                        192
```

<210> SEQ ID NO 43
<211> LENGTH: 138
<212> TYPE: DNA
<213> ORGANISM: Artificial Sequence
<220> FEATURE:
<223> OTHER INFORMATION: Space Sequence Transgene Construct

<400> SEQUENCE: 43

```
taaatggttg aatcatttct tatgctcata gtagagataa acatcagag ttataattat      60 aagtatatga tttctccagt taattttgct gttagatttt ctttgacctg tttagcacta    120
atgcggtgga tgtttgaa                                                  138
```

<210> SEQ ID NO 44
<211> LENGTH: 196
<212> TYPE: DNA
<213> ORGANISM: Artificial Sequence
<220> FEATURE:
<223> OTHER INFORMATION: Reverse Complementary Sequence Transgene
      Construct

<400> SEQUENCE: 44

```
cctgtggtac atccagctct tgaagaaatt ttcctattcc cgacatagat ttccattcca     60
tcaattcttc caaatatccc ttcaccagga aaatttgaa actgctcaac tctatcaggc    120
tttggctcaa cggaatttga ttgtgcatag tccaccagag cggctgccat cggatgacct    180
gacttgctct caatgc                                                    196
```

<210> SEQ ID NO 45
<211> LENGTH: 526
<212> TYPE: DNA
<213> ORGANISM: Artificial Sequence
<220> FEATURE:
<223> OTHER INFORMATION: RNAi Sequence

<400> SEQUENCE: 45

```
tgagagcaag tcaggtcatc cgatggcagc cgctctggtg gactatgcac aatcaaattc     60
cgttgagcca aagcctgata gagttgagca gtttcaaaat tttcctggtg aagggatatt    120
tggaagaatt gatggaatgg aaatctatgt cgggaatagg aaaatttctt caagagctgg    180
atgtaccaca ggtaaatggt tgaatcattt cttatgctca gtagagat aaaacatcag      240
```

| | |
|---|---|
| agttataatt ataagtatat gatttctcca gttaattttg ctgttagatt ttctttgacc | 300 |
| tgtttagcac taatgcggtg gatgtttgaa cctgtggtac atccagctct tgaagaaatt | 360 |
| ttcctattcc cgacatagat ttccattcca tcaattcttc caaatatccc ttcaccagga | 420 |
| aaatttgaa actgctcaac tctatcaggc tttggctcaa cggaatttga ttgtgcatag | 480 |
| tccaccagag cggctgccat cggatgacct gacttgctct caatgc | 526 |

<210> SEQ ID NO 46
<211> LENGTH: 4392
<212> TYPE: DNA
<213> ORGANISM: Artificial Sequence
<220> FEATURE:
<223> OTHER INFORMATION: Reverse Complement Sequence

<400> SEQUENCE: 46

| | |
|---|---|
| acgaaacaag tttaatcgtc gagttgaaga acttctattt tatccatcct tcaaatgttg | 60 |
| tatacatgtg aagcctaacg tagatgagat actgttaaag actatttgga ggaggttttg | 120 |
| aacgaggttc cacaaaaaag aaccgtgttg taagaaaaga cttcgacagt gtcgtaggtg | 180 |
| gctacacaga gaagaggttg tcgcttgttt ggaatgctgg tgacgtcaga tccattacta | 240 |
| ctaccaacag ggcattctat aactaccaac tagcttgcca acctggtgta agacgtcgta | 300 |
| cgaaggacgt cggtcttgcc tgcagcaccg taccaaacat aaacgtcgta gaagattggt | 360 |
| cgaaccgatc aagaagtagt caacctcatc aaaatctcac ttcaggtgtc actaaatgga | 420 |
| ctagaaaacc aagtacaaac gtcgacgacc tctactggta cgagacgaaa cacgacagtg | 480 |
| ttactcgtca aagaacttaa agtgaaaaac tatgcagcag ttacggtacc tgaacttgac | 540 |
| tttttgttgt tagtagacaa cgtgttgaca gtatacggaa aagacctaca ctcactagca | 600 |
| caaggaacag gcttgtcggt actggctgtc gtactccact aaaatatgga agaggttgtt | 660 |
| gtaggttcta aaagacgagg ttcaacaaga ggagcacctc acctaatagt acgcttactg | 720 |
| ttggtaccta cgaatctctc aggtcctaga atagtaaagg cgtacagtag ctaggacttg | 780 |
| aacgtcaaac cgtacaaact aaccacgaca gtgttactcg tcaaaggacc taaggtcaaa | 840 |
| gactatgtag tcaaaataac ggaacttggc ttattgttgt aagaacattc cgtgttgaca | 900 |
| gtacggaa cagatttaaa catactagta cagggagcag tctcgtcggt actgcttcta | 960 |
| gtactgaact aaggaataga aaagcctgat ttaggttcga aaagacgagg ctttcgaaaa | 1020 |
| ggggtgactc acctaatcat tcaccactta cttttgacaa gagccaacgt ctcaggaccg | 1080 |
| tgaagaataa agacgtactg gaacttggac ttaatcgtca aaacgtacta cctggtctgt | 1140 |
| agaaacttct cgtactaagt ctcaaccaaa cacttattgt tcttaagaac gataaccaca | 1200 |
| ggctcgtgaa acataaaggt gtacaggacc tcgaacttca acgtctaacc gaaacacctc | 1260 |
| gtgtgttgaa tctgtacgta caaactacta gccctacact tcctaccgat gataacagaa | 1320 |
| aactcagact tgtgaacgat aaaggtgtac taaatctggg tctttgacgt ctaactgtag | 1380 |
| gacctcgtct gaagaaccat ctcgtgcaaa ctccttaaaa cagcctaact gttgtaaaaa | 1440 |
| acagtgactt cagcctcgtg aaccatgaag gtgtactaaa caacgaactt catcgtctta | 1500 |
| ctgtaacacc tcgtctgtag aaccttcttg tatgatctct caatcaattt cttactgtta | 1560 |
| atgagaacac ttacctcaga ctcgttaaca ataaaggtgt actgaaacta agactttcac | 1620 |
| gtctaaccgg acgaaatcgt cggtagaagc tacttgtcgt aactcctgcc cctactctta | 1680 |
| cttttggtga taaaagttg cctcagaccc gtgactaata aaggtgtact gaaactaaga | 1740 |
| ctttgacgtc taaccgtgcg aaatcgtcgg tagaagctgc tcgtcgtaag tcctgcccct | 1800 |

```
actcttactt ttggtgataa aagttgcctc agacccgtga ctaataaagg cgtgctgaaa    1860
ctaagacttt gacgtctaac cgtacgaaat cgtcggtaga agctgctcgt cgtaactcct    1920
gccgctactc ttacttttgg tgataaaagt tacctcagac ccgtgactaa taaaggtgta    1980
ctgaaactag gactcctctg tccaactgta gaaccttgtg tgtggagcct gctcgtacta    2040
actgaacatg taaagaaaac actgagttat agtctcgttg tgtcgacccc tcgtaaaagg    2100
ctgaacgttg tacttcgaaa cagaaacacc accctcgtac gcttcctcat cttctagagg    2160
ttgtaaaaaa gggtacagac gcacacggag gagcatcttc atcgtacgac aagttttagt    2220
gatcgttcgt acagggtcat agacgctcct gtcgtcgggt ttggttacct attggacgat    2280
aacggttacg ttgataccgt cggaaacatt gctgactata ttagtataag agttgttaga    2340
aggaagcttg agaagatcgt tctgcacgtc gaaagccata agaaggctac agtaaacagt    2400
aatcatattg taccggacaa agaaatcgct ctcgactggg tctctacggg taactctacg    2460
gttacagtcg acaacgatta cgtcctcgta gtaattccgg cagcggatag tagcgacaac    2520
ctcgaaggaa gacttttggg aactactaac aacggaacag gagaccatcc tcaagacgaa    2580
ctttaagtag gtttcgaggt ggattgacta ggacgtgtac caaccgtcga cgtattgtta    2640
gtggtcattc gtagcgccaa aactatgggt agacgaagtc aagagagtaa cgaagaaaat    2700
gtggttaagc tgtttgtagc ctttctgact tttaaggtcg acctctacta gggttttat     2760
acataggttg tctgaaagga aactttgata gtgggagata aagaccatga caccatgtag    2820
gtcgagaact tctttaaaag gataagggct gtatctaaag gtaaggtagt taagaaggtt    2880
tatagggaag tggtcctttt aaaactttga cgagttgaga tagtccgaaa ccgagttgcc    2940
ttaaactaac acgtatcagg tggtctcgcc gacggtagcc tactggactg aacgagagtt    3000
acgaactttg ggtcatttcg tcacataact ctgattttgg tagttagtct ctgaacttga    3060
gccagtggta tttaagagga aatcaatatc agggacaaaa cagttttcgg tactaaaact    3120
aaaatcgatc tcagagttcc atgagacgag gaaatttgtc ttctggcctg caacgacgaa    3180
aactttcacg cgttgtgtac cgttgaccac atctatcttg ttcacgtgtg cctgtacgtg    3240
agtggttaca ctggtttcgg ttcgctatgg taagtaaagc taacacttga gaattacgtc    3300
atccttgtta acggtttctt cgactatatc ggtgttaacg accacatatt ataaatcgtg    3360
tgaacagcta catagaaacc caaaaactaa agaacaagac tcgtagaagc tgttcgacac    3420
ggtaggatcg gtggcgtgtt agaagtcggt ttcggcatca gaattgtgac tatatcggta    3480
aatctaaaca tcacggtcgg gtctggcaac ttagagaaac gaatctttga cctttgctga    3540
gcggacagtc acaaaagagc aggtgcagtg taagggaag gtgatgttga ggtagttatc     3600
catatcaaag tggtcgaaag tgtcgttctt acgataagtg gaactgaagt agttgtaaat    3660
gctgaagagg cgaaagtcga ttttgacgac aaccctcctg atataactgg tcactactgt    3720
atcgtcgcca tcggaacact gaacgggaac tgagatcggt aagacgttac cgcttattct    3780
tctgttatca tggtcgaagg gttattagca cattttgtta actaggtcgg tgacgataat    3840
tttgttctta caactacagt tctcactcca aagcgtgccg tcggtgtgga gattttattt    3900
aacctcctta gggttgacgt tgtcgacgtt cacgattggt aaccttttcca cgtttttttca   3960
tgaagttttt actctcaggt tcgttataag gtgacggtta acgttacctt gaaccggtaa    4020
agaaaaccat caaaaagaga ggaaagtgag aatacgaacg aagattagaa cgaactaagt    4080
tacgaaattg ttaaacaacg cctctttact cttctcttag tacttattgt tactgtcaga    4140
aacaacactg ttaatgactt tggagaaatt ggggaagttc taagaactct tgaaaaagtt    4200
```

```
gatcttgttg aagacttcat gtcgtttaag ggttttgtag ttttatcgag aacgagttga   4260
agaaacaaag taagtaaaaa agtgaaaggt ggtaaaaaga ggaagagatt cctcctcctc   4320
ttctattatc tacttttcc ttaaagatca agaccttata taacctatat gaaaacaaaa   4380
cctttctcca ct                                                       4392

<210> SEQ ID NO 47
<211> LENGTH: 4011
<212> TYPE: DNA
<213> ORGANISM: Artificial Sequence
<220> FEATURE:
<223> OTHER INFORMATION: Sense Sequence

<400> SEQUENCE: 47
acgacggcca gtgaattgta atacgactca ctatagggcg aattgggccc tctagatgca     60
tgctcgagcg gccgccagtg tgatggatat ctgcagaatt cgcccttgag gaaacataga    120
aagaagagaa tggtggaaag tgagaaaatg aatgacacaa agaatctgag caagagctat    180
tttgatgttt tgggaatttg ctgtacttca gaagttgttc ttgttgaaaa aattctcaag    240
aatcttgaag gggttaaaga ggtttcagta attgtcacaa caaagactgt cattgttatt    300
catgattctc tcctcatttc tcagcaacaa attgttaaag cattgaatca agcaagatta    360
gaagcaagta taagagtgaa aggagagaaa aactaccaaa agaaatggcc aagtccattt    420
gcaattggca gtggaatatt gcttggactc tcattttga agtactttt tgcacctttc    480 caatggttag cacttgcagc tgttgcagtt gggattcctc caattatttt taggggtgtg    540
gctgccgtgc gaaacctcac tcttgacatc aacattcttg tttttaatagc agtgacggga    600 tcaattgttt tacacgatta ttgggaagct gatactattg tcttcttatt caccattgca    660
gaatggctag agtcaagggc aagtcacaag gctactgctg ctatgtcatc actggtcaat    720
atagtccctc caacagcagt tttagctgaa agtggagaag tcgtaaatgt tgatgaagtc    780
aagttgaata gcattcttgc tgttaaagct ggtgaaacta tacctattga tggagttgta    840
atggaagggg aatgtgacgt ggacgagaaa acactgacag gcgagtcgtt tccagttttct    900 aagcaaatag attcaacggt ctgggctggc actacaaatc taaatggcta tatcagtgtt    960
aagactacgg cttttggctga agattgtgcg gtggctagga tggcgcagct tgtcgaagat   1020
gctcagaaca agaaatcaaa aacccaaaga tacattgaca agtgtgctaa atattataca   1080
ccagcaattg tggctatatc agcttctttg gcaatagttc ctactgcatt aagagttcac   1140
aatcgaaatg agtggtatcg cttggctttg gtcacgttgg tgagtgcatg tccgtgtgca   1200
cttgtgctat ctacaccagt tgccatgtgt tgtgcactt ctaaagcagc aacgtccggt   1260
cttctgttta aaggagcaga gtaccttgag actcttgcta aaatcaaaat catggctttt   1320
gacaaaacag ggactataac tagaggagaa tttatggtga ccgagttcaa gtctctggtt   1380
gatggtcttg gtctcaatac actgctttac tgggtttcaa gtattgagag caagtcaggt   1440
catccgatgg cagccgctct ggttgactat gcacaatcaa attccgttga gccaaagcct   1500
gatagagttg agcagtttca aaattttcct ggtgaaggga tatttggaag aattgatgga   1560
atggaaatct atgtcgggaa taggaaaatt tcttcaagag ctggatgtac tacagtacca   1620
gaaatagagg gtgatagttt ccaaggaaag tctgttggat acatattttt gggatcatct   1680
cccgctggaa ttttcggtct ttccgatgtt tgtcgaattg gtgtaaaaga agcaatgaga   1740
gagctgaagc agatgggtat caaaaccgcg atgcttactg gtgattgtta tgcagctgcc   1800
aaccatgtgc aggatcagtt aggtggagct atggatgaat tcaagcgga actcttacca   1860
```

```
gaggacaagg caacaatcat caagggtttt cagaaggaag ctccaacagc gatgataggc    1920
gacggcctta atgatgctcc tgcattagca acagctgaca ttggcatctc aatgggcatc    1980
tctgggtcag ctctcgcgaa agaaacaggc catgttatac taatgacaaa tgacatcgga    2040
agaataccaa aagctgcacg tcttgctaga agagttcgaa ggaagattgt tgagaatatg    2100
attatatcag tcgttacaaa ggccgccata gttgcattgg caatagcagg ttatccattg    2160
gtttgggctg ctgtcctcgc ggatactggg acatgcttgc tagtgatctt gaacagcatg    2220
ctacttctac gagtaggcac acacagacat gggaaaaaat gttgtagatc tgctactcct    2280
tcgcatgctc ccaaccacaa agacaaagct tcttgttgca agtcggaaaa tgctccgcag    2340
ctgtgttgct ctgatattga gtcacaaaag aaatgtacga gtcaatcatg ctcgtccgag    2400
gtgtgtgttc caagatgcca acctgtctcc tcgggatcaa agtcatgtgg aaataatcag    2460
tgcccagact ccgttgaaaa tagtggtttt cattctcatc cccgtcctct agtatgttct    2520
tccaagatgt ctgctccaca atgtcattct gccacttcaa gctccaaatc atgtggaagt    2580
accaagtgct ccaacttcag tgacaaaaaa tgttgccaat atgacaaaat tcctcaaacg    2640
tgctctacca agaagtctgc tccaggatgt caatctgcag tttctgggtc taaatcatgt    2700
ggagatagca agtgttcaga ctcgaaagac aatagtagcc atccttcaca tcccgatcat    2760
caaatatgca cgtctaagtt gtgtgctcca caaagccaat ctgcaacttc aagctccagg    2820
acatgtggaa atatgaagtg ctcggacacc aatagcaaga attcttgtta ttcacatacc    2880
aactctgaat catgctcttc aaagatgtct ggtccagcat gcaaaactgc taattcaggt    2940
tcaaggttat gcggaaataa gaagtgccta gactctgcaa acgagaacag ttttcattca    3000
cttactaatc cactctgtga ggaaaagctt ttggagaagg aaagcttgga tttagcccga    3060
aaagataggg aatcaaatca tgatcttagt catggttact ctgacgagga acatgatcat    3120
ctaaatttag acaaggcaca tgacagttgt gccttacaag aatgttgtta ttctgttcaa    3180
ggcaataaaa ctgatgtatc agaaactgga atccaggaag ctgctcattg tgacagcatc    3240
aatcaaacat gccaaactgc aatttcagga tcaatgacat gcggaaataa taagagtctg    3300
gactctctaa gcatccatgg ttgtcattca catgatagtc cactccacaa ggagagcaac    3360
ttggagcaga aaagcttgga tgttgctgga aaggtataa atcaccctca tgctgtcggt    3420
caaggctgtt cggacaagga gcacaatcac tcgcatccag aaaaggcgta tgacagttgt    3480
gcaacagacg attgttgttt ttcagttcaa gtccatggca ttgacgacgt atcaagaagt    3540
gaaattcaag aaactgctca ttgtgacagc acaaaacaga gcacggtcat ccccagcagc    3600
tgcgaacatg aaccaaaaga tcaggtaaat cactgtggat ctcactctaa aagtattcca    3660
actgatgaag aactagccaa gctggttaga agatgctgca aatacaaacc atgccacgat    3720
gtccgctctg gctgcaggaa gcatgctgca gaatgtggtc caaccgttcg atcaaccatc    3780
aatatcttac gggacaacca tcatcatcat ctagactgca gtggtcgtaa ggtttgttcg    3840
ctgttggaga agagacacat tggtggatgc tgtgacagct tcagaaaaga atgttgtgcc    3900
aagaacaatc accttggagc aagttttgga ggaggtttat cagaaattgt caagggcga    3960
attccagcac actggcggcc gttactagtg gatccgagct cggtaccaag c            4011

<210> SEQ ID NO 48
<211> LENGTH: 4011
<212> TYPE: DNA
<213> ORGANISM: Artificial Sequence
<220> FEATURE:
<223> OTHER INFORMATION: Reverse Complement Sequence
```

```
<400> SEQUENCE: 48
gcttggtacc gagctcggat ccactagtaa cggccgccag tgtgctggaa ttcgcccttt      60
gacaatttct gataaacctc ctccaaaact tgctccaagg tgattgttct tggcacaaca     120
ttcttttctg aagctgtcac agcatccacc aatgtgtctc ttctccaaca gcgaacaaac     180
cttacgacca ctgcagtcta gatgatgatg atggttgtcc cgtaagatat tgatggttga     240
tcgaacggtt ggaccacatt ctgcagcatg cttcctgcag ccagagcgga catcgtggca     300
tggtttgtat ttgcagcatc ttctaaccag cttggctagt tcttcatcag ttggaatact     360
tttagagtga gatccacagt gatttacctg atcttttggt tcatgttcgc agctgctggg     420
gatgaccgtg ctctgttttg tgctgtcaca atgagcagtt tcttgaattt cacttcttga     480
tacgtcgtca atgccatgga cttgaactga aaaacaacaa tcgtctgttg cacaactgtc     540
atacgccttt tctggatgcg agtgattgtg ctccttgtcc gaacagcctt gaccgacagc     600
atgaggtgat tttataccct ctccagcaac atccaagctt ttctgctcca agttgctctc     660
cttgtggagt ggactatcat gtgaatgaca accatggatg cttagagagt ccagactctt     720
attatttccg catgtcattg atcctgaaat tgcagtttgg catgtttgat tgatgctgtc     780
acaatgagca gcttcctgga ttccagtttc tgatacatca gttttattgc cttgaacaga     840
ataacaacat tcttgtaagg cacaactgtc atgtgccttg tctaaattta gatgatcatg     900
ttcctcgtca gagtaaccat gactaagatc atgatttgat tccctatctt tcgggctaa      960
atccaagctt tccttctcca aaagcttttc ctcacagagt ggattagtaa gtgaatgaaa    1020
actgttctcg tttgcagagt ctaggcactt cttatttccg cataaccttg aacctgaatt    1080
agcagttttg catgctggac cagacatctt tgaagagcat gattcagagt tggtatgtga    1140
ataacaagaa ttcttgctat tggtgtccga gcacttcata tttccacatg tcctggagct    1200
tgaagttgca gattggcttt gtggagcaca caacttagac gtgcatattt gatgatcggg    1260
atgtgaagga tggctactat tgtctttcga gtctgaacac ttgctatctc cacatgattt    1320
agacccagaa actgcagatt gacatcctgg agcagacttc ttggtagagc acgtttgagg    1380
aattttgtca tattggcaac attttttgtc actgaagttg gagcacttgg tacttccaca    1440
tgatttggag cttgaagtgg cagaatgaca ttgtggagca gacatcttgg aagaacatac    1500
tagaggacgg ggatgagaat gaaaaccact attttcaacg gagtctgggc actgattatt    1560
tccacatgac tttgatcccg aggagacagg ttggcatctt ggaacacaca cctcggacga    1620
gcatgattga ctcgtacatt tcttttgtga ctcaatatca gagcaacaca gctgcggagc    1680
attttccgac ttgcaacaag aagctttgtc tttgtggttg ggagcatgcg aaggagtagc    1740
agatctacaa catttttttcc catgtctgtg tgtgcctact cgtagaagta gcatgctgtt   1800
caagatcact agcaagcatg tcccagtatc cgcgaggaca gcagcccaaa ccaatggata    1860
acctgctatt gccaatgcaa ctatggcggc ctttgtaacg actgatataa tcatattctc    1920
aacaatcttc cttcgaactc ttctagcaag acgtgcagct tttggtattc ttccgatgtc    1980
atttgtcatt agtataacat ggcctgtttc tttcgcgaga gctgacccag agatgcccat    2040
tgagatgcca atgtcagctg ttgctaatgc aggagcatca ttaaggccgt cgcctatcat    2100
cgctgttgga gcttccttct gaaaacccctt gatgattgtt gccttgtcct ctggtaagag   2160
ttccgcttga aattcatcca tagctccacc taactgatcc tgcacatggt tggcagctgc    2220
ataacaatca ccagtaagca tcgcggtttt gataccatc tgcttcagct ctctcattgc     2280
ttcttttaca ccaattcgac aaacatcgga aagaccgaaa attccagcgg gagatgatcc    2340
```

```
caaaaatatg tatccaacag actttccttg gaaactatca ccctctattt ctggtactgt    2400
agtacatcca gctcttgaag aaattttcct attcccgaca tagatttcca ttccatcaat    2460
tcttccaaat atcccttcac caggaaaatt ttgaaactgc tcaactctat caggctttgg    2520
ctcaacggaa tttgattgtg catagtcaac cagagcggct gccatcggat gacctgactt    2580
gctctcaata cttgaaaccc agtaaagcag tgtattgaga ccaagaccat caaccagaga    2640
cttgaactcg gtcaccataa attctcctct agttatagtc cctgttttgt caaaagccat    2700
gattttgatt ttagcaagag tctcaaggta ctctgctcct ttaaacagaa gaccggacgt    2760
tgctgcttta gaaagtgcac aacacatggc aactggtgta gatagcacaa gtgcacacgg    2820
acatgcactc accaacgtga ccaaagccaa gcgataccac tcatttcgat tgtgaactct    2880
taatgcagta ggaactattg ccaaagaagc tgatatagcc acaattgctg gtgtataata    2940
tttagcacac ttgtcaatgt atctttgggt ttttgatttc ttgttctgag catcttcgac    3000
aagctgcgcc atcctagcca ccgcacaatc ttcagccaaa gccgtagtct taacactgat    3060
atagccattt agatttgtag tgccagccca gaccgttgaa tctatttgct tagaaactgg    3120
aaacgactcg cctgtcagtg ttttctcgtc cacgtcacat tcccctcca ttacaactcc    3180
atcaataggt atagtttcac cagctttaac agcaagaatg ctattcaact tgacttcatc    3240
aacatttacg acttctccac tttcagctaa aactgctgtt ggagggacta tattgaccag    3300
tgatgacata gcagcagtag cctgtgact tgcccttgac tctagccatt ctgcaatggt    3360
gaataagaag acaatagtat cagcttccca ataatcgtgt aaaacaattg atcccgtcac    3420
tgctattaaa acaagaatgt tgatgtcaag agtgaggttt cgcacggcag ccacacccct    3480
aaaaataatt ggaggaatcc caactgcaac agctgcaagt gctaaccatt ggaaaggtgc    3540
aaaaaagtac ttcaaaaatg agagtccaag caatattcca ctgccaattg caaatggact    3600
tggccatttc ttttggtagt ttttctctcc tttcactctt atacttgctt ctaatcttgc    3660
ttgattcaat gctttaacaa tttgttgctg agaaatgagg agagaatcat gaataacaat    3720
gacagtcttt gttgtgacaa ttactgaaac ctctttaacc ccttcaagat tcttgagaat    3780
tttttcaaca agaacaactt ctgaagtaca gcaaattccc aaaacatcaa aatagctctt    3840
gctcagattc tttgtgtcat tcattttctc actttccacc attctcttct ttctatgttt    3900
cctcaagggc gaattctgca gatatccatc acactggcgg ccgctcgagc atgcatctag    3960
agggcccaat cgccctata gtgagtcgta ttacaattca ctggccgtcg t              4011
```

<210> SEQ ID NO 49
<211> LENGTH: 1325
<212> TYPE: PRT
<213> ORGANISM: Nicotiana tabacum

<400> SEQUENCE: 49

Gly Glu Leu Gly Pro Leu Asp Ala Cys Ser Ser Gly Arg Gln Cys Asp
1               5                   10                  15

Gly Tyr Leu Gln Asn Ser Pro Leu Arg Lys His Arg Lys Lys Arg Met
            20                  25                  30

Val Glu Ser Glu Lys Met Asn Asp Thr Lys Asn Leu Ser Lys Ser Tyr
        35                  40                  45

Phe Asp Val Leu Gly Ile Cys Cys Thr Ser Glu Val Val Leu Val Glu
    50                  55                  60

Lys Ile Leu Lys Asn Leu Glu Gly Val Lys Glu Val Ser Val Ile Val
65                  70                  75                  80

Thr Thr Lys Thr Val Ile Val Ile His Asp Ser Leu Leu Ile Ser Gln

```
                        85                  90                  95
Gln Gln Ile Val Lys Ala Leu Asn Gln Ala Arg Leu Glu Ala Ser Ile
            100                 105                 110

Arg Val Lys Gly Glu Lys Asn Tyr Gln Lys Lys Trp Pro Ser Pro Phe
            115                 120                 125

Ala Ile Gly Ser Gly Ile Leu Leu Gly Leu Ser Phe Leu Lys Tyr Phe
            130                 135                 140

Phe Ala Pro Phe Gln Trp Leu Ala Leu Ala Ala Val Ala Val Gly Ile
145                 150                 155                 160

Pro Pro Ile Ile Phe Arg Gly Val Ala Ala Val Arg Asn Leu Thr Leu
                165                 170                 175

Asp Ile Asn Ile Leu Val Leu Ile Ala Val Thr Gly Ser Ile Val Leu
                180                 185                 190

His Asp Tyr Trp Glu Ala Asp Thr Ile Val Phe Leu Phe Thr Ile Ala
                195                 200                 205

Glu Trp Leu Glu Ser Arg Ala Ser His Lys Ala Thr Ala Ala Met Ser
            210                 215                 220

Ser Leu Val Asn Ile Val Pro Pro Thr Ala Val Leu Ala Glu Ser Gly
225                 230                 235                 240

Glu Val Val Asn Val Asp Glu Val Lys Leu Asn Ser Ile Leu Ala Val
                245                 250                 255

Lys Ala Gly Glu Thr Ile Pro Ile Asp Gly Val Val Met Glu Gly Glu
                260                 265                 270

Cys Asp Val Asp Glu Lys Thr Leu Thr Gly Glu Ser Phe Pro Val Ser
            275                 280                 285

Lys Gln Ile Asp Ser Thr Val Trp Ala Gly Thr Thr Asn Leu Asn Gly
            290                 295                 300

Tyr Ile Ser Val Lys Thr Thr Ala Leu Ala Glu Asp Cys Ala Val Ala
305                 310                 315                 320

Arg Met Ala Gln Leu Val Glu Asp Ala Gln Asn Lys Lys Ser Lys Thr
                325                 330                 335

Gln Arg Tyr Ile Asp Lys Cys Ala Lys Tyr Tyr Thr Pro Ala Ile Val
            340                 345                 350

Ala Ile Ser Ala Ser Leu Ala Ile Val Pro Thr Ala Leu Arg Val His
            355                 360                 365

Asn Arg Asn Glu Trp Tyr Arg Leu Ala Leu Val Thr Leu Val Ser Ala
            370                 375                 380

Cys Pro Cys Ala Leu Val Leu Ser Thr Pro Val Ala Met Cys Cys Ala
385                 390                 395                 400

Leu Ser Lys Ala Ala Thr Ser Gly Leu Leu Phe Lys Gly Ala Glu Tyr
                405                 410                 415

Leu Glu Thr Leu Ala Lys Ile Lys Ile Met Ala Phe Asp Lys Thr Gly
            420                 425                 430

Thr Ile Thr Arg Gly Glu Phe Met Val Thr Glu Phe Lys Ser Leu Val
            435                 440                 445

Asp Gly Leu Gly Leu Asn Thr Leu Leu Tyr Trp Val Ser Ser Ile Glu
            450                 455                 460

Ser Lys Ser Gly His Pro Met Ala Ala Ala Leu Val Asp Tyr Ala Gln
465                 470                 475                 480

Ser Asn Ser Val Glu Pro Lys Pro Asp Arg Val Glu Gln Phe Gln Asn
                485                 490                 495

Phe Pro Gly Glu Gly Ile Phe Gly Arg Ile Asp Gly Met Glu Ile Tyr
            500                 505                 510
```

-continued

```
Val Gly Asn Arg Lys Ile Ser Ser Arg Ala Gly Cys Thr Val Pro
            515                 520                 525

Glu Ile Glu Gly Asp Ser Phe Gln Gly Lys Ser Val Gly Tyr Ile Phe
        530                 535                 540

Leu Gly Ser Ser Pro Ala Gly Ile Phe Gly Leu Ser Asp Val Cys Arg
545                 550                 555                 560

Ile Gly Val Lys Glu Ala Met Arg Glu Leu Lys Gln Met Gly Ile Lys
            565                 570                 575

Thr Ala Met Leu Thr Gly Asp Cys Tyr Ala Ala Ala Asn His Val Gln
                580                 585                 590

Asp Gln Leu Gly Gly Ala Met Asp Glu Phe Gln Ala Glu Leu Leu Pro
            595                 600                 605

Glu Asp Lys Ala Thr Ile Ile Lys Gly Phe Gln Lys Glu Ala Pro Thr
        610                 615                 620

Ala Met Ile Gly Asp Gly Leu Asn Asp Ala Pro Ala Leu Ala Thr Ala
625                 630                 635                 640

Asp Ile Gly Ile Ser Met Gly Ile Ser Gly Ser Ala Leu Ala Lys Glu
            645                 650                 655

Thr Gly His Val Ile Leu Met Thr Asn Asp Ile Gly Arg Ile Pro Lys
                660                 665                 670

Ala Ala Arg Leu Ala Arg Arg Val Arg Arg Lys Ile Val Glu Asn Met
            675                 680                 685

Ile Ile Ser Val Val Thr Lys Ala Ala Ile Val Ala Leu Ala Ile Ala
            690                 695                 700

Gly Tyr Pro Leu Val Trp Ala Ala Val Leu Ala Asp Thr Gly Thr Cys
705                 710                 715                 720

Leu Leu Val Ile Leu Asn Ser Met Leu Leu Leu Arg Val Gly Thr His
                725                 730                 735

Arg His Gly Lys Lys Cys Cys Arg Ser Ala Thr Pro Ser His Ala Pro
            740                 745                 750

Asn His Lys Asp Lys Ala Ser Cys Cys Lys Ser Glu Asn Ala Pro Gln
        755                 760                 765

Leu Cys Cys Ser Asp Ile Glu Ser Gln Lys Lys Cys Thr Ser Gln Ser
    770                 775                 780

Cys Ser Ser Glu Val Cys Val Pro Arg Cys Gln Pro Val Ser Ser Gly
785                 790                 795                 800

Ser Lys Ser Cys Gly Asn Asn Gln Cys Pro Asp Ser Val Glu Asn Ser
            805                 810                 815

Gly Phe His Ser His Pro Arg Pro Leu Val Cys Ser Ser Lys Met Ser
                820                 825                 830

Ala Pro Gln Cys His Ser Ala Thr Ser Ser Ser Lys Ser Cys Gly Ser
            835                 840                 845

Thr Lys Cys Ser Asn Phe Ser Asp Lys Lys Cys Cys Gln Tyr Asp Lys
        850                 855                 860

Ile Pro Gln Thr Cys Ser Thr Lys Lys Ser Ala Pro Gly Cys Gln Ser
865                 870                 875                 880

Ala Val Ser Gly Ser Lys Ser Cys Gly Asp Ser Lys Cys Ser Asp Ser
            885                 890                 895

Lys Asp Asn Ser Ser His Pro Ser His Pro Asp His Gln Ile Cys Thr
                900                 905                 910

Ser Lys Leu Cys Ala Pro Gln Ser Gln Ser Ala Thr Ser Ser Ser Arg
            915                 920                 925
```

-continued

```
Thr Cys Gly Asn Met Lys Cys Ser Asp Thr Asn Ser Lys Asn Ser Cys
    930                 935                 940

Tyr Ser His Thr Asn Ser Glu Ser Cys Ser Ser Lys Met Ser Gly Pro
945                 950                 955                 960

Ala Cys Lys Thr Ala Asn Ser Gly Ser Arg Leu Cys Gly Asn Lys Lys
                965                 970                 975

Cys Leu Asp Ser Ala Asn Glu Asn Ser Phe His Ser Leu Thr Asn Pro
                980                 985                 990

Leu Cys Glu Glu Lys Leu Leu Glu Lys Glu Ser Leu Asp Leu Ala Arg
            995                1000                1005

Lys Asp Arg Glu Ser Asn His Asp Leu Ser His Gly Tyr Ser Asp
    1010                1015                1020

Glu Glu His Asp His Leu Asn Leu Asp Lys Ala His Asp Ser Cys
    1025                1030                1035

Ala Leu Gln Glu Cys Cys Tyr Ser Val Gln Gly Asn Lys Thr Asp
    1040                1045                1050

Val Ser Glu Thr Gly Ile Gln Glu Ala Ala His Cys Asp Ser Ile
    1055                1060                1065

Asn Gln Thr Cys Gln Thr Ala Ile Ser Gly Ser Met Thr Cys Gly
    1070                1075                1080

Asn Asn Lys Ser Leu Asp Ser Leu Ser Ile His Gly Cys His Ser
    1085                1090                1095

His Asp Ser Pro Leu His Lys Glu Ser Asn Leu Glu Gln Lys Ser
    1100                1105                1110

Leu Asp Val Ala Gly Glu Gly Ile Lys Ser Pro His Ala Val Gly
    1115                1120                1125

Gln Gly Cys Ser Asp Lys Glu His Asn His Ser His Pro Glu Lys
    1130                1135                1140

Ala Tyr Asp Ser Cys Ala Thr Asp Asp Cys Cys Phe Ser Val Gln
    1145                1150                1155

Val His Gly Ile Asp Asp Val Ser Arg Ser Glu Ile Gln Glu Thr
    1160                1165                1170

Ala His Cys Asp Ser Thr Lys Gln Ser Thr Val Ile Pro Ser Ser
    1175                1180                1185

Cys Glu His Glu Pro Lys Asp Gln Val Asn His Cys Gly Ser His
    1190                1195                1200

Ser Lys Ser Ile Pro Thr Asp Glu Glu Leu Ala Lys Leu Val Arg
    1205                1210                1215

Arg Cys Cys Lys Tyr Lys Pro Cys His Asp Val Arg Ser Gly Cys
    1220                1225                1230

Arg Lys His Ala Ala Glu Cys Gly Pro Thr Val Arg Ser Thr Ile
    1235                1240                1245

Asn Ile Leu Arg Asp Asn His His His Leu Asp Cys Ser Gly
    1250                1255                1260

Arg Lys Val Cys Ser Leu Leu Glu Lys Arg His Ile Gly Gly Cys
    1265                1270                1275

Cys Asp Ser Phe Arg Lys Glu Cys Cys Ala Lys Asn Asn His Leu
    1280                1285                1290

Gly Ala Ser Phe Gly Gly Leu Ser Glu Ile Val Lys Gly Arg
    1295                1300                1305

Ile Pro Ala His Trp Arg Pro Leu Leu Val Asp Pro Ser Ser Val
    1310                1315                1320

Pro Ser
    1325
```

```
<210> SEQ ID NO 50
<211> LENGTH: 9
<212> TYPE: DNA
<213> ORGANISM: Artificial Sequence
<220> FEATURE:
<223> OTHER INFORMATION: Primer

<400> SEQUENCE: 50 taatccggt                                                                9

<210> SEQ ID NO 51
<211> LENGTH: 9
<212> TYPE: RNA
<213> ORGANISM: Artificial Sequence
<220> FEATURE:
<223> OTHER INFORMATION: Primer

<400> SEQUENCE: 51 uaauccggu                                                                9

<210> SEQ ID NO 52
<211> LENGTH: 9
<212> TYPE: DNA
<213> ORGANISM: Artificial Sequence
<220> FEATURE:
<223> OTHER INFORMATION: Primer

<400> SEQUENCE: 52 taatccggt                                                                9

<210> SEQ ID NO 53
<211> LENGTH: 9
<212> TYPE: DNA
<213> ORGANISM: Artificial Sequence
<220> FEATURE:
<223> OTHER INFORMATION: Primer

<400> SEQUENCE: 53 accggatta                                                                9

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
attctagact gctgctatgt catcactgg                                         29

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
ataagcttag cctgaagaat tgagcaaa                                          28

<210> SEQ ID NO 56
<211> LENGTH: 31
<212> TYPE: DNA
<213> ORGANISM: Artificial Sequence
<220> FEATURE:
<223> OTHER INFORMATION: Primer
```

```
<400> SEQUENCE: 56
atgagctctg gttatgtagg ctactgctgc t                              31

<210> SEQ ID NO 57
<211> LENGTH: 28
<212> TYPE: DNA
<213> ORGANISM: Artificial Sequence
<220> FEATURE:
<223> OTHER INFORMATION: Primer

<400> SEQUENCE: 57
atactagtat ttgtagtgcc agcccaga                                  28

<210> SEQ ID NO 58
<211> LENGTH: 29
<212> TYPE: DNA
<213> ORGANISM: Artificial Sequence
<220> FEATURE:
<223> OTHER INFORMATION: Primer

<400> SEQUENCE: 58
attctagatg agagcaagtc aggtcatcc                                 29

<210> SEQ ID NO 59
<211> LENGTH: 28
<212> TYPE: DNA
<213> ORGANISM: Artificial Sequence
<220> FEATURE:
<223> OTHER INFORMATION: Primer

<400> SEQUENCE: 59
ataagctttt caaacatcca ccgcatta                                  28

<210> SEQ ID NO 60
<211> LENGTH: 29
<212> TYPE: DNA
<213> ORGANISM: Artificial Sequence
<220> FEATURE:
<223> OTHER INFORMATION: Primer

<400> SEQUENCE: 60
atgagctcgc attgagagca agtcaggtc                                 29

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
atctgcagcc tgtggtacat ccagctctt                                 29
```

TRANSGENIC PLANTS MODIFIED FOR REDUCED CADMIUM TRANSPORT, DERIVATIVE PRODUCTS, AND RELATED METHODS

CROSS-REFERENCE TO RELATED APPLICATION

This application claims priority under 35 U.S.C. §119 to U.S. Provisional Application No. 60/996,982, filed Dec. 13, 2007, the entire content of which is hereby incorporated by reference.

SEQUENCE LISTING

This application hereby incorporates by reference the text file filed electronically herewith having the name "sequencelisting.txt" created on Nov. 20, 2008 with a file size of 125,091 bytes.

TECHNICAL FIELD

Compositions, expression vectors, polynucleotides, polypeptides, transgenic plants, transgenic cell lines, and transgenic seeds, and methods for making and using these embodiments to produce various plants that can reduce the transport of heavy metals into aerial portions.

BACKGROUND

Plants obtain essential heavy metals, such as Zn, Ni, and Cu, by absorbing metal ion substrates from their environment by various transport mechanisms mediated by transmembrane transporters expressed on the surface of root cells and other vascular tissues. Transporters classified as P-type ATPases, such as P1B-type ATPases, are transporters that translocate positively charged substrates across plasma membranes by utilizing energy liberated from exergonic ATP hydrolysis reactions. P1B-type ATPases are also referred to as heavy metal ATP-ases ("HMAs") or CPx-type ATPases. HMAs have been grouped by substrate specificity into two subclasses, the Cu/Ag and Zn/Co/Cd/Pb groups. The first P1B-type ATPase to be characterized in plants is AtHMA4, cloned from *Arabidopsis*. Substrate selectivity by HMAs is not strictly limited to the transport of essential metals in that several non-essential metals can be recognized indiscriminantly as substrates, resulting in the accumulation of many non-essential metals, such as Cd, Pb, As, and Hg.

SUMMARY

Various embodiments are directed to compositions and methods for producing transgenic plants, including transgenic tobacco plants, genetically modified to impede Cadmium (Cd) transport from the root system to the leaf lamina by reducing the expression levels of transporters of the HMA family. A HMA homologue ("NtHMA") has been identified in tobacco, which can be utilized for constructing various RNAi constructs, encoding NtHMA RNAi polynucleotides of interest that can facilitate the degradation of endogenous NtHMA RNA transcripts. Transgenic plants that can express NtHMA RNAi polynucleotides can be utilized for reducing steady-state levels of NtHMA RNA transcripts, and consequently, for reducing the number of functionally active NtHMA transporters available for transporting metals across cellular membranes.

Various embodiments are directed to recombinant expression vectors comprising various NtHMA RNAi constructs, transgenic plants and seeds genetically modified to exogenously express NtHMA RNAi polynucleotides, cell lines derived from transgenic plants and seeds, and consumable products incorporating leaves derived from transgenic plants produced according to the disclosed methods.

BRIEF DESCRIPTION OF THE DRAWINGS

FIG. 3A shows an exemplary RNAi sequence, NtHMA (660-915), for producing NtHMA RNAi polynucleotides of interest, as described in Example 2.

FIGS. 3B-3D show Cd reduction in leaf lamina of multiple first generation (T0) transgenic lines, representing three varieties, that have been genetically modified to express NtHMA RNAi polynucleotides (660-915), as described in Example 5.

FIG. 4A shows an exemplary RNAi sequence, NtHMA (1382-1584), for producing NtHMA RNAi polynucleotides of interest, as described in Example 3.

FIGS. 4B-4D show Cd reduction in leaf lamina of multiple first generation (T0) transgenic lines, representing three varieties, that have been genetically modified to express NtHMA RNAi polynucleotides (1382-1584), as described in Example 5.

DETAILED DESCRIPTION

I. Isolation of Tobacco NtHMA Genes and Gene Products

Figures 1A, 1B:
FIG. 1A is a schematic of a NtHMA genomic clone comprising 11 exons.
FIG. 1B provides a list of nucleotide positions mapped to each exon within the isolated NtHMA genomic clone ("Table 1").

FIG. 1A is a schematic of a NtHMA genomic clone comprising 11 exons encoding a heavy metal transporter related to the HMA family of transporters. Example 1 further describes the identification of the NtHMA genomic clone (_HO-18-2) and 4 NtHMA cDNA clones. FIG. 1B. provides nucleotide positions corresponding to exon and intron subregions mapped within the NtHMA genomic clone (_HO-18-2).

A. NtHMA Polynucleotides

The term "polynucleotide" refers to a polymer of nucleotides comprising at least 10 bases in length. The polynucleotides may be DNA, RNA or a DNA/RNA hybrid, comprising ribonucleotides, deoxyribonucleotides, combinations of deoxyribo- and ribo-nucleotides, and combinations of bases and/or modifications, including uracil, adenine, thymine, cytosine, guanine, inosine, xanthine, hypoxanthine, isocytosine, and isoguanine. The term includes single- and double-stranded forms of DNA or RNA. The term "DNA" includes genomic DNAs, cDNAs, chemically-synthesized DNAs, PCR-amplified DNAs, and combinations/equivalents thereof. The term "isolated polynucleotide" refers to a polynucleotide not contiguous with any genome of origin, or separated from a native context. The term includes any recombinant polynucleotide molecule such as NtHMA RNAi constructs, NtHMA RNAi expression vectors, NtHMA genomic clones, and fragments and variants thereof.

As shown in FIG. 1A, the NtHMA genomic clone, designated as SEQ ID NO:1, comprises: intron 1 (SEQ ID NO:4), exon 1 (SEQ ID NO:5), intron 2 (SEQ ID NO:6), exon 2 (SEQ ID NO:7), intron 3 (SEQ ID NO:8), exon 3 (SEQ ID NO:9), intron 4 (SEQ ID NO:10), exon 4 (SEQ ID NO:11), intron 5 (SEQ ID NO:12), exon 5 (SEQ ID NO:13), intron 6 (SEQ ID NO:14), exon 6 (SEQ ID NO:15), intron 7 (SEQ ID NO:16), exon 7 (SEQ ID NO:17), intron 8 (SEQ ID NO:18), exon 8 (SEQ ID NO:19), intron 9 (SEQ ID NO:20), exon 9 (SEQ ID NO:21), intron 10 (SEQ ID NO:22), exon 10 (SEQ ID NO:23), intron 11 (SEQ ID NO:24), exon 11 (SEQ ID NO:25), and intron 12 (SEQ ID NO:26). Various embodiments are directed to isolated polynucleotides representing genomic fragments isolated at the NtHMA locus, comprising SEQ ID NO:1, fragments of SEQ ID NO:1, or variants thereof. Various embodiments are directed to isolated NtHMA polynucleotide variants comprising at least 50%, 55%, 60%, 65%, 70%, 75%, 80%, 85%, 90%, 95%, 96%, 97%, 98%, and 99% sequence identity to SEQ ID NO:1, or fragments of SEQ ID NO:1.

Various embodiments are directed to isolated polynucleotides having sequences that complements that of NtHMA polynucleotide variants comprising at least 50%, 55%, 60%, 65%, 70%, 75%, 80%, 85%, 90%, 95%, 96%, 97%, 98%, and 99% sequence identity to SEQ ID NO:1, or fragments of SEQ ID NO:1. Various embodiments are directed to isolated polynucleotides that can specifically hybridize, under moderate to highly stringent conditions, to polynucleotides comprising SEQ ID NO:1, or fragments of SEQ ID NO:1.

Various embodiments are directed to isolated polynucleotides of NtHMA cDNA (Clone P6663), comprising SEQ ID NO:3, fragments of SEQ ID NO:3, or variants thereof. Various embodiments are directed to isolated NtHMA polynucleotide variants comprising at least 70%, 75%, 80%, 85%, 90%, 95%, 96%, 97%, 98%, and 99% sequence identity to SEQ ID NO:3, or fragments of SEQ ID NO:3. Various embodiments are directed to isolated NtHMA polyribonucleotide variants comprising at least 70%, 75%, 80%, 85%, 90%, 95%, 96%, 97%, 98%, and 99% sequence identity to SEQ ID NO:3, or fragments of SEQ ID NO:3, and in which Ts have been substituted with Us (e.g., RNAs). Various embodiments are directed to isolated polynucleotides that can specifically hybridize, under moderate to highly stringent conditions, to polynucleotides comprising SEQ ID NO:3, or fragments of SEQ ID NO:3. Various embodiments are directed to isolated polynucleotides having a sequence that complements that of NtHMA polynucleotide variants comprising at least 70%, 75%, 80%, 85%, 90%, 95%, 96%, 97%, 98%, and 99% sequence identity to SEQ ID NO:3, or fragments of SEQ ID NO:3.

Various embodiments are directed to isolated polynucleotides of NtHMA cDNA (Clone P6643), comprising SEQ ID NO:47, fragments of SEQ ID NO:47, or variants thereof. Various embodiments are directed to isolated NtHMA polynucleotide variants comprising at least 70%, 75%, 80%, 85%, 90%, 95%, 96%, 97%, 98%, and 99% sequence identity to SEQ ID NO:47, fragments of SEQ ID NO:47. Various embodiments are directed to isolated NtHMA polyribonucleotide variants comprising at least 70%, 75%, 80%, 85%, 90%, 95%, 96%, 97%, 98%, and 99% sequence identity to SEQ ID NO:47, fragments of SEQ ID NO:47, and in which Ts have been substituted with Us (e.g., RNAs). Various embodiments are directed to isolated polynucleotides that can specifically hybridize, under moderate to highly stringent conditions, to polynucleotides comprising SEQ ID NO:47, fragments of SEQ ID NO:47. Various embodiments are directed to isolated polynucleotides having a sequence that complements that of NtHMA polynucleotide variants comprising at least 70%, 75%, 80%, 85%, 90%, 95%, 96%, 97%, 98%, and 99% sequence identity to SEQ ID NO:47, fragments of SEQ ID NO:47.

Various embodiments are directed to biopolymers that are homologous to NtHMA polynucleotides and NtHMA polypeptides ("NtHMA homologues"), which can be identified from different plant species. For example, NtHMA homologues can be experimentally isolated by screening suitable nucleic acid libraries derived from different plant species of interest. Alternatively, NtHMA homologues may be identified by screening genome databases containing sequences from one or more species utilizing a sequence derived from NtHMA polynucleotides and/or NtHMA polypeptides. Such genomic databases are readily available for a number of species (e.g., on the world wide web (www) at tigr.org/tdb; genetics.wisc.edu; stanford.edu/.about.ball; hiv-web.lan1.gov; ncbi.nlm.nig.gov; ebi.ac.uk; and pasteur.fr/other/biology). For example, degenerate oligonucleotide sequences can be obtained by "back-translation" from NtHMA polypeptide fragments. NtHMA polynucleotides can be utilized as probes or primers to identify/amplify related sequences, or to obtain full-length sequences for related NtHMAs by PCR, for example, or by other well-known techniques (e.g., see PCR Protocols: A Guide to Methods and Applications, Innis et. al., eds., Academic Press, Inc. (1990)).

B. NtHMA Polypeptides

The term "NtHMA polypeptide" refers to a polypeptide comprising an amino acid sequence designated as SEQ ID NO:2; polypeptides having substantial homology (i.e., sequence similarity) or substantial identity to SEQ ID NO:2; fragments of SEQ ID NO:2; and variants thereof. The NtHMA polypeptides include sequences having sufficient or substantial degree of identity or similarity to SEQ ID NO:2, and that can function by transporting heavy metals across cell membranes.

NtHMA polypeptides include variants produced by introducing any type of alterations (e.g., insertions, deletions, or substitutions of amino acids; changes in glycosylation states; changes that affect refolding or isomerizations, three-dimensional structures, or self-association states), which can be deliberately engineered or isolated naturally. NtHMA polypeptides may be in linear form or cyclized using known methods (e.g., H. U. Saragovi, et al., Bio/Technology 10, 773 (1992); and R. S. McDowell, et al., J. Amer. Chem. Soc. 114:9245 (1992), both incorporated herein by reference).

NtHMA polypeptides comprise at least 8 to 10, at least 20, at least 30, or at least 40 contiguous amino acids.

Various embodiments are directed to isolated NtHMA polypeptides encoded by polynucleotide sequence, SEQ ID NO:1, comprising SEQ ID NO:2, fragments of SEQ ID NO:2, or variants thereof. Various embodiments are directed to isolated NtHMA polypeptide variants comprising at least 70%, 75%, 80%, 85%, 90%, 95%, 96%, 97%, 98%, and 99% sequence identity to SEQ ID NO:2, or fragments of SEQ ID NO:2.

Various embodiments are directed to isolated NtHMA polypeptides (Clone P6663), comprising SEQ ID NO:2, fragments of SEQ ID NO:2, or variants thereof. Various embodiments are directed to isolated NtHMA polypeptide variants comprising at least 70%, 75%, 80%, 85%, 90%, 95%, 96%, 97%, 98%, and 99% sequence identity to SEQ ID NO:2, or fragments of SEQ ID NO:2.

Various embodiments are directed to isolated NtHMA polypeptides (Clone P6643), comprising SEQ ID NO:49, fragments of SEQ ID NO:49, or variants thereof. Various embodiments are directed to isolated NtHMA polypeptide variants comprising at least 70%, 75%, 80%, 85%, 90%, 95%, 96%, 97%, 98%, and 99% sequence identity to SEQ ID NO:49, or fragments of SEQ ID NO:49.

II. Compositions and Related Methods for Reducing NtHMA Gene Expression and/or NtHMA-Mediated Transporter Activity Suitable antagonistic compositions that can down-regulate the expression and/or the activity of NtHMA and NtHMA variants include sequence-specific polynucleotides that can interfere with the transcription of one or more endogenous NtHMA gene(s); sequence-specific polynucleotides that can interfere with the translation of NtHMA RNA transcripts (e.g., dsRNAs, siRNAs, ribozymes); sequence-specific polypeptides that can interfere with the protein stability of NtHMA, the enzymatic activity of NtHMA, and/or the binding activity of NtHMA with respect to substrates and/or regulatory proteins; antibodies that exhibit specificity for NtHMA; and small molecule compounds that can interfere with the protein stability of NtHMA, the enzymatic activity of NtHMA, and/or the binding activity of NtHMA. An effective antagonist can reduce heavy metal (e.g., Cd) transport into leaf lamina structures by at least 5%, 10%, 15%, 20%, 25%, 30%, 35%, 40%, 45%, 50%, 55%, 60%, 65%, 70%, 75%, 80%, 85%, 90%, or 95%.

A. Definitions

Throughout this disclosure and the appended claims, the terms "a" and "the" function as singular and plural referents unless the context clearly dictates otherwise. Thus, for example, a reference to "an RNAi polynucleotide" includes a plurality of such RNAi polynucleotides, and a reference to "the plant" includes reference to one or more of such plants.

The term "orientation" refers to a particular order in the placement of a polynucleotide relative to the position of a reference polynucleotide. A linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand.

The term "NtHMA RNAi expression vector" refers to a nucleic acid vehicle that comprises a combination of DNA components for enabling the transport and the expression of NtHMA RNAi constructs. Suitable expression vectors include episomes capable of extra-chromosomal replication such as circular, double-stranded DNA plasmids; linearized double-stranded DNA plasmids; and other functionally equivalent expression vectors of any origin. A suitable NtHMA RNAi expression vector comprises at least a promoter positioned upstream and operably-linked to a NtHMA RNAi construct, as defined below.

The term "NtHMA RNAi construct" refers to a double-stranded, recombinant DNA fragment that encodes "NtHMA RNAi polynucleotides" having RNA interference activity. A NtHMA RNAi construct comprises a "template strand" base-paired with a complementary "sense or coding strand." A given NtHMA RNAi construct can be inserted into a NtHMA RNAi expression vector in two possible orientations, either in the same (or sense) orientation or in the reverse (or anti-sense) orientation with respect to the orientation of a promoter positioned within a NtHMA RNAi expression vector.

The term "NtHMA RNAi polynucleotides" can target NtHMA RNA for enzymatic degradation, involving the formation of smaller fragments of NtHMA RNAi polynucleotides ("siRNAs") that can bind to multiple complementary sequences within the target NtHMA RNA. Expression levels of one or more NtHMA gene(s) can be reduced by the RNA interference activity of NtHMA RNAi polynucleotides.

The term "template strand" refers to the strand comprising a sequence that complements that of the "sense or coding strand" of a DNA duplex, such as NtHMA genomic fragment, NtHMA cDNA, or NtHMA RNAi construct, or any DNA fragment comprising a nucleic acid sequence that can be transcribed by RNA polymerase. During transcription, RNA polymerase can translocate along the template strand in the 3'-to-5' direction during nacent RNA synthesis.

The terms "sense strand" or "coding strand" refer to the strand comprising a sequence that complements that of the template strand in a DNA duplex. For example, the sequence of the sense strand ("sense sequence") for the identified NtHMA genomic clone is designated as SEQ ID NO:1. For example, the sense sequence for NtHMA cDNA, identified as clone P6663, is designated as SEQ ID NO:3. For example, the sense sequence for NtHMA cDNA, identified as clone P6643, is designated as SEQ ID NO:46. For example, if the sense strand comprises a hypothetical sequence 5'-TAATCCGGT-3' (SEQ ID NO:50), then the substantially identical corresponding sequence within a hypothetical target mRNA is 5'-UAAUCCGGU-3' (SEQ ID NO:51).

The term "reverse complementary sequence" refers to the sequence that complements the "sense sequence" of interest (e.g., exon sequence) positioned within the same strand, in the same orientation with respect to the sense sequence. For example, if a strand comprises a hypothetical sequence 5'-TAATCCGGT-3' (SEQ ID NO:52), then the reverse complementary sequence 5'-ACCGGATTA-3' (SEQ ID NO:53) may be operably-linked to the sense sequence, separated by a spacer sequence.

The terms "NtHMA RNA transcript" or "NtHMA RNA," in the context of RNA interference, refer to polyribonucleic acid molecules produced within a host plant cell of interest, resulting from the transcription of endogenous genes of the HMA family, including the isolated NtHMA gene (SEQ ID NO:1). Thus, these terms include any RNA species or RNA variants produced as transcriptional products from HMA-related genes that may be distinct from the isolated NtHMA gene (SEQ ID NO:1) but having sufficient similarity at structural and/or functional levels to be classified within the same family. For example, if a host plant cell selected for genetic modification according to the disclosed methods is tobacco, then target NtHMA RNA transcripts include: (1) pre-mRNAs and mRNAs produced from the transcription of the isolated NtHMA gene (SEQ ID NO:1); (2) pre-mRNAs and mRNAs produced from the transcription of any genes having at least 50%, 55%, 60%, 65%, 70%, 75%, 80%, 85%, 90%, 95%, 96%, 97%, 98%, and 99% sequence identity to the sequence of the isolated NtHMA gene (SEQ ID NO:1) (i.e. other distinct genes substantially identical to the identified NtHMA gene and encoding related isoforms of HMA transporters); and (3) pre-mRNAs and mRNAs produced from the transcription of alleles of the NtHMA gene (SEQ ID NO:1). The NtHMA RNA transcripts include RNA variants produced as a result of alternative RNA splicing reactions of heteronuclear RNAs ("hnRNAs") of a particular NtHMA gene, mRNA variants resulting from such alternative RNA splicing reactions, and any intermediate RNA variants.

The terms "homology" or "identity" or "similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). Typical default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Various programs known to persons skilled in the art of sequence comparison can be alternatively utilized.

The term "upstream" refers to a relative direction/position with respect to a reference element along a linear polynucleotide sequence, which indicates a direction/position towards the 5' end of the polynucleotide sequence. "Upstream" may be used interchangeably with the "5' end of a reference element."

The term "operably-linked" refers to the joining of distinct DNA elements, fragments, or sequences to produce a functional transcriptional unit or a functional expression vector.

The term "promoter" refers to a nucleic acid element/sequence, typically positioned upstream and operably-linked to a double-stranded DNA fragment, such as a NtHMA RNAi construct. For example, a suitable promoter enables the transcriptional activation of a NtHMA RNAi construct by recruiting the transcriptional complex, including the RNA polymerase and various factors, to initiate RNA synthesis. "Promoters" can be derived entirely from regions proximate to a native gene of interest, or can be composed of different elements derived from different native promoters and/or synthetic DNA segments. Suitable promoters include tissue-specific promoters recognized by tissue-specific factors present in different tissues or cell types (e.g., root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling NtHMA RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters, as described in a number of references, such as Okamuro and Goldberg, Biochemistry of Plants, Vol. 15: pp 1-82 (1989).

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, e.g., roots or leaves, or reproductive tissues, such as fruit, ovules, seeds, pollen, pistols, flowers, or any embryonic tissue. Reproductive tissue-specific promoters may be, e.g., anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (e.g., the tomato RBCS 1, RBCS2 and RBCS3A genes expressed in leaves and light-grown seedlings, RBCS1 and RBCS2 expressed in developing tomato fruits, and/or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Such promoters are known in the art or can be discovered by known techniques; see, e.g., Bhalla and Singh (1999) Molecular control of male fertility in *Brassica*, Proc. 10th Annual Rapeseed Congress, Canberra, Australia; van Tunen et al. (1990) Pollen- and anther-specific chi promoters from petunia: tandem promoter regulation of the chiA gene. Plant Cell 2:393-40; Jeon et al. (1999) Isolation and characterization of an anther-specific gene, RA8, from rice (*Oryza sativa* L). Plant Molecular Biology 39:35-44; and Twell et al. (1993) Activation and developmental regulation of an *Arabidopsis* anther-specific promoter in microspores and pollen of *Nicotiana tabacum*. Sex. Plant Reprod. 6:217-224.

Suitable root-preferred promoters known to persons skilled in the art may be selected. See, for example, Hire et al. (1992) Plant Mol. Biol. 20(2):207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3(1):11-22 (full-length cDNA clone encoding cytosolic glutamine synthetase (GS), which is expressed in roots and root nodules of soybean). See also Bogusz et al. (1990) Plant Cell 2(7):633-641, where two root-specific promoters isolated from hemoglobin genes from the nitrogen-fixing nonlegume *Parasponia andersonii* and the related non-nitrogen-fixing nonlegume *Trema tomentosa* are described.

Suitable seed-preferred promoters include both seed-specific promoters (those promoters active during seed development such as promoters of seed storage proteins) and seed-germinating promoters (those promoters active during seed germination). See, e.g., Thompson et al. (1989) BioEssays 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40 (U.S. Pat. No. 6,403,862); nuclc (U.S. Pat. No. 6,407,315); and celA (cellulose synthase) (see WO 00/11177). Gama-zein is an endosperm-specific promoter. Glob-1 is an embryo-specific promoter. For dicots, seed-specific promoters include, but are not limited to, bean .beta.-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa γ-zein promoter (such as gzw64A promoter, see Genbank Accession #S78780), a waxy promoter, a shrunken 1 promoter, a shrunken 2 promoter, a globulin 1 promoter (see Genbank Accession # L22344), an ltp2 promoter (Kalla, et al., Plant Journal 6:849-860 (1994)); U.S. Pat. No. 5,525, 716), cim1 promoter (see U.S. Pat. No. 6,225,529) maize end1 and end2 promoters (See U.S. Pat. Nos. 6,528,704 and 6,903,205); nuc1 promoter (U.S. Pat. No. 6,407,315); Zm40 promoter (U.S. Pat. No. 6,403,862); eep1 and eep2; lec1 (U.S. Pat. No. 7,122,658); thioredoxin H promoter; mlip15 promoter (U.S. Pat. No. 6,479,734); PCNA2 promoter; and the shrunken-2 promoter. (Shaw et al., Plant Phys 98:1214-1216, 1992; Zhong Chen et al., PNAS USA 100:3525-3530, 2003).

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (e.g., PR proteins, SAR proteins, beta-1,3-glucanase, chitinase). See, for example, Redolfi et al. (1983) Neth. J. Plant Pathol. 89:245-254; Uknes et al. (1992) Plant Cell 4:645-656; and Van Loon (1985) Plant Mol. Virol. 4:111-116. See also inducible maize promoters described in U.S. Pat. No. 6,429,362.

In addition to plant promoters, other suitable promoters may be derived from bacterial origin (e.g., the octopine synthase promoter, the nopaline synthase promoter and other promoters derived from Ti plasmids), or may be derived from viral promoters (e.g., 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

The term "enhancer" refers to a nucleic acid molecule, or a nucleic acid sequence, that can recruit transcriptional regulatory proteins such as transcriptional activators, to enhance transcriptional activation by increasing promoter activity. Suitable enhancers can be derived from regions proximate to a native promoter of interest (homologous sources) or can be derived from non-native contexts (heterologous sources) and operably-linked to any promoter of interest within NtHMA RNAi expression vectors to enhance the activity and/or the tissue-specificity of a promoter. Some enhancers can operate in any orientation with respect to the orientation of a transcription unit. For example, enhancers may be positioned upstream or downstream of a transcriptional unit comprising a promoter and a NtHMA RNAi construct. Persons skilled in the art are capable of operably-linking enhancers and promoters to optimize the transcription levels of NtHMA RNAi constructs.

B. RNAi Expression Vectors Comprising NtHMA RNAi Constructs Encoding NtHMA RNAi Polynucleotides RNA Interference ("RNAi") or RNA silencing is an evolutionarily conserved process by which specific mRNAs can be targeted for enzymatic degradation. A double-stranded RNA (dsRNA) must be introduced or produced by a cell (e.g., dsRNA virus, or NtHMA RNAi polynucleotides) to initiate the RNAi pathway. The dsRNA can be converted into multiple siRNA duplexes of 21-23 bp length ("siRNAs") by RNases III, which are dsRNA-specific endonucleases ("Dicer"). The siRNAs can be subsequently recognized by RNA-induced silencing complexes ("RISC") that promote the unwinding of siRNA through an ATP-dependent process. The unwound antisense strand of the siRNA guides the activated RISC to the targeted mRNA (e.g., NtHMA RNA variants) comprising a sequence complementary to the siRNA anti-sense strand. The targeted mRNA and the anti-sense strand can form an A-form helix, and the major groove of the A-form helix can be recognized by the activated RISC. The target mRNA can be cleaved by activated RISC at a single site defined by the binding site of the 5'-end of the siRNA strand. The activated RISC can be recycled to catalyze another cleavage event.

Figure 2A:
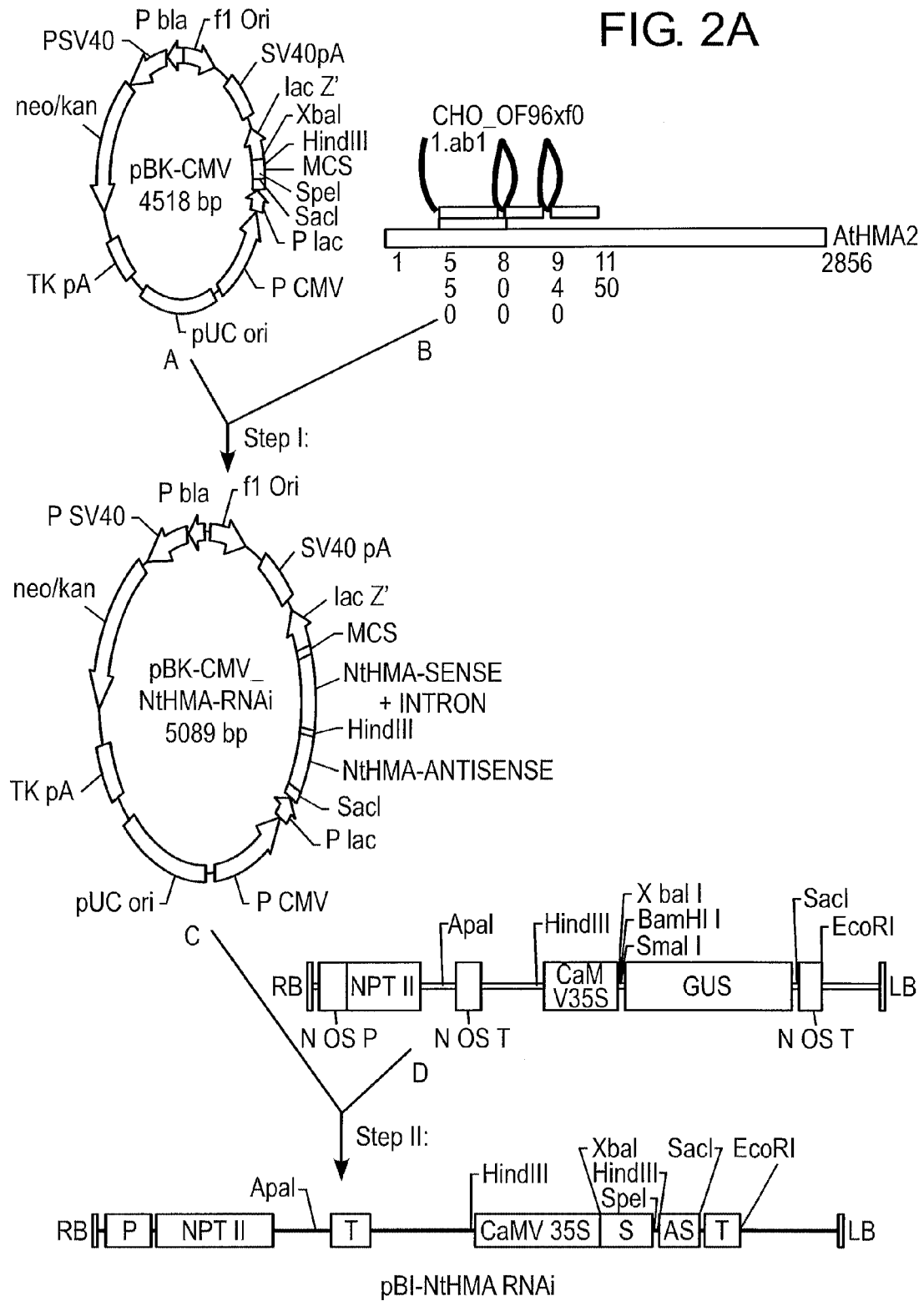
FIG. 2A illustrates an exemplary subcloning strategy for constructing a NtHMA RNAi expression vector that enables the constitutive expression of NtHMA RNAi polynucleotides of interest, as described in Example 2.

FIG. 2A illustrates the construction of an exemplary NtHMA RNAi expression vector. NtHMA RNAi expression vectors comprising NtHMA RNAi constructs encoding NtHMA RNAi polynucleotides exhibit RNA interference activity by reducing the expression level of NtHMA mRNAs, NtHMA pre-mRNAs, and related NtHMA RNA variants. The expression vectors comprise a promoter positioned upstream and operably-linked to a NtHMA RNAi construct, as further defined below. NtHMA RNAi expression vectors comprise a suitable minimal core promoter, a NtHMA RNAi construct of interest, an upstream (5') regulatory region, a downstream (3') regulatory region, including transcription termination and polyadenylation signals, and other sequences known to persons skilled in the art, such as various selection markers.

The NtHMA polynucleotides can be produced in various forms, including as double-stranded hairpin-like structures ("dsRNAi"). The NtHMA dsRNAi can be enzymatically converted to double-stranded NtHMA siRNAs. One of the strands of the NtHMA siRNA duplex can anneal to a complementary sequence within the target NtHMA mRNA and related NtHMA RNA variants. The siRNA/mRNA duplexes are recognized by RISC that can cleave NtHMA RNAs at multiple sites in a sequence-dependent manner, resulting in the degradation of the target NtHMA mRNA and related NtHMA RNA variants.

Figure 2B:
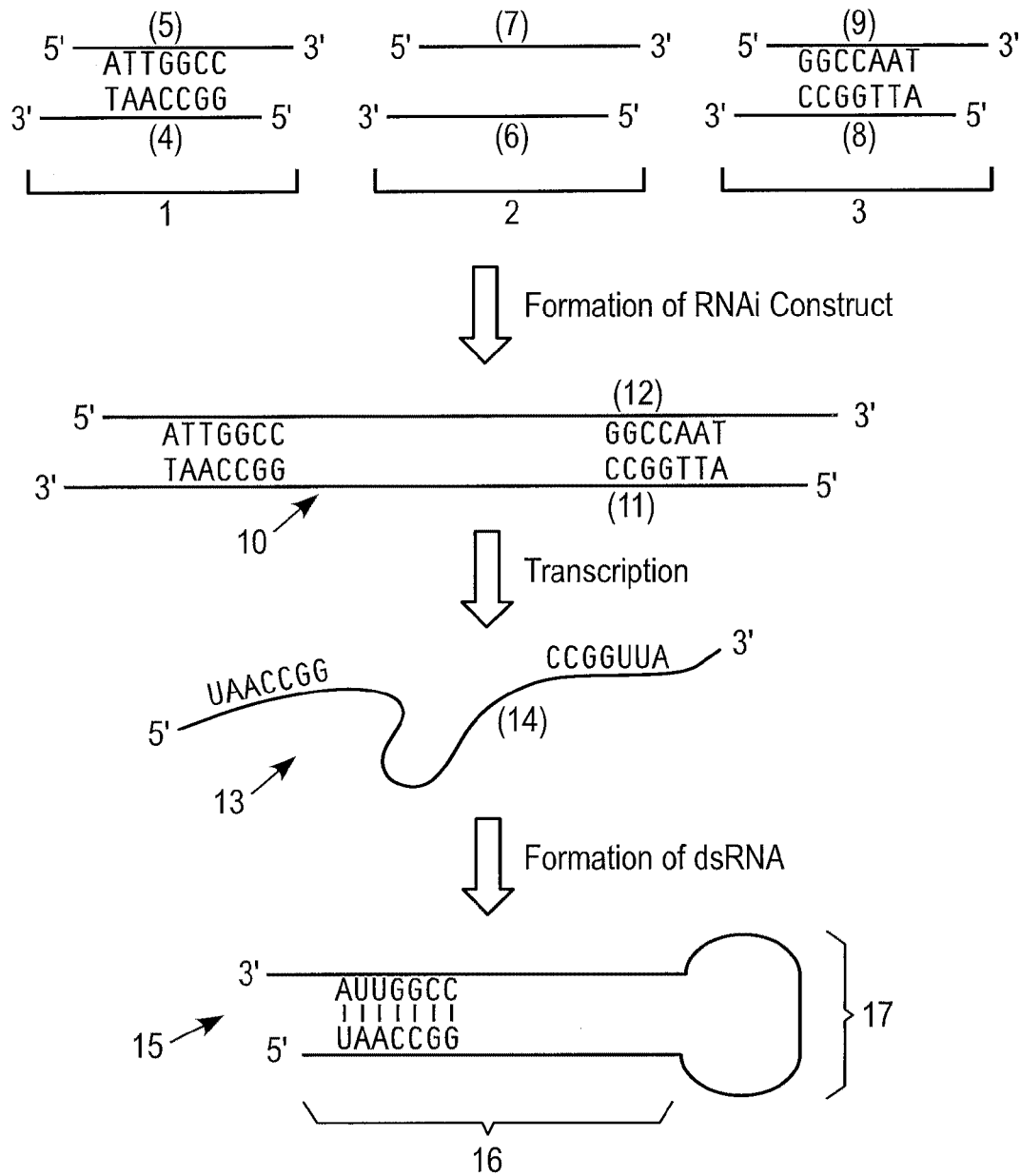
FIG. 2B illustrates a hypothetical double-stranded RNA duplex formed (as "stem-loop-stem" structure) from intramolecular, base-pair interactions within NtHMA RNAi polynucleotide produced as a product transcribed from an exemplary NtHMA RNAi construct.

FIG. 2B illustrates the formation of a hypothetical double-stranded RNA duplex formed (as "stem-loop-stem" structure) as a product transcribed from an exemplary NtHMA RNAi construct. In FIG. 2B, a hypothetical NtHMA RNAi construct 10 is shown, comprising 3 double-stranded DNA fragments, such as fragments 1-3. Fragment 1 is positioned upstream and operably-linked to fragment 2, which is positioned upstream and operably-linked to fragment 3, for which DNA strands/sequences 4, 6, and 8 are liked together in tandem to form strand 11, as shown. Alternatively, a NtHMA RNAi construct comprises "a sense sequence" 5, which is positioned upstream and operably-linked to "a spacer sequence" 7, which is positioned upstream and operably-linked to "a reverse complementary sequence" 9. The strands/sequences 5, 7, and 9 can be liked together in tandem to form strand/sequence 12. Alternatively, a NtHMA RNAi construct comprises "a sense sequence" 8, which is positioned upstream and operably-linked to "a spacer sequence" 6, which is positioned upstream and operably-linked to "a reverse complementary sequence" 4. The strands/sequences 8, 6, and 4 can be liked together in tandem to form strand/sequence 11. Strand 12 is complementary to strand 11. Strand 11 is a template strand that can be transcribed into a NtHMA RNAi polynucleotide 13. The NtHMA RNAi polynucleotide 13 forms a hair-pin ("stem-loop-stem") structure, in which the stem 16 is a complementary region resulting from intramolecular base-pair interactions of the NtHMA RNAi polynucleotide 15 and the loop 17 represents a non-complementary region encoded by a spacer sequence, such as strands/sequences 6 or 7.

Any NtHMA RNA polynucleotide of interest can be produced by selecting a suitable sequence composition, loop size, and stem length for producing the NtHMA hairpin duplex. A suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. A suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions longer than 21 nucleotides may promote effective siRNA-directed silencing, regardless of loop sequence and length.

Exemplary NtHMA RNAi constructs for down-regulating the expression level of the NtHMA gene (SEQ ID NO:1) and other NtHMA-related genes include the following:

Various embodiments are directed to NtHMA RNAi expression vectors comprising a NtHMA RNAi construct that comprises one or more of: intron 1 (SEQ ID NO:4), exon 1 (SEQ ID NO:5), intron 2 (SEQ ID NO:6), exon 2 (SEQ ID NO:7), intron 3 (SEQ ID NO:8), exon 3 (SEQ ID NO:9), intron 4 (SEQ ID NO:10), exon 4 (SEQ ID NO:11), intron 5 (SEQ ID NO:12), exon 5 (SEQ ID NO:13), intron 6 (SEQ ID NO:14), exon 6 (SEQ ID NO:15), intron 7 (SEQ ID NO:16), exon 7 (SEQ ID NO:17), intron 8 (SEQ ID NO:18), exon 8 (SEQ ID NO:19), intron 9 (SEQ ID NO:20), exon 9 (SEQ ID NO:21), intron 10 (SEQ ID NO:22), exon 10 (SEQ ID NO:23), intron 11 (SEQ ID NO:24), exon 11 (SEQ ID NO:25), and intron 12 (SEQ ID NO:26), fragments thereof, and variants thereof.

Various embodiments are directed to NtHMA RNAi expression vectors comprising: a NtHMA RNAi construct having at least 70%, 75%, 80%, 85%, 90%, 95%, 96%, 97%, 98%, and 99% sequence identity to a sequence selected from the group consisting of: exon 1 (SEQ ID NO:5), a fragment of exon 1 (SEQ ID NO:5), exon 2 (SEQ ID NO:7), a fragment of exon 2 (SEQ ID NO:7), exon 3 (SEQ ID NO:9), a fragment of exon 3 (SEQ ID NO:9), exon 4 (SEQ ID NO:11), a fragment of exon 4 (SEQ ID NO:11), exon 5 (SEQ ID NO:13), a fragment of exon 5 (SEQ ID NO:13), exon 6 (SEQ ID NO:15), a fragment of exon 6 (SEQ ID NO:15), exon 7 (SEQ ID NO:17), a fragment of exon 7 (SEQ ID NO:17), exon 8 (SEQ ID NO:19), a fragment of exon 8 (SEQ ID NO:19), exon 9 (SEQ ID NO:21), a fragment of exon 9 (SEQ ID NO:21), exon 10 (SEQ ID NO:23), a fragment of exon 10 (SEQ ID NO:23), exon 11 (SEQ ID NO:25), and a fragment of exon 11 (SEQ ID NO:25).

Various embodiments are directed to NtHMA RNAi expression vectors comprising: a NtHMA RNAi construct encoding NtHMA RNAi polynucleotides capable of self-annealing to form a hairpin structure, in which the RNAi construct comprises (a) a first sequence having at least 70%, 75%, 80%, 85%, 90%, 95%, 96%, 97%, 98%, and 99% sequence identity to SEQ ID NO:3 or SEQ ID NO:47; (b) a second sequence encoding a spacer element of the NtHMA RNAi polynucleotide that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

Various embodiments are directed to NtHMA RNAi expression vectors comprising: a NtHMA RNAi construct encoding NtHMA RNAi polynucleotides capable of self-annealing to form a hairpin structure, in which the RNAi construct comprises (a) a first sequence having at least 70%, 75%, 80%, 85%, 90%, 95%, 96%, 97%, 98%, and 99% sequence identity to SEQ ID NO:3 or SEQ ID NO:47; (b) a second sequence encoding a spacer element of the NtHMA RNAi polynucleotide that forms a loop of the hairpin structure; and (c) a third sequence comprising a reverse complementary sequence of the first sequence (SEQ ID NO:46 or SEQ ID NO:48), positioned in the same orientation as the first sequence, wherein the second sequence is positioned between the first sequence and the third sequence, and the second sequence is operably-linked to the first sequence and to the third sequence.

Various embodiments are directed to NtHMA RNAi expression vectors comprising: a NtHMA RNAi construct that comprises a first sequence having "substantial similarity," or having at least 70%, 75%, 80%, 85%, 90%, 95%, 96%, 97%, 98%, and 99% sequence identity to SEQ ID NO:3, or portions of SEQ ID NO:3. Various embodiments are directed to NtHMA RNAi expression vectors comprising a NtHMA RNAi construct that comprises a first sequence having "substantial similarity," or having at least 70%, 75%, 80%, 85%, 90%, 95%, 96%, 97%, 98%, and 99% sequence identity to SEQ ID NO:47, or portions of SEQ ID NO:47.

Various embodiments are directed to a NtHMA RNAi expression vectors comprising: a NtHMA RNAi construct that comprises a second sequence having "substantial similarity," or having at least 70%, 75%, 80%, 85%, 90%, 95%, 96%, 97%, 98%, and 99% sequence identity to a sequence selected from the group consisting of: intron 1 (SEQ ID NO:4), a fragment of intron 1 (SEQ ID NO:4), intron 2 (SEQ ID NO:6), a fragment of intron 2 (SEQ ID NO:6), intron 3 (SEQ ID NO:8), a fragment of intron 3 (SEQ ID NO:8), intron 4 (SEQ ID NO:10), a fragment of intron 4 (SEQ ID NO:10), intron 5 (SEQ ID NO:12), a fragment of intron 5 (SEQ ID NO:12), intron 6 (SEQ ID NO:14), a fragment of intron 6 (SEQ ID NO:14), intron 7 (SEQ ID NO:16), a fragment of intron 7 (SEQ ID NO:16), intron 8 (SEQ ID NO:18), a fragment of intron 8 (SEQ ID NO:18), intron 9 (SEQ ID NO:20), a fragment of intron 9 (SEQ ID NO:20), intron 10 (SEQ ID NO:22), a fragment of intron 10 (SEQ ID NO:22), intron 11 (SEQ ID NO:24), a fragment of intron 11 (SEQ ID NO:24), intron 12 (SEQ ID NO:26), and a fragment of intron 12 (SEQ ID NO:26). Alternatively, the second sequence of the NtHMA RNAi construct can be randomly generated without utilizing an intron sequence derived from the NtHMA gene (SEQ ID NO:1).

Various embodiments are directed to NtHMA RNAi expression vectors comprising: a NtHMA RNAi construct that comprises a third sequence having "substantial similarity," or having at least 70%, 75%, 80%, 85%, 90%, 95%, 96%, 97%, 98%, and 99% sequence identity to SEQ ID NO:46, or portions of SEQ ID NO:46. Various embodiments are directed to NtHMA RNAi expression vectors comprising a NtHMA RNAi construct that comprises a third sequence having "substantial similarity," or having at least 70%, 75%, 80%, 85%, 90%, 95%, 96%, 97%, 98%, and 99% sequence identity to SEQ ID NO:48, or portions of SEQ ID NO:48.

Various embodiments are directed to NtHMA RNAi expression vectors comprising: a NtHMA RNAi construct that comprises a third sequence having "substantial similarity," or having at least 70%, 75%, 80%, 85%, 90%, 95%, 96%, 97%, 98%, and 99% sequence identity to a reverse complementary sequence selected from the group consisting of: SEQ ID NO:27 (exon 1), a fragment of SEQ ID NO:27 (exon 1), SEQ ID NO:28 (exon 2), a fragment of SEQ ID NO:28 (exon 2), SEQ ID NO:29 (exon 3), a fragment of SEQ ID NO:29 (exon 3), SEQ ID NO:30 (exon 4), a fragment of SEQ ID NO:30 (exon 4), SEQ ID NO:31 (exon 5), a fragment of SEQ ID NO:31 (exon 5), SEQ ID NO:32 (exon 6), a fragment of SEQ ID NO:32 (exon 6), SEQ ID NO:33 (exon 7), a fragment of SEQ ID NO:33 (exon 7), SEQ ID NO:34 (exon 8), a fragment of SEQ ID NO:34 (exon 8), SEQ ID NO:35 (exon 9), a fragment of SEQ ID NO:35 (exon 9), SEQ ID NO:36 (exon 10), a fragment of SEQ ID NO:36 (exon 10), SEQ ID NO:37 (exon 11), and a fragment of SEQ ID NO:37 (exon 11).

Various embodiments are directed to NtHMA RNAi expression vectors comprising a NtHMA RNAi construct that comprises: SEQ ID NO:38 ("sense sequence/fragment"), the second sequence comprises SEQ ID NO:39 ("spacer sequence/fragment") and the third sequence comprises SEQ ID NO:40 ("anti-sense sequence/fragment").

Various embodiments are directed to NtHMA RNAi expression vectors comprising a NtHMA RNAi construct that comprises: SEQ ID NO:42 ("sense sequence/fragment"), the second sequence comprises SEQ ID NO:43 ("spacer sequence/fragment"), and the third sequence comprises SEQ ID NO:44 ("anti-sense sequence/fragment").

Alternatively, the disclosed sequences can be utilized for constructing various NtHMA polynucleotides that do not form hairpin structures. For example, a NtHMA long double-stranded RNA can be formed by (1) transcribing a first strand of the NtHMA cDNA by operably-linking to a first promoter, and (2) transcribing the reverse complementary sequence of the first strand of the NtHMA cDNA fragment by operably-linking to a second promoter. Each strand of the NtHMA polynucleotide can be transcribed from the same expression vector, or from different expression vectors. The NtHMA RNA duplex having RNA interference activity can be enzymatically converted to siRNAs to reduce NtHMA RNA levels.

C. Expression Vectors for Reducing NtHMA Gene Expression by Co-Suppression

Various compositions and methods are provided for reducing the endogenous expression levels for members of the NtHMA gene family by promoting co-suppression of NtHMA gene expression. The phenomenon of co-suppression occurs as a result of introducing multiple copies of a transgene into a plant cell host. Integration of multiple copies of a transgene can result in reduced expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (i.e., the endogenous promoter and endogenous gene of interest) that can preclude transcription. Alternatively, in some cases, co-suppression of the endogenous gene and the transgene can occur by post transcriptional gene silencing ("PTGS"), in which transcripts can be produced but enhanced rates of degradation preclude accumulation of transcripts. The mechanism for co-suppression by PTGS is thought to resemble RNA interference, in that RNA seems to be both an important initiator and a target in these processes, and may be mediated at least in part by the same molecular machinery, possibly through RNA-guided degradation of mRNAs.

Co-suppression of members of the NtHMA gene family can be achieved by integrating multiple copies of the NtHMA cDNA or fragments thereof, as transgenes, into the genome of a plant of interest. The host plant can be transformed with an expression vector comprising a promoter operably-linked to NtHMA cDNA or fragments thereof. Various embodiments are directed to expression vectors for promoting co-suppression of endogenous genes of the NtHMA family comprising: a promoter operably-linked to NtHMA cDNA identified as Clone P6663 (SEQ ID NO:3) or a fragment thereof, or NtHMA cDNA identified as Clone P6643 (SEQ ID NO:47) or a fragment thereof. Various embodiments are directed to expression vectors for promoting co-suppression of endogenous genes of the NtHMA family comprising: a promoter operably-linked to NtHMA cDNA, or a fragment thereof, having at least about 70%, 75%, 80%, 85%, 90%, 95%, 96%, 97%, 98%, or 99% sequence identity to SEQ ID NO:3 or SEQ ID NO:47.

Various embodiments are directed to methods for reducing the expression level of endogenous genes of the NtHMA family by integrating multiple copies of NtHMA cDNA or a fragment thereof into a plant genome, comprising: transforming a plant cell host with an expression vector that comprises a promoter operably-linked to SEQ ID NO:3, or a fragment thereof; or SEQ ID NO:47, or a fragment thereof. Various embodiments are directed to methods for reducing the expression level of endogenous genes of the NtHMA family by integrating multiple copies of NtHMA cDNA, or a fragment thereof, into a plant genome, comprising: transforming a plant cell host with an expression vector that comprises a promoter operably-linked to NtHMA cDNA, or a fragment thereof, having at least about 70%, 75%, 80%, 85%, 90%, 95%, 96%, 97%, 98%, or 99% sequence identity to SEQ ID NO:3 or SEQ ID NO:47.

D. Expression Vectors for Reducing NtHMA Gene Expression by Inhibition of Translation by Anti-Sense Agents Various compositions and methods are provided for reducing the endogenous expression level of the NtHMA gene family by inhibiting the translation of NtHMA mRNA. A host plant cell can be transformed with an expression vector comprising: a promoter operably-linked to NtHMA cDNA or a fragment thereof, positioned in anti-sense orientation with respect to the promoter to enable the expression of RNA polynucleotides having a sequence complementary to a portion of NtHMA mRNA. Various expression vectors for inhibiting the translation of HMA mRNA comprise: a promoter operably-linked to NtHMA cDNA identified as Clone P6663 (SEQ ID NO:3) or a fragment thereof; or NtHMA cDNA identified as Clone P6643 (SEQ ID NO:47) or a fragment thereof, in which the NtHMA cDNA, or the fragment thereof, is positioned in anti-sense orientation with respect to the promoter. Various expression vectors for inhibiting the translation of HMA mRNA comprise: a promoter operably-linked to a NtHMA cDNA, or a fragment thereof, having at least about 70%, 75%, 80%, 85%, 90%, 95%, 96%, 97%, 98%, or 99% sequence identity to SEQ ID NO:3 or SEQ ID NO:47, in which the NtHMA cDNA, or the fragment thereof, is positioned in anti-sense orientation with respect to the promoter. The lengths of anti-sense NtHMA RNA polynucleotides can vary, including 15-20 nucleotides, 20-30 nucleotides, 30-50 nucleotides, 50-75 nucleotides, 75-100 nucleotides, 100-150 nucleotides, 150-200 nucleotides, and 200-300 nucleotides.

Various embodiments are directed to methods for reducing the expression level of endogenous genes of the NtHMA family by inhibiting NtHMA mRNA translation, comprising: transforming a plant cell host with an expression vector that comprises a promoter operably-linked to NtHMA cDNA identified as Clone P6663 (SEQ ID NO:3) or a fragment thereof; or NtHMA cDNA identified as Clone P6643 (SEQ ID NO:47) or a fragment thereof, in which the NtHMA cDNA, or the fragment thereof, is positioned in anti-sense orientation with respect to the promoter. Various embodiments are directed to methods for reducing the expression level of endogenous genes of the NtHMA family by inhibiting NtHMA mRNA translation, comprising: transforming a plant cell host with an expression vector that comprises a promoter operably-linked to a NtHMA cDNA, or a fragment thereof, having at least about 70%, 75%, 80%, 85%, 90%, 95%, 96%, 97%, 98%, or 99% sequence identity to SEQ ID NO:3 or SEQ ID NO:47, in which the NtHMA cDNA, or the fragment thereof, is positioned in anti-sense orientation with respect to the promoter.

E. Other Compositions and Methods for Reducing NtHMA Gene Expression

Methods for obtaining conservative variants and more divergent variants of NtHMA polynucleotides and polypeptides are known to persons skilled in the art. Any plant of interest can be genetically modified by various methods known to induce mutagenesis, including site-directed mutagenesis, oligonucleotide-directed mutagenesis, chemically-induced mutagenesis, irradiation-induced mutagenesis, and other equivalent methods. For example, site-directed mutagenesis is described in, e.g., Smith (1985) "In vitro mutagenesis," Ann. Rev. Genet. 19:423-462, and references therein, such as Botstein & Shortle (1985) "Strategies and Applications of in vitro Mutagenesis," Science 229:1193-1201; and in Carter (1986) "Site-directed mutagenesis," Biochem. J. 237:1-7. Oligonucleotide-directed mutagenesis is described in, e.g., Zoller & Smith (1982) "Oligonucleotide-directed Mutagenesis using M13-derived Vectors: an Efficient and General Procedure for the Production of Point mutations in any DNA Fragment," Nucleic Acids Res. 10:6487-6500. Mutagenesis utilizing modified bases is described in, e.g., Kunkel (1985) "Rapid and Efficient Site-specific Mutagenesis without Phenotypic Selection," Proc. Natl. Acad. Sci. USA 82:488-492, and in Taylor et al. (1985) "The Rapid Generation of Oligonucleotide-directed Mutations at High Frequency using Phosphorothioate-modified DNA," Nucl. Acids Res. 13: 8765-8787. Mutagenesis utilizing gapped duplex DNA is described in, e.g., Kramer et al. (1984) "The Gapped Duplex DNA Approach to Oligonucleotide-directed Mutation Construction," Nucl. Acids Res. 12: 9441-9460). Point-mismatch mutagenesis is described in, e.g., Kramer et al. (1984) "Point Mismatch Repair," Cell 38:879-887). Double-strand break mutagenesis is described in, e.g., Mandecki (1986) "Oligonucleotide-directed Double-strand Break Repair in Plasmids of *Escherichia coli*: A Method for Site-specific Mutagenesis," Proc. Natl. Acad. Sci. USA, 83:7177-7181, and in Arnold (1993) "Protein Engineering for Unusual Environments," Current Opinion in Biotechnology 4:450-455). Mutagenesis utilizing repair-deficient host strains is described in, e.g., Carter et al. (1985) "Improved Oligonucleotide Site-directed Mutagenesis using M13 Vectors," Nucl. Acids Res. 13: 4431-4443. Mutagenesis by total gene synthesis is described in, e.g., Nambiar et al. (1984) "Total Synthesis and Cloning of a Gene Coding for the Ribonuclease S Protein," Science 223: 1299-1301. DNA shuffling is described in, e.g., Stemmer (1994) "Rapid Evolution of a Protein in vitro by DNA Shuffling," Nature 370: 389-391, and in Stemmer (1994) "DNA shuffling by random fragmentation and reassembly: In Vitro Recombination for Molecular Evolution," Proc. Natl. Acad. Sci. USA 91:10747-10751.

Alternatively, NtHMA genes can be targeted for inactivation by introducing transposons (and IS elements) into the genomes of plants of interest. These mobile genetic elements can be introduced by sexual cross-fertilization and insertion mutants can be screened for loss in NtHMA activity, such as reduced Cd transport. The disrupted NtHMA gene in a parent plant can be introduced into other plants by crossing the parent plant with plant not subjected to transposon-induced mutagenesis by, e.g., sexual cross-fertilization. Any standard breeding techniques known to persons skilled in the art can be utilized. In one embodiment, one or more NtHMA-related genes can be inactivated by the insertion of one or more transposons. Mutations can result in homozygous disruption of one or more NtHMA genes, in heterozygous disruption of one or more NtHMA genes, or a combination of both homozygous and heterozygous disruptions if more than one NtHMA gene is disrupted. Suitable transposable elements can be selected from two broad classes, designated as Class I and Class II. Suitable Class I transposable elements include retrotransposons, retroposons, and SINE-like elements. Such methods are known to persons skilled in the art as described in Kumar and Bennetzen (1999), Plant Retrotransposons in Annual Review of Genetics 33:479.

Alternatively, NtHMA genes can be targeted for inactivation by a method referred to as Targeting Induced Local Lesions IN Genomics ("TILLING"), which combines high-density point mutations with rapid sensitive detection of mutations. Typically, plant seeds are exposed to mutagens, such as ethylmethanesulfonate (EMS) or EMS alkylates guanine, which typically leads to mispairing. Suitable agents and methods are known to persons skilled in the art as described in McCallum et al., (2000), "Targeting Induced Local Lesions IN Genomics (TILLING) for Plant Functional Genomics," Plant Physiology 123:439-442; McCallum et al., (2000) "Targeted screening for induced mutations," Nature Biotechnology 18:455-457; and Colbert et al., (2001) "High-Throughput Screening for Induced Point Mutations," Plant Physiology 126:480-484.

Alternatively, NtHMA genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, solanum nodiflorum mottle virus, and subterranean clover mottle virus. Various target RNA-specific ribozymes are known to persons skilled in the art as described in Haseloff et al. (1988) Nature, 334:585-591.

III. Transgenic Plants, Cell Lines, and Seeds Comprising NtHMA RNAi Polynucleotides and Related Methods Various embodiments are directed to transgenic plants genetically modified to reduce the NtHMA gene expression level by various methods that can utilized for silencing NtHMA gene expression, and thereby, producing transgenic plants in which the expression level of NtHMA transporters can be reduced within plant tissues of interest. Rates of heavy metal transport and distribution patterns of heavy metal transport, in particular, cadmium transport, can be altered in transgenic plants produced according to the disclosed methods and compositions. Plants suitable for genetic modification include monocots and dicots.

Various embodiments are directed to transgenic tobacco plants genetically modified to reduce the NtHMA gene expression level by various methods that can be utilized for down-regulating NtHMA gene expression, and thereby, producing transgenic tobacco plants in which the expression level of NtHMA transporters can be reduced within plant tissues of interest. Various expression vectors have been provided to produce transgenic lines of tobacco of any variety exhibiting reduced levels of NtHMA gene expression. The disclosed compositions and methods can be applied to any plant species of interest, including plants of the genus *Nicotiana*, various species of *Nicotiana*, including *N. rustica* and *N. tabacum* (e.g., LA B21, LN KY171, TI 1406, Basma, Galpao, Perique, Beinhart 1000-1, and Petico). Other species include *N. acaulis, N. acuminata, N. acuminata* var. *multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorfii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. Suitable plants for transformation include any plant tissue capable of transformation by various methods of transforming plants known by persons skilled in the art, including electroporation, micro-projectile bombardment, and *Agrobacterium*-mediated transfer as described, for example, in U.S. Pat. No. 4,459,355 that discloses a method for transforming susceptible plants, including dicots, with an *Agrobacterium* strain containing a Ti plasmid; U.S. Pat. No. 4,795,855 that discloses transformation of woody plants with an *Agrobacterium* vector; U.S. Pat. No. 4,940,838 that discloses a binary *Agrobacterium* vector; U.S. Pat. No. 4,945,050; and U.S. Pat. No. 5,015,580.

Various embodiments are directed to transgenic tobacco plants genetically modified to exogenously express a RNAi construct encoding NtHMA RNAi polynucleotides that facilitate the degradation of NtHMA RNA transcripts, and consequently, that reduce the number of RNA transcripts available for translation into NtHMA transporters. Various embodiments are directed to transgenic plants comprising an expression vector that enable the expression of NtHMA polynucleotides produced according to the disclosed methods. Various embodiments are directed to cell lines derived from transgenic plants produced according to the disclosed methods. Various embodiments are directed to transgenic seeds derived from transgenic plants produced according to the disclosed methods.

Various embodiments are directed to methods for reducing the NtHMA gene expression levels in plants, the method comprising reducing the expression level of a NtHMA gene, which can be accomplished by various methods known to persons skilled in the art. As examples, this includes: (1) RNA interference method for reducing steady-state level of endogenous NtHMA RNA variants available for translation by expression of NtHMA RNAi polynucleotides; (2) co-suppression method for reducing transcription of NtHMA gene(s) by integrating multiple copies of the NtHMA cDNA or fragments thereof, as transgenes, into a plant genome; (3) anti-sense method for reducing the NtHMA translation by the expression of anti-sense polynucleotides that can target NtHMA RNA; and (4) various methods for inducing mutagenesis.

Various embodiments are directed to transgenic tobacco plants genetically modified to reduce the NtHMA gene expression level by various methods, known to persons skilled in the art, and further modified either to reduce the expression of a second endogenous gene of interest (i.e., not NtHMA-related) or to enhance the expression of an exogenous gene of interest (i.e., not NtHMA-related). For example, the down-regulation of a second endogenous gene of interest encoding an enzyme involved in the biosynthesis of alkyloids may be desirable. In other situations, the enhancement in the expression level of a transgene encoding a recombinant protein of interest, such as a human hormone for therapeutic use, may be desirable. Persons skilled in the art are capable of producing various transgenic plants that can be modified, for example, to exogenously express NtHMA RNAi polynucleotides and at least one recombinant gene product of interest, such as a recombinant human growth factor or RNAi polynucleotides that can target a second gene of interest not related to the NtHMA family.

Producing transgenic plants according to the disclosed methods provides a number of advantages. Transgenic plants, including transgenic tobacco plants, can be grown in soils containing variable Cd concentrations, or in soils containing less than desirable Cd concentrations. These transgenic plants and derivative seeds can provide more options for cultivating them in a broader range of soil environments, which may increase the amount of cultivatable soils available to practitioners (e.g., farmers). Furthermore, these transgenic plants, exhibiting reduced Cd content, compared to non-transgenic counterparts can be consumed directly as edible products. The consumption of edible portions of these transgenic plants can be a healthier option compared to the consumption of non-transgenic counterparts. Suitable plants that can be genetically modified according to the disclosed methods, include plants cultivatable for agricultural use, including rice, corn, squash, soybeans, lettuce, potatoes, beats, herbs, wheat, barley, carrots, etc. The % Cd reduction in these transgenic plants, including the leaf lamina portion, can be approximately at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, and 99%, when compared to non-transgenic counterparts. The Cd content of these transgenic plants, including the leaf lamina portion, is a value from a range from about 0.01 to about 0.05 ppm, from about 0.01 to about 0.1 ppm, from about 0.01 to about 0.5 ppm, from about 0.01 to about 1.0 ppm, and from about 0.01 to about 5 ppm.

IV. Consumable Products Incorporating Tobacco Leaves Genetically Modified to Contain Reduced Cd Content Various embodiments provide transgenic plants, in which the expression level of members of the NtHMA gene family is substantially reduced to curtail or impede Cd transport into the leaf lamina. The leaf lamina derived from transgenic tobacco plants, produced according to the disclosed methods, can be incorporated into various consumable products containing Cd at a level substantially below that of consumable products made by incorporating tobacco leaves derived from plants of the same genotype that were grown under identical conditions, but not genetically modified with respect to the reduced expression level of members of the NtHMA gene family ("non-transgenic counterparts").

In some embodiments, these transgenic plants exhibiting reduced Cd content compared to non-transgenic counterparts can be incorporated into consumable products, including various smokable articles, such as cigars, cigarettes, and smokeless tobacco products (i.e., non-combustible). Smokable articles and smokeless tobacco products, produced by incorporating tobacco leaves derived from tobacco plants genetically modified to contain reduced Cd levels according to the disclosed methods, can provide healthier options compared to non-transgenic counterparts.

Smokeless tobacco products incorporating tobacco plants genetically modified according to the disclosed methods can be manufactured in any format suitable for comfort in a consumer's oral cavity. Smokeless tobacco products contain tobacco in any form, including as dried particles, shreds, granules, powders, or a slurry (i.e., tobacco extract), deposited on, mixed in, surrounded by, or otherwise combined with other ingredients in any format, such as flakes, films, tabs, foams, or beads. Smokeless tobacco products may be wrapped with a material, which may be edible (i.e., orally disintegrable) or nonedible. Liquid contents of smokeless tobacco products can be enclosed in a form, such as beads, to preclude interaction with a water-soluble wrapper. The wrapper may be shaped as a pouch to partially or completely enclose tobacco-incorporating compositions, or to function as an adhesive to hold together a plurality of tabs, beads, or flakes of tobacco. A wrapper may also enclose a moldable tobacco composition that conforms to the shape of a consumer's mouth. An orally disintegrable wrapper may enclose smokeless tobacco, e.g., as dry snuff or soluble tobacco, and may be formed on continuous thermoforming or horizontal form/fill/seal equipment or other suitable packaging equipment using edible films (which may or may not contain tobacco). Exemplary materials for constructing a wrapper include film compositions comprising HPMC, CMC, pectin, alginates, pullulan, and other commercially viable, edible film-forming polymers. Other wrapping materials may include pre-formed capsules produced from gelatin, HPMC, starch/carrageenan, or other commercially available materials. Such wrapping materials may include tobacco as an ingredient. Wrappers that are not orally disintegrable may be composed of woven or nonwoven fabrics, of coated or uncoated paper, or of perforated or otherwise porous plastic films. Wrappers may incorporate flavoring and/or coloring agents. Smokeless products can be assembled together with a wrapper utilizing any method known to persons skilled in the art of commercial packaging, including methods such as blister packing and stik-paking, in which a small package can be formed by a vertical form/fill/seal packaging machine.

The % Cd reduction in these smokable articles and smokeless products, produced by incorporating tobacco leaves derived from tobacco plants genetically modified to contain reduced Cd levels, is a value of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100%, when compared to consumable products derived from non-transgenic counterparts. In some embodiments, the Cd content of these smokable articles and smokeless products, produced by incorporating tobacco leaves derived from tobacco plants genetically modified to contain reduced Cd levels, is a value from a range from about 0.01 to about 0.05 ppm, from about 0.01 to about 0.1 ppm, from about 0.01 to about 0.5 ppm, from about 0.01 to about 1.0 ppm, and from about 0.01 to about 5 ppm.

The degree of Cd accumulation in plants can be substantially variable depending on several parameters attributed to the complexity of the genotype and the growth environment. For example, Cd concentrations in field-grown tobacco leaves can be extremely variable depending on factors such as the agro-climate, soil parameters, and cultivars. Furthermore, the relative Cd distribution patterns within different portions of a tobacco plant can vary according to the species, the organ/tissue, and growth conditions (i.e., field-grown vs. hydroponically-grown). On average, the Cd concentrations measured in field-grown tobacco leaves (including midribs and veins) can be in the range from approximately 0.5 to 5 ppm (parts per million, or ug/g of dry weight of tobacco leaves). However, many published Cd levels typically do not define the tobacco maturity stage, the tobacco variety, or the particular leaf portions (i.e., removal from leaf stalk position) harvested for analysis. In some varieties, the lower leaves may accumulate higher Cd levels than the medium and upper leaves. At the intracellular level, Cd can be found in various cell components of a plant cell, including the cell wall, cytoplasm, chloroplast, nucleus, and vacuoles.

Furthermore, Cd content measured in tobacco leaves can vary substantially depending on the Cd levels in the soil environment where the tobacco plants were grown. The leaves of tobacco grown in Cd-contaminated areas can accumulate Cd from about 35 ppm or higher, compared to the leaves of genetically identical counterparts grown in non-contaminated areas, which can accumulate Cd at a range from approximately 0.4 to approximately 8 ppm. The vacuoles within the leaves of plants grown in Cd-contaminated areas can accumulate very high Cd concentrations. Methods for applying the disclosed compositions to be suitable for a given plant species of interest are known to persons skilled in the art.

EXAMPLES

Example 1

Cloning and Exon Mapping of a Full-Length *Nicotiana* NtHMA Genomic Clone

Two partial genomic clones representing different portions of an endogenous NtHMA gene were independently identified, referred to as "CHO_OF96xf01.ab1" and "CHO_OF261xo09c1.ab1." Based on sequence information obtained from the partial genomic clones, a full-length genomic clone (_HO-18-2) and 4 full-length NtHMA cDNAs were subsequently identified, including clone P6663 (SEQ ID NO:3) and clone P6643 (SEQ ID NO:47). The exon and intron subregions of full-length genomic clone (_HO-18-2) (17,921 bp) were mapped. As shown in FIG. 1A, the full-length, endogenous NtHMA gene cloned from *Nicotiana* comprises 11 exons consisting of 3392 nucleotides in total.

Example 2

Construction of NtHMA RNAi Expression Vector PBI121-NtHMA (660-915) Encoding RNAi Polynucleotides FIG. 1B provides a list of nucleotide positions mapped to each exon within the isolated NtHMA genomic clone (SEQ ID NO: 1) ("Table 1"). The partial genomic clone CHO_OF96xf01.ab1 includes a part of intron 4, exon 4, intron 5, exon 5, intron 6, and a part of exon 6, as shown in FIG. 1A, and listed under Table 1 of FIG. 1B. The partial genomic clone CHO_OF261xo09c1 includes a part of intron 7, exon 7, intron 8, exon 8, and a part of exon 9, as shown in FIG. 1A. To produce transgenic plants that can stably produce recombinant NtHMA RNAi polynucleotides of interest that can facilitate the degradation of endogenous RNA transcripts encoding NtHMA polypeptides, two sets of NtHMA RNAi expression vectors, the PBI121-NtHMA (660-915) RNAi expression vector as further described below, and the PBI121-NtHMA (1382-1584) RNAi expression vector as further described in Example 3.

FIG. 2 illustrates an exemplary subcloning strategy for constructing a NtHMA RNAi expression vector that enables the constitutive expression of NtHMA RNAi polynucleotides of interest. Based on exon mapping and sequence analysis of genomic clone CHO_OF96xf01.ab1, RNAi constructs were designed.

FIG. 3A shows an exemplary RNAi sequence, NtHMA (660-915), for producing NtHMA RNAi polynucleotides of interest. In FIG. 3A, NtHMA RNAi RNAi construct comprises a sense fragment (272 bp) (SEQ ID NO:38) composed of exon 4 (272 bp), which is positioned upstream and operably-linked to a spacer fragment (80 bp) (SEQ ID NO:39) composed of intron 5, which is positioned upstream and operably-linked to a reverse complementary fragment (272 bp) (SEQ ID NO:40) composed of exon 4 positioned in anti-sense orientation. RNAi constructs encoding NtHMA RNAi polynucleotides of interest were inserted into the PBKCMV cloning vector, and were placed downstream and operably-linked to a cytomegalovirus (CMV) promoter. XbaI and HindIII sites were incorporated into the 5' and 3' ends of the 352 bp NtHMA sense fragment, which included the 80 bp intron fragment by utilizing PCR primers modified to incorporate these restriction enzyme sites (PMG783F: ATTCTAGACTGCTGCTATGTCATCACTGG (SEQ ID NO:54) and PMG783R: ATAAGCTTAGCCTGAAGAATTGAGCAAA (SEQ ID NO:55)). Similarly, SpeI and SacI sites were incorporated into the 5' and 3' ends of the corresponding NtHMA reverse complementary fragment by utilizing PCR primers (PMG 785F: ATGAGCTCTGGTTATGTAGGCTACTGCTGCT (SEQ ID NO:56) and PMG 786R: ATACTAGTATTTGTAGTGCCAGCCCAGA (SEQ ID NO:57)) to produce the PBKCMV-NtHMA RNAi plasmid. The PBI121-NtHMA RNAi expression vectors were constructed by (a) excising the β-glucuronidase ORF from the binary expression vector ("pBI121" from CLONTECH), and (b) substituting the NtHMA RNAi construct, excised from the PBKCMV-NtHMA RNAi plasmid, into XbaI/SacI sites of the PBI121 plasmid in place of the removed β-glucuronidase ORF. The PBI121-NtHMA RNAi expression vectors comprise: (i) 352 bp XbaI-HindIII NtHMA sense fragment that includes (ii) 80 bp intron fragment, operably-linked to the (iii) 272 bp SpeII-SacI NtHMA reverse complementary fragment.

Example 3

Construction of NtHMA RNAi Expression Vector PBI121-NtHMA (1382-1584) Encoding RNAi Polynucleotides FIG. 4A shows an exemplary RNAi sequence, NtHMA (1382-1584), for producing NtHMA RNAi polynucleotides of interest. Based on exon mapping and sequence analysis of genomic clone CHO_OF261xo09c1, a RNAi construct was designed that includes a sense fragment (191 bp) (SEQ ID NO:42) comprising sequences of exon 7, which is positioned upstream and operably-linked to a spacer DNA fragment (139 bp) (SEQ ID NO:43) comprising sequences of intron 8, which is positioned upstream and operably-linked to a reverse complementary fragment (196 bp) (SEQ ID NO:44) comprising sequences of exon 7 positioned in anti-sense orientation. These RNAi constructs encoding NtHMA RNAi polynucleotides of interest were inserted into the PBKCMV cloning vector, and were placed downstream and operably-linked to a cytomegalovirus (CMV) promoter. XbaI and HindIII sites were incorporated into the 5' and 3' ends of the 330 bp NtHMA sense fragment, which included the 139 bp intron fragment by utilizing PCR primers modified to incorporate these restriction enzyme sites (PMG754F: ATTCTAGATGAGAGCAAGTCAGGTCATCC (SEQ ID NO:58) and PMG754R: ATAAGCTTTTCAAACATCCACCGCATTA (SEQ ID NO:59)). Similarly, PstI and SacI sites were incorporated into the 5' and 3' ends of the corresponding NtHMA reverse complementary fragment by utilizing PCR primers PMG757F: ATGAGCTCGCATTGAGAGCAAGTCAGGTC (SEQ ID NO:60) and PMG757R: ATCTGCAGCCTGTGGTACATCCAGCTCTT (SEQ ID NO:61)) to produce the PBKCMV-NtHMA RNAi expression vector.

The PBI121-NtHMA RNAi expression vectors were constructed by (a) excising the β-glucuronidase ORF from the binary expression vector ("pBI121" from CLONTECH), and (b) substituting the NtHMA RNAi construct, excised from the PBKCMV-NtHMA RNAi plasmid, into XbaI/SacI sites of the PBI121 plasmid in place of the removed β-glucuronidase ORF. The PBI121-NtHMA RNAi expression vectors comprise: (i) 330 bp XbaI-HindIII NtHMA sense fragment that includes (ii) 139 bp intron fragment, operably-linked to the (iii) 196 bp SpeII-SacI NtHMA reverse complementary fragment. The PBI121-NtHMA RNAi expression vectors, such as those described in Examples 2 and 3, can be introduced into any host plant cell of interest by various methods known to persons skilled in the art.

Example 4

Transformation of Burley (TN90), Flue-Cured (K326), and Dark (VA359) Tobacco Varieties with NtHMA RNAi Expression Vectors Tobacco seeds from three different varieties, Burley (TN90), Flue-cured (K326), and Dark (VA359), were sterilized and germinated in a petridish containing MS basal media supplemented with 5 ml/L plant preservative mixture (PPM). Seedlings, at approximately 7 to 10 days post-germination, were selected for transformation with various NtHMA RNAi expression vectors. A single colony of *Agrobacterium tumefaciens* LBA4404 was inoculated into a liquid LB medium containing 50 mg $l^{-1}$ kanamycin (kanamycin mono sulphate), and were incubated for 48 h at 28° C. with reciprocal shaking (150 cycles $min^{-1}$). Cultured bacterial cells were collected by centrifugation (6000×g, 10 min), and were suspended to a final density of 0.4-0.7 $OD_{600}$, with 20 ml liquid MS medium containing 20 $g^{-1}$ sucrose. The 7-10 day seedling explants were immersed into a bacterial suspension for 5 mins, and were blotted on sterile filter papers. Fifty explants were placed onto 40 ml aliquots of REG agar medium (MS basal medium supplemented with 0.1 mg $l^{-1}$ NAA and 1 mg $l^{-1}$ BAP) in 100 mm×20 mm petri dishes. The explants were co-cultivated with *Agrobacterium* at 25° C. After 3 days of co-cultivation, the explants were washed and transferred to RCPK medium (REG medium with 100 $mg^{-1}$ kanamycin, 500 mg $l^{-1}$ carbenicillin, and 5 ml PPM) to select for transformants. The explants were subcultured every 2 weeks. After 8-12 weeks of growth under selective conditions, the surviving plants, representing transformants that have integrated the NtHMA RNAi expression constructs into their genomes, were transferred to a rooting medium (MS basal medium supplemented with 100 mg $l^{-1}$-Kanamycin). Rooted plants were transferred to pots to promote further growth.

Example 5

Cd Reduction in Leaf Lamina of First Generation Transgenics Genetically Modified to Express NtHMA RNAi Polynucleotides To determine the effect of NtHMA RNAi polynucleotide expression on Cd transport from the root to aerial portions of transgenic plants, the Cd levels were determined for several transgenic lines that have been genetically modified to express either the NtHMA (660-915) or the (1382-1584) RNAi polynucleotides.

Approximately 40 independent transgenic plants, representing three tobacco varieties, were transformed with various PBI121-NtHMA RNAi expression vectors. Initially, transformants were grown in floating trays containing Hoaglands medium for 4 weeks. PCR positive plants for NPT II were selected and potted in 10" pots with a hydroponic system containing Hoaglands medium containing 5 μM $CdCl_2$. After 4-8 weeks, two middle leaves samples were harvested and freeze-dried for metal analysis, or were frozen in liquid nitrogen for gene expression analysis. Approximately 500 mg of tobacco was weighed and digested in 10 ml of concentrated $HNO_3$ by microwave-accelerated, reaction system 5 digestion system (CEM corporation, Mathews, N.C.). Heavy metal concentrations were analyzed utilizing inductively coupled plasma-mass spectrophotometry ("ICP-MS," Agilent 7500A; Agilent Technologies, Palo Alto, Calif.). As non-transgenic tobacco control, a sample consisting of polish-certified, Virginia tobacco leaves, CTA-VTL-2, was prepared under comparable conditions (Dybczynski et al., 1997).

FIGS. 3B-3D show Cd reduction in leaf lamina of multiple first generation (T0) transgenic lines, representing three varieties, that have been genetically modified to express NtHMA RNAi polynucleotides (660-915).

FIGS. 4B-4D show Cd reduction in leaf lamina of multiple first generation (T0) transgenic lines, representing three varieties, that have been genetically modified to express NtHMA RNAi polynucleotides (1382-1584).

Example 6

Reduction in NtHMA RNA Transcripts in Transgenic Tobacco Leaf by the Expression of NtHMA RNAi Polynucleotides To determine the effect of NtHMA RNAi polynucleotide expression on the steady-state levels of endogenous NtHMA RNA transcripts, the relative change in NtHMA RNA transcripts was measured by isolating total cellular RNA from leaf lamina portions of various transgenic lines, representing three tobacco varieties.

Total RNA was isolated from middle leaves of T0 plants using TRI® Reagent (Sigma-Aldrich, St. Louis, Mo.). To remove DNA impurities, purified RNA was treated with RNase-free DNase (TURBO DNA-free, Ambion, Austin Tex.). To synthesize the first cDNA strand, approximately 10 μg of total RNA was reverse transcribed utilizing the High Capacity cDNA Archive Kit (Applied Biosystems, Foster City, Calif.). To measure the level of NtHMA transcripts in the samples, a quantitative 2-step RT-PCR was performed according to the Taqman MGB probe-based chemistry. The RT mixture contained 4 μM dNTP mix, 1× random primers, 1×RT Buffer, 10 g cDNA, 50U Multiscribe Reverse transcriptase (Applied Biosystems), 2U Superase-In RNase Inhibitor (Ambion), and nuclease-free water. The PCR mixture contained 1× Taqman Universal PCR Master Mix (Applied Biosystems, Foster City, Calif.), 400 nM forward primer, 400 nM reverse primer, 250 nM Taqman MGB probe, 2 ng of cDNA, and nuclease-free water. RT-PCR was performed utilizing an ABI 7500 Real-Time System (Applied Biosystems, Foster City, Calif.) and under amplification conditions: 50° C. for 2 min.; 95° C. for 10 min.; 40 cycles of 95° C. for 15 sec.; and 60° C. for 1 min. For normalizing the measured NtHMA RNA transcript levels, the Glyceraldehyde-3-Phosphate Dehydrogenase (G3PDH) was selected as a control endogenous RNA transcript, whose expression level is not responsive to the sequence-specific RNA interference activity of the NtHMA RNAi polynucleotides under analysis. The fold change in NtHMA RNA transcript level caused by NtHMA-RNAi-polynucleotide expression was calculated by determining the ratio of (a)/(b), in which (a) represents the normalized value of NtHMA RNA transcript level determined for samples derived from transgenic plants transformed with a NtHMA RNAi expression vector, and (b) represents the normalized value of NtHMA RNA transcript level determined for samples derived from transgenic plants transformed with a control expression vector deficient in the NtHMA RNAi RNAi construct.

Figure 5A:
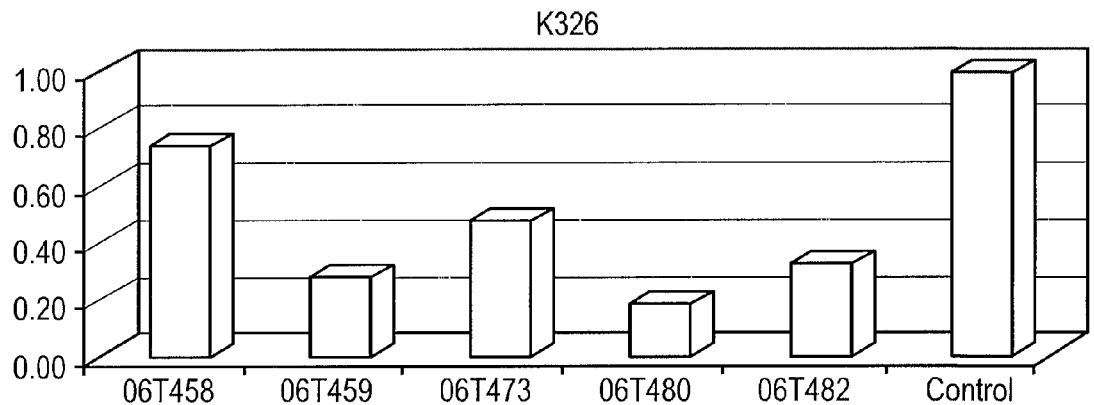
FIGS. 5A-C show normalized NtHMA RNA transcript levels in various first generation (T0) transgenic lines that have been genetically modified to express NtHMA RNAi polynucleotides of interest, as determined by quantitative realtime PCR analysis of leaf lamina extracts, as described in Example 6.
Figure 5B:
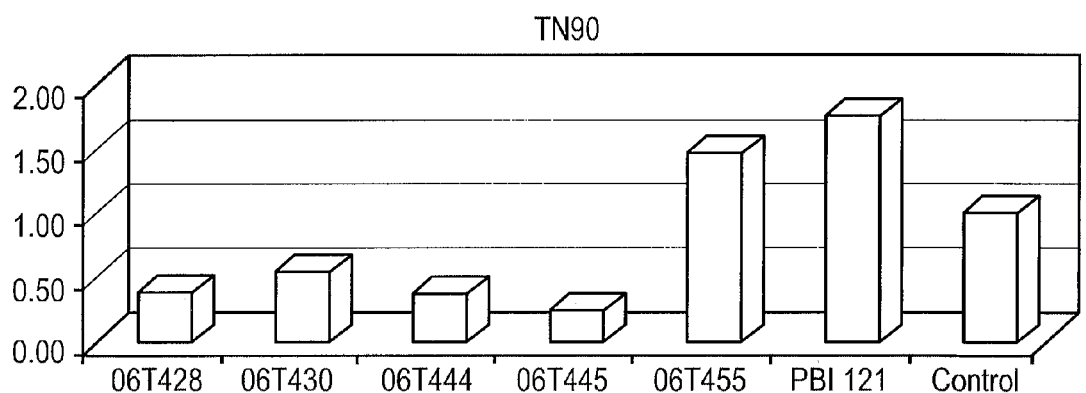
Figure 5C:
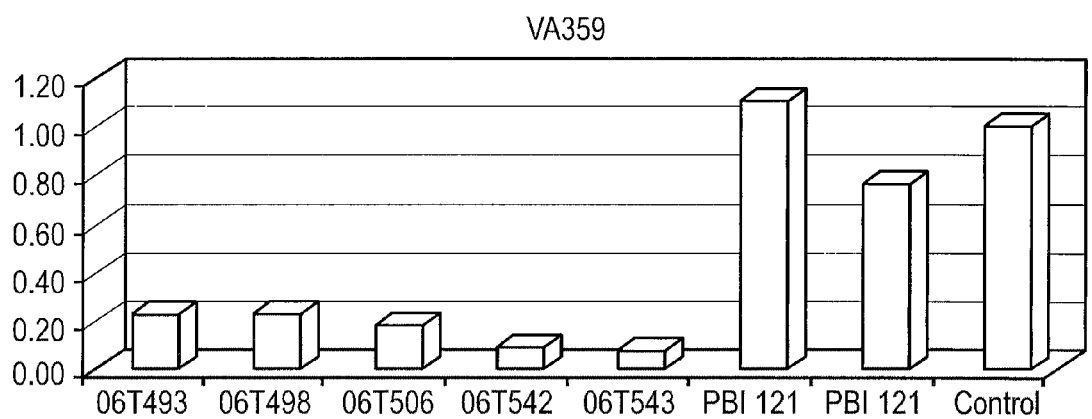

FIGS. 5A-C show normalized NtHMA RNA transcript levels in various first generation (T0) transgenic lines that have been genetically modified to express NtHMA RNAi polynucleotides of interest, as determined by quantitative realtime PCR analysis of leaf lamina extracts. FIG. 5A shows that for multiple independently derived K326 transgenic lines, the RNA transcript levels were reduced by the RNA interference activity of NtHMA (660-915) RNAi polynucleotides. FIG. 5B shows that for multiple, independently derived TN90 transgenic lines, the RNA transcript levels were reduced by the RNA interference activity of NtHMA (660-915) RNAi polynucleotides. FIG. 5C shows that for multiple independently derived VA359 transgenic lines, the RNA transcript levels were reduced by the RNA interference activity of NtHMA (660-915) RNAi polynucleotides. The reduction in NtHMA RNA transcript levels is consistent with the reduction in Cd content measured in the middle leaves for the same transgenic lines tested. "PBI121" represents an expression vector deficient in the RNAi construct encoding NtHMA (660-915) RNAi polynucleotides.

Example 7

Distribution of Cd and Zn in Transgenic Lines Genetically Modified to Express NtHMA RNAi Polynucleotides To determine the effect of NtHMA (660-915) RNAi polynucleotide expression on the distribution of Cd and Zn within the leaf lamina and the root, the metal content of transgenic plants of three varieties were analyzed. Five transgenic lines of each variety, i.e., Flue-cured (K326), Burley (TN90), and Dark (VA359), were selected for exhibiting Cd content at the lowest range in the leaf lamina. The middle leaves and roots of these transgenic plants and control plants were harvested for metal analysis by ICP_MS. For 8 weeks, all plants were grown in Hoaglands medium supplemented with 5 µM $CdCl_2$ prior to harvesting.

Table 2 lists Cd and Zn levels measured in the leaf lamina and the root of several transgenic lines, representing three tobacco varieties, as provided below. In Table 2, the Cd distribution between the leaf lamina and the root were substantially modified by the expression of NtHMA (660-915) RNAi polynucleotides for all three varieties, Flue-cured (K326), Burley (TN90), and Dark (VA359). For the K326 transgenic lines, the % Cd reduction ranged from 97.16-98.54% when compared to Cd levels observed in K326 Control plants. For TN90 transgenic lines, the % Cd reduction ranged from 85.12-90.96% when compared to Cd levels observed in the TN90 Control. For VA359 transgenic lines, the % Cd reduction ranged from 93.24-99.07% when compared to Cd levels observed in the VA359 Control. The VA359 NtHMA-11 transgenic line exhibited the lowest Cd level (1.62 µg/g) and the highest % Cd reduction (99.07%), when compared against two NtHMA RNAi transgene-deficient control lines ("VA359 PBI121") that exhibited Cd levels at 158.3-205.96 µg/g. Comparable root analysis of the transgenic lines showed, that a substantial amount of Cd can accumulate in the root, resulting in fold increase in root Cd levels ranging from 6.90-15.38, relative to the Cd levels observed in the respective controls.

In contrast to the significant Cd reduction in the leaf lamina of transgenic lines, the Zn content of the leaf lamina was not substantially reduced, although some reduction was observed in most transgenic lines, caused by the expression of NtHMA (660-915) RNAi polynucleotides. The Zn content within the root (last column of Table 3) increased in all transgenic lines, resulting in a 4-6 fold increase in the transgenic lines of the K326 and VA359 varieties, and a 3-5 fold increase in the TN90 variety.

Figure 6:
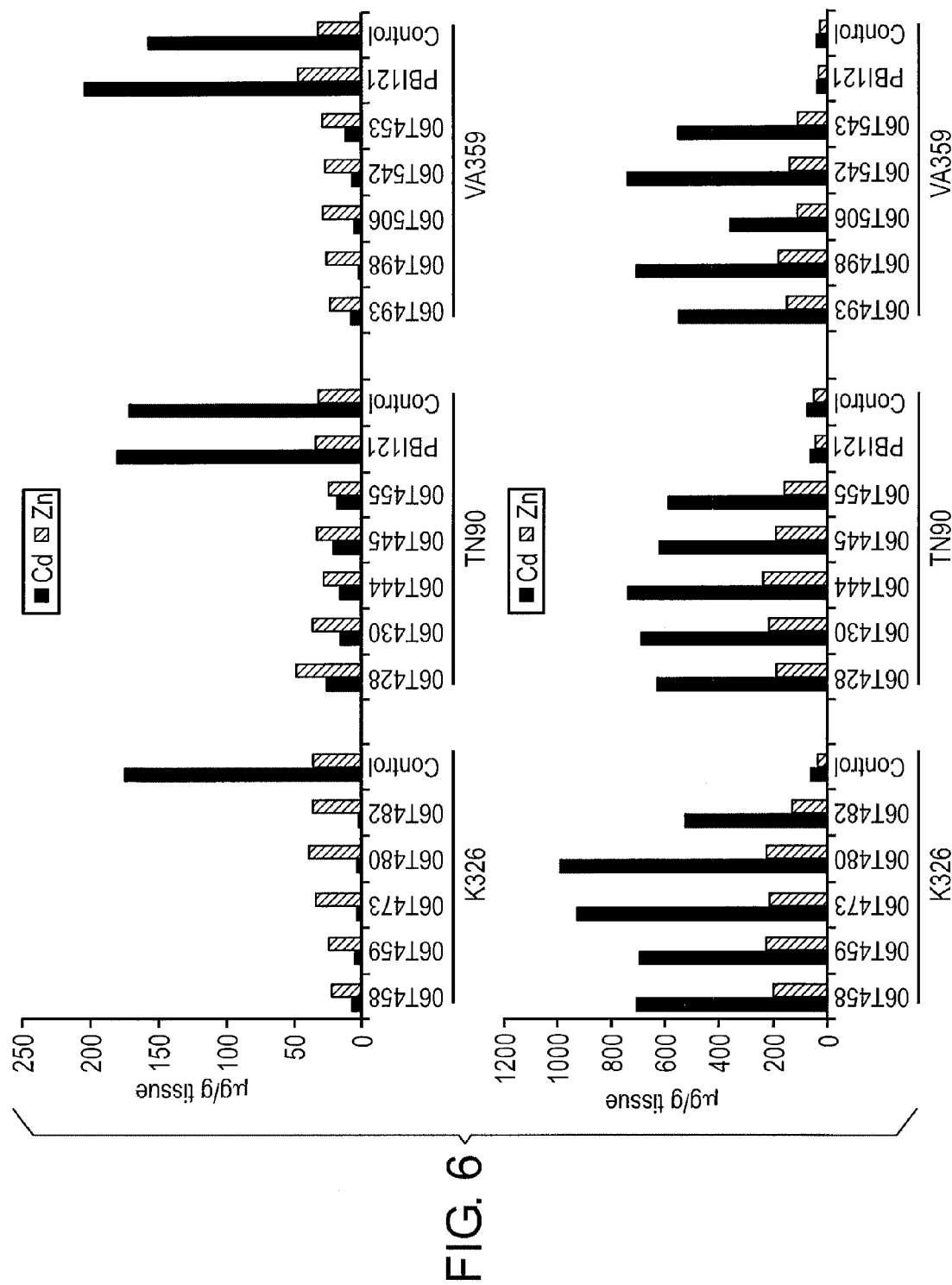
FIG. 6 shows the distribution of Cd and Zn between the leaf lamina and the root of various first generation (T0) transgenic lines that have been genetically modified to express NtHMA RNAi polynucleotides of interest, as presented in Table 2 and described in Example 7.

FIG. 6 shows the distribution of Cd and Zn between the leaf lamina and the root of various first generation transgenic lines that have been genetically modified to express NtHMA RNAi polynucleotides of interest, as presented in Table 2.

TABLE 2

| Transgenic Variety | Leaf | | Root | |
|---|---|---|---|---|
| | Cd µg/g | Zn µg/g | Cd µg/g | Zn µg/g |
| K326 06T458 | 7.09 | 22.2 | 703 | 201 |
| K326 06T459 | 4.97 | 24.1 | 696 | 225 |
| K326 06T473 | 3.7 | 34 | 929 | 215 |
| K326 06T480 | 3.93 | 38.6 | 989 | 224 |
| K326 06T482 | 2.55 | 36.3 | 520 | 126 |
| K326 Control | 174.7 | 36.3 | 64.3 | 35.7 |
| TN90 06T428 | 26.3 | 48.6 | 626 | 184 |
| TN90 06T430 | 16.08 | 37.2 | 684 | 213 |
| TN90 06T444 | 15.98 | 28.1 | 738 | 234 |
| TN90 06T445 | 20.72 | 32.6 | 618 | 186 |
| TN90 06T455 | 17.87 | 24.4 | 582 | 157 |
| TN90 PBI121 | 181.2 | 35.5 | 62.6 | 44.3 |
| TN90 Control | 172.4 | 32.3 | 72.9 | 46.6 |
| VA359 06T493 | 7.59 | 23.1 | 543 | 148 |
| VA359 06T498 | 1.62 | 26.2 | 706 | 175 |
| VA359 06T506 | 5.72 | 28.8 | 351 | 109 |
| VA359 06T542 | 7.03 | 27.1 | 738 | 136 |
| VA359 06T543 | 11.78 | 29.3 | 547 | 106 |
| VA359 PBI121 | 206 | 47.5 | 35.3 | 27.6 |
| VA359 Control | 158.5 | 32.6 | 37.6 | 26.2 |

Example 8

Cd Distribution in Various Tissues of Transgenic Lines Genetically Modified to Express NtHMA RNAi Polynucleotides To determine the effect of NtHMA (1382-1584) RNAi polynucleotide expression on Cd distribution within various tissues (i.e., the bark, lamina, pith, and root), the metal content of several transgenic lines representing two varieties, Burley (TN90) and Flue-cured (K326), were analyzed. Fully matured transgenic plants and control plants were harvested for metal analysis by ICP_MS. For 8 weeks, all plants were grown in 5 µM $CdCl_2$ in Hoaglands medium prior to harvesting.

Table 3 lists Cd content in the bark, lamina, pith, and root tissues of several transgenic lines, as provided below. In Table 3, Cd levels were substantially reduced in the bark, lamina, and pith tissues of all transgenic lines tested when compared that of control plants. The "Control" represents non-transgenic plants. The "PBI121" represents transgenic plants transformed with an expression vector deficient in NtHMA RNAi RNAi construct. The extent of Cd reduction in the bark, pith, and leaf lamina of K326 transgenic lines was significantly greater than that observed in TN90 transgenic lines. The expression of RNAi (1382-1584) polynucleotides in K326 transgenic plants resulted in a 9-11 fold Cd reduction in the bark, a 6-13 fold Cd reduction in the pith, and a 31-32 fold Cd reduction in the leaf lamina. The expression of RNAi (1382-1584) polynucleotides in TN90 transgenic plants resulted in a 4-7 fold Cd reduction in the bark, a 5-8 fold Cd reduction in the pith, and a 6-20 fold Cd reduction in the leaf lamina. In contrast, more modest increases (5-6 fold) in Cd content in the root of these transgenic lines were observed when compared to that of control plants.

Figure 7:
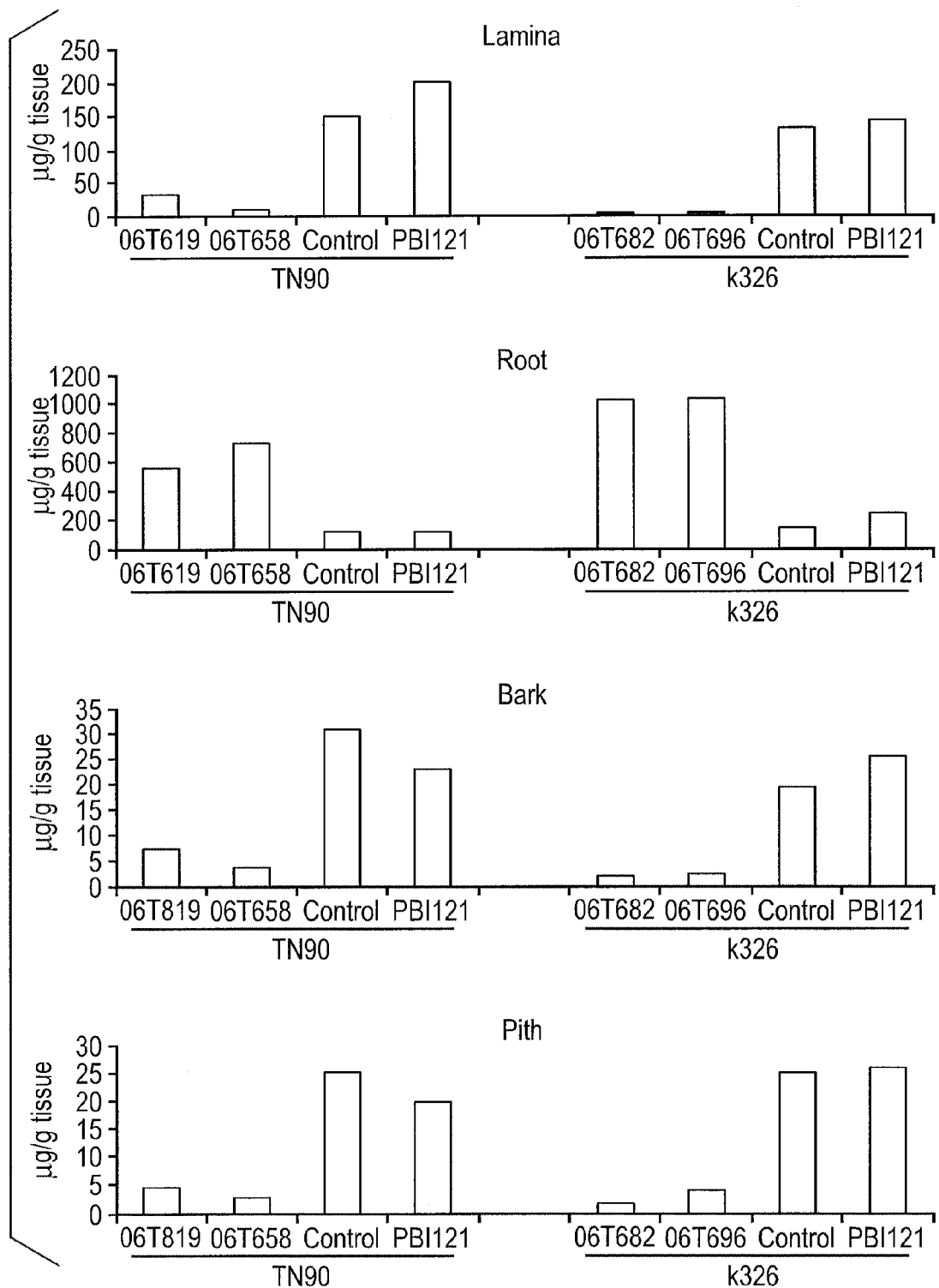
FIG. 7 shows Cd distribution among the bark, leaf lamina, pith, and root tissues of various first generation (T0) transgenic lines that have been genetically modified to express NtHMA RNAi polynucleotides of interest, as presented in Table 3 and described in Example 8.

FIG. 7 shows Cd distribution among the bark, leaf lamina, pith, and the root of various first generation transgenic lines that have been genetically modified to express NtHMA RNAi polynucleotides of interest, as presented in Table 3.

TABLE 3

| Transgenic Seed Variety | Bark Cd | Lamina Cd | Pith Cd | Root Cd |
|---|---|---|---|---|
| TN90 06T619 | 7.36 | 31.1 | 4.67 | 557 |
| TN90 06T658 | 3.76 | 8.89 | 2.89 | 727 |
| TN90 Control | 30.9 | 151 | 25.3 | 115 |
| TN90 PBI121 | 23.1 | 201 | 20 | 124 |
| K326 06T682 | 2.02 | 4.32 | 1.97 | 1020 |
| K326 06T696 | 2.53 | 4.48 | 4.25 | 1030 |
| K326 Control | 19.5 | 133 | 25.3 | 145 |
| K326 PBI121 | 25.5 | 143 | 26.2 | 253 |

Example 9

Cd Reduction in leaf lamina of Second Generation Transgenic Lines Genetically Modified to Express NtHMA RNAi Polynucleotides To determine the effect of NtHMA (660-915) RNAi polynucleotide expression on Cd content in leaf lamina, the metal content of two (T1) transgenic lines of VA359 variety were grown in soil containing variable Cd concentrations for 4 weeks. Two transgenic lines, 06T498 and 06T506, selected as kanamycin positives were screened by PCR. Several 10" Pots filled with sand:soil mixture were saturated with either 0, 0.1, 0.5, or 5 µM $CdCl_2$. Three plants per treatment per transgenic line were grown for 4 weeks by adding Hoaglands medium to the saucer. Total number of leaves, leaf area index, leaf weight, stalk weight, and root weight were observed. Two middle leaves and root samples were freeze-dried and were subjected to heavy metal analysis.

Figure 8:
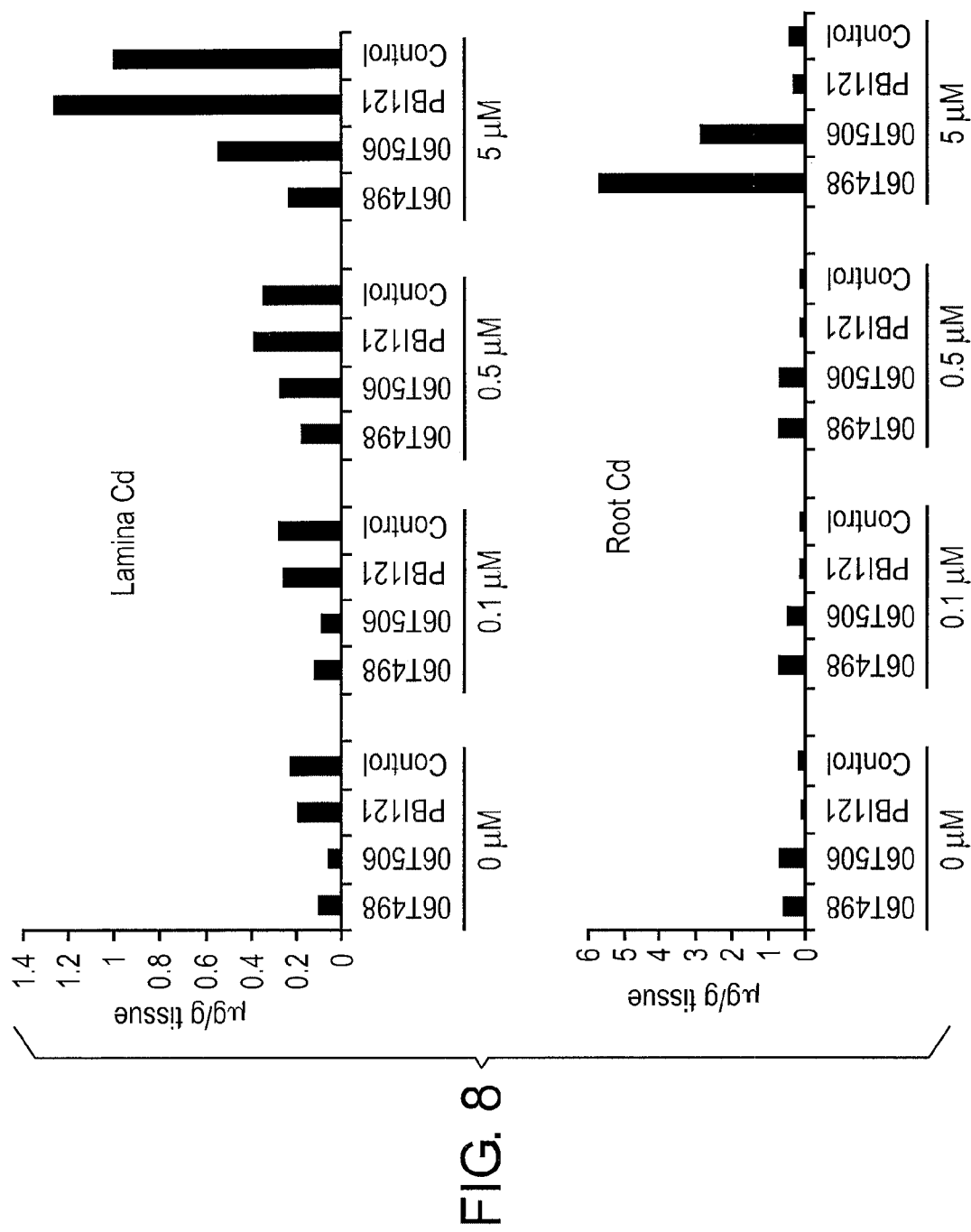
FIG. 8 shows Cd distribution between the leaf lamina and the root of various second generation (T1) transgenic lines that have been genetically modified to express NtHMA RNAi polynucleotides of interest, as described in Example 9.

FIG. 8 shows Cd distribution between the leaf lamina and the root of various second generation (T1) transgenic lines that have been genetically modified to express NtHMA RNAi polynucleotides of interest. In FIG. 8, the Cd content of the transgenic plants was consistently lower than that of control plants at all Cd concentrations tested (0, 0.1, 0.5, and 5 µM). A reduction in Cd content of the leaf lamina (2-4.7 fold) was observed in various transgenic lines tested. The Cd level for the line 06T498 was only ~20% of control plants at 5 µM $CdCl_2$. An increase in root Cd content (4-16 fold) was observed in various transgenic lines tested. The highest root Cd content (a 16 fold increase) was observed for line 06T498 at 5 µM $CdCl_2$. Thus, the reduced heavy metal content in the leaf lamina/shoots in transgenic lines, expressing NtHMA (660-915) RNAi polynucleotide, suggested that the translocation of a substantial amount of heavy metals from the root to the leaf lamina/shoots can be interrupted by RNAi interference. The results are consistent with Cd reduction observed in the leaf lamina of first generation transgenic lines, in that the second generation transgenic lines also demonstrated (a) reduced Cd levels in the leaf lamina, and (b) increased Cd in the roots. The transgenic lines did not demonstrate phenotypical differences in general appearance, growth, and development relative to that of control plants.

Example 10

NtHMA Polynucleotides

A NtHMA polynucleotide will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984); Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. These references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

Among the uses of the disclosed NtHMA polynucleotides, and combinations of fragments thereof, is the use of fragments as probes or primers or in the development of RNAi molecules. Such fragments generally comprise at least about 17 contiguous nucleotides of a DNA sequence. In other embodiments, a DNA fragment comprises at least 30, or at least 60 contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human homologues of the NtHMA sequence identified herein.

Also of potential use are polynucleotides and oligonucleotides that hybridize under reduced stringency conditions, typically moderately stringent conditions, and commonly highly stringent conditions, to an NtHMA polynucleotide described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3-6.4, incorporated herein by reference), and can be readily determined by those having ordinary skill in the art based on, for example, the length and/or base composition of the polynucleotide. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target polynucleotide of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, $T_m$ (° C.)=81.5+16.6(log 10 [Na+])+0.41 (% G+C)−(600/N), where N is the number of bases in the hybrid, and [Na+] is the concentration of sodium ions in the hybridization buffer ([Na+] for 1×SSC=0.165M). Typically, each such hybridizing nucleic acid has a length that is at least 25% (commonly at least 50%, 60%, or 70%, and most commonly at least 80%) of the length of a polynucleotide to which it hybridizes, and has at least 60% sequence identity (e.g., at least 70%, 75%, 80%, 85%, 90%, 95%, 97.5%, or at least 99%) with a polynucleotide to which it hybridizes.

Example 11

NtHMA Polypeptides

A polypeptide may be prepared by culturing transformed or recombinant host cells under culture conditions suitable to express a polypeptide. The resulting expressed polypeptide may then be purified from such culture using known purification processes. The purification of the polypeptide may also include an affinity column containing agents which will bind to the polypeptide; one or more column steps over such affinity resins as concanavalin A-agarose, heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous recombinant polypeptide. The polypeptide thus purified is substantially free of other mammalian polypeptides and is defined herein as an "substantially purified polypeptide"; such purified polypeptides include NtHMA polypeptide, fragment, variant, and the like. Expression, isolation, and purification of the polypeptides and fragments can be accomplished by any suitable technique, including but not limited to the methods described herein.

It is also possible to utilize an affinity column such as a monoclonal antibody generated against polypeptides, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity.

Example 12

Anti-NtHMA Antibodies

In another embodiment, antibodies that are immunoreactive with the polypeptides are provided herein. The NtHMA polypeptides, fragments, variants, fusion polypeptides, and the like, as set forth herein, can be employed as "immunogens" in producing antibodies immunoreactive therewith. Such antibodies specifically bind to the polypeptides via the antigen-binding sites of the antibody. Specifically binding antibodies are those that will specifically recognize and bind with NtHMA family polypeptides, homologues, and variants, but not with other molecules. In one embodiment, the antibodies are specific for polypeptides having an NtHMA amino acid sequence as set forth in SEQ ID NO:2 and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., Immunology Today 4:72, 1983; Cole et al., Proc. Natl. Acad. Sci. USA 80:2026, 1983); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides are also contemplated herein. Such hybridomas can be produced and identified by conventional techniques. For the production of antibodies, various host animals may be immunized by injection with an NtHMA polypeptide, fragment, variant, or mutants thereof. Such host animals may include, but are not limited to, rabbits, mice, and rats, to name a few. Various adjuvants may be used to increase the immunological response. Depending on the host species, such adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Example 13

Double-Stranded RNAs

In one embodiment, double-stranded ribonucleic acid (dsRNA) molecules are provided for inhibiting the expression of the NtHMA gene in a cell (e.g., a plant cell), wherein the dsRNA comprises an antisense strand comprising a region of complementarity which is complementary to at least a part of an mRNA formed in the expression of the NtHMA gene, and wherein the region of complementarity is less than 30 nucleotides in length and wherein said dsRNA, upon contact with a cell expressing said NtHMA gene, inhibits the expression of said NtHMA gene by at least 20%. The dsRNA comprises two RNA strands that are sufficiently complementary to hybridize to form a duplex structure. One strand of the dsRNA (the antisense strand) comprises a region of complementarity that is substantially complementary, and typically fully complementary, to a target sequence, derived from the sequence of an mRNA formed during the expression of the NtHMA gene, the other strand (the sense strand) comprises a region which is complementary to the antisense strand, such that the two strands hybridize and form a duplex structure when combined under suitable conditions. The duplex structure is between about 15 and 30 (e.g., between about 18 and 25), typically between about 19 and 24 (e.g., between 21 and 23) base pairs in length. Similarly, the region of complementarity to the target sequence is between 15 and 30 (e.g., between about 18 and 25), typically between about 19 and 24 (e.g., between 21 and 23) base pairs in length. The dsRNA may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In another aspect, an expression vector can be used to express an RNAi molecule in vivo.

The dsRNA can contain one or more mismatches to the target sequence. In one embodiment, the dsRNA contains more than 3 mismatches. If the antisense strand of the dsRNA contains mismatches to a target sequence, it is typical that the area of mismatch not be located in the center of the region of complementarity. If the antisense strand of the dsRNA contains mismatches to the target sequence, it is typical that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the NtHMA gene, the dsRNA preferably does not contain any mismatch within the central 13 nucleotides. The methods described herein can be used to determine whether a dsRNA containing a mismatch to a target sequence is effective in inhibiting the expression of the NtHMA gene.

In one embodiment, at least one end of the dsRNA has a single-stranded nucleotide overhang of 1 to 4 (e.g., 1 or 2 nucleotides). dsRNAs having at least one nucleotide overhang have inhibitory properties. The dsRNA may also have a blunt end, typically located at the 5'-end of the antisense strand.

In yet another embodiment, the dsRNA is chemically modified to enhance stability. The nucleic acids may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate (see, e.g., Wagner, Nat. Med. (1995) 1:1116-8). Thus, at least one 2'-hydroxyl group of the nucleotides on a dsRNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Oligonucleotides containing the locked nucleotide are described in Koshkin, A. A., et al., Tetrahedron (1998), 54: 3607-3630) and Obika, S. et al., Tetrahedron Lett. (1998), 39: 5401-5404). Introduction of a locked nucleotide into an oligonucleotide improves the affinity for complementary sequences and increases the melting temperature by several degrees (Braasch, D. A. and D. R. Corey, Chem. Biol. (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, a ligand conjugated to the dsRNA is a substrate for receptor-mediated endocytosis. These approaches have been used to facilitate cell permeation of antisense oligonucleotides. In certain instances, conjugation of a cationic ligand to oligonucleotides often results in improved resistance to nucleases. Representative examples of cationic ligands are propylammonium and dimethylpropylammonium. Anti-sense oligonucleotides can retain their high binding affinity to mRNA when the cationic ligand is dispersed throughout the oligonucleotide. See M. Manoharan Antisense & Nucleic Acid Drug Development 2002, 12, 103 and references therein.

Example 15

Methods for Identifying NtHMA Modulatory Agents

Methods for identifying agents that can modulate NtHMA expression level and/or activity are disclosed below. Candidates ("a test agent") that may be screened to identify NtHMA-specific modulatory activity include small molecules, chemicals, peptidomimetics, antibodies, peptides, polynucleotides (e.g., RNAi, siRNA, antisense or ribozyme molecules), and agents developed by computer-based design. Modulation of NtHMA includes an increase or decrease in activity or expression. For example, a method for identifying candidates that can modulate NtHMA expression and/or activity, comprises: contacting a sample containing an NtHMA polypeptide or polynucleotide with a test agent under conditions that allow the test agent and the NtHMA polypeptide or polynucleotide to interact, and measuring the expression and/or activity of the NtHMA polypeptide in the presence or absence of the test agent.

In one embodiment, a cell containing an NtHMA polynucleotide is contacted with a test agent under conditions such that the cell and test agent are allowed to interact. Such conditions typically include normal cell culture conditions consistent with the particular cell type being utilized, known in the art. It may be desirable to allow the test agent and the cell to interact under conditions associated with increased temperature or in the presence of regents that facilitate the uptake of the test agent by the cell. A control is treated similarly but in the absence of the test agent. Alternatively, the NtHMA activity or expression may be measured prior to contact with the test agent (e.g., the standard or control measurement) and then again following contact with the test agent. The treated cell is then compared to the control and a difference in the expression or activity of NtHMA compared to the control is indicative of an agent that modulates NtHMA activity or expression.

When NtHMA expression is being measured, detecting the amount of mRNA encoding an NtHMA polypeptide in the cell can be quantified by, for example, PCR or Northern blot. Where a change in the amount of NtHMA polypeptide in the sample is being measured, detecting NtHMA by use of anti-NtHMA antibodies can be used to quantify the amount of NtHMA polypeptide in the cell using known techniques. Alternatively the biological activity (e.g., heavy metal transport) can be measured before and after contact with the test agent.

It will be appreciated that, although specific embodiments of the invention have been described herein for purposes of illustration, various modifications may be made without departing from the spirit and the scope of the invention. Accordingly, the invention is not limited except as by the appended claims. Unless defined otherwise, all technical and scientific terms have standard meaning as commonly understood to persons skilled in the art. Although exemplary methods, devices, and materials have been described with particularity, alternative methods and materials, that may be similar or equivalent to those described herein, are applicable for making the disclosed compositions and for practicing the disclosed methods.

Any publication cited or described herein provides relevant information disclosed prior to the filing date of the present application. Statements herein are not to be construed as an admission that the inventors are not entitled to antedate such disclosures.

We claim:

1. An isolated polynucleotide selected from the group consisting of:
   (i) a polynucleotide comprising a sequence having at least 90% sequence identity to SEQ ID NO: 1, and encoding a NtHMA transporter having P1B-type ATPase activity;
   (ii) a polynucleotide comprising a sequence having at least 90% sequence identity to SEQ ID NO: 3, and encoding a NtHMA transporter having P1B-type ATPase activity;
   (iii) a polynucleotide comprising a sequence having at least 90% sequence identity to SEQ ID NO: 47, and encoding a NtHMA transporter having P1B-type ATPase activity;
   (iv) a polynucleotide comprising a sequence encoding a polypeptide having at least 90% sequence identity to SEQ ID NO:2, wherein the polypeptide is a NtHMA transporter having P1 B-type ATPase activity; and
   (v) a polynucleotide comprising a sequence encoding a polypeptide having at least 90% sequence identity to SEQ ID NO: 49, wherein the polypeptide is a NtHMA transporter having P1B-type ATPase activity.

2. An expression vector comprising the isolated polynucleotide of claim 1.

3. A transgenic plant made by a process comprising introducing the isolated polynucleotide of claim 1 into a plant.

4. A transgenic cell line made by a process comprising introducing the isolated polynucleotide of claim 1 into a cell line.

5. A consumable tobacco product comprising transgenic leaves harvested from the transgenic plant of claim 3.

6. An NtHMA RNAi construct capable of inhibiting the expression of an NtHMA messenger RNA to which it corresponds, the construct comprising: a first sequence having at least 90% sequence identity to SEQ ID NO:3 or 47; a second sequence; and a third sequence having a reverse complementary sequence of the first sequence, positioned in the same orientation as the first sequence, wherein the second sequence is positioned between the first sequence and the third sequence, and the second sequence is operably-linked to the first sequence and to the third sequence.

7. A transgenic plant comprising the RNAi of claim 6 having a reduced Cd level in at least a part of the plant compared to the part in a non-transgenic counterpart.

8. A consumable tobacco product comprising transgenic leaves harvested from the transgenic plant of claim 7.

9. The product of claim 8, wherein a % Cd reduction is a value of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

10. The product of claim 8, wherein the Cd content is a value ranging from about 0.01 to about 0.05 ppm, from about 0.01 to about 0.1 ppm, from about 0.01 to about 0.5 ppm, from about 0.01 to about 1.0 ppm, or from about 0.01 to about 5 ppm.

11. A method for reducing Cd levels in at least a part of a plant, comprising:
    reducing levels of an NtHMA mRNA in the plant by causing expression of the RNAi construct of claim 6.

12. The method of claim 11, wherein the RNAi construct comprises:
    a first sequence having at least 90% sequence identity to SEQ ID NO:3 or 47;
    a second sequence; and
    a third sequence having a reverse complementary sequence of the first sequence, positioned in the same orientation as the first sequence,
    wherein the second sequence is positioned between the first sequence and the third sequence, and the second sequence is operably-linked to the first sequence and to the third sequence.

13. The method of claim 11, wherein following expression of the RNAi construct, the part of the plant has a Cd content reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

14. The method of claim 11, wherein following expression of the RNAi construct, the part of the plant has a Cd content ranging from about 0.01 to about 0.05 ppm, from about 0.01 to about 0.1 ppm, from about 0.01 to about 0.5 ppm, from about 0.01 to about 1.0 ppm, or from about 0.01 to about 5 ppm.

\* \* \* \* \*